United States Patent [19]
Bowersox et al.

[11] Patent Number: 6,054,429
[45] Date of Patent: *Apr. 25, 2000

[54] EPIDURAL METHOD OF PRODUCING ANALGESIA

[75] Inventors: S. Scott Bowersox; Theresa Gadbois, both of Menlo Park; Mark Raymond Pettus, San Jose; Robert R. Luther, Los Altos Hills, all of Calif.

[73] Assignee: Elan Pharmaceuticals, Inc., South San Francisco, Calif.

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/613,400

[22] Filed: Mar. 8, 1996

[51] Int. Cl.$^7$ .................................................... A61K 38/00
[52] U.S. Cl. ............................ 514/12; 530/300; 530/324
[58] Field of Search .............................. 514/12; 530/300, 530/324

[56] References Cited

U.S. PATENT DOCUMENTS

| | | | |
|---|---|---|---|
| 5,051,403 | 9/1991 | Miljanich et al. | 514/12 |
| 5,163,901 | 11/1992 | Eldor | 604/44 |
| 5,364,842 | 11/1994 | Justice et al. | 514/12 |
| 5,451,408 | 9/1995 | Mezei et al. | 424/450 |

FOREIGN PATENT DOCUMENTS

| | | |
|---|---|---|
| 3926287 A1 | 2/1991 | Germany . |
| WO 91/07980 | 6/1991 | WIPO . |
| WO 93/10145 | 5/1993 | WIPO . |
| WO 93/13128 | 7/1993 | WIPO . |
| WO 95/01436 | 1/1995 | WIPO . |

OTHER PUBLICATIONS

Bernards, C.M., "Effect of (Hydroxypropyl)-β-cyclodextrin on Flux of Morphine, Fentanyl, Sufentanil, and Alfentanil Through the Spinal Meninges of Monkey," *Journal of Pharmaceutical Sciences*, 83(5):620–622 (1994).

Bernards, C.M. and Hill, H.F., "Physical and Chemical Properties of Drug Molecules Governing Their Diffusion Through the Spinal Meninges," *Anesthesiology*, 77(4):750–756 (1992).

Davar, G. et al., "MK–801 Blocks the Development of Thermal Hyperalgesia in a Rat Model of Experimental Painful Neuropathy," *Brain Research*, 553:327–330 (1991).

Dialog Information Services, File 351, WPIL Dialog Accession No. 010083868, WPI Accession No. 94–351581/44, Bristol–Myers Squibb Co: "Stabilised Injection Prepn— Comprises Deoxythymidine Nucleoisede and Stabiliser(s) Selected from Sugar Alcohol, Benzyl Alcohol, Phenol, etc"; & JP, A, 6247879, 940906, 9444 (Basic).

White, D.M., "Mechanism of Prostaglandin $E_2$–Induced Substance P Release from Cultured Sensory Neurons," *Neuroscience*, 70(2):561–565 (1996).

Xiao, W.–H. and Bennett, G.J., "Inhibition of Neuropathic Pain By N–type Calcium Channel Blockade with Omega- –conopeptides Applied to the Site of Nerve Injury," *Society for Neuroscience Abstracts*, 20:559 (1994).

U.S. Patent Application No. 08/965,918 filed Nov. 7, 1997.

Malmberg et al. 'Effect of Continuous Intrathecal Infusion of Conopeptides, N–type Calcium–Channel Blockers, on Behavior and Antinociception in the Formalin and Hot–plate Tests in Rats', vol. 60, No. 1, pp. 83–90, 1995.

File DRUGU on STN No. 87–25878. Payne, R. 'Role of Epidural and Intrathecal Narcotics and Peptides in teh Management of Cancer Pain', Med. Clin. North Am. vol. 71, No. 2, pp. 313–327, 1987.

File Medline on STN No. 92081807. Littrell R A. 'Epidural Analgesia', vol. 48, No. 11, pp. 2460–2474, Nov. 1991.

Bernards et al. 'Physical and Chemical Properties of Drug Molecules Governing their Diffuse Trhough the Spinal Meninges', Anesthesiology, vol. 77, pp. 750–756, 1992.

Bernards et al. 'Palmitoyl Carnitine Increases the Transmeningeal Flus of Hydrophilic but not Hydrophobic Compounds In Vitro', Anesthesiology, vol. 84, No. 2, pp. 392–396, Feb. 1996.

*Primary Examiner*—Cecilia J. Tsang
*Assistant Examiner*—Anism Gupta
*Attorney, Agent, or Firm*—Carol A. Stratford; Judy M. Mohr; Dehlinger & Associates

[57] ABSTRACT

A improved method of treating pain is disclosed. The method includes administering to a subject an N-type voltage-sensitive calcium channel blocking omega conopeptide which is characterized by its ability to (a) inhibit electrically stimulated contraction of the guinea pig ileum, and (b) bind selectively to omega conopeptide MVIIA binding sites present in neuronal tissue. The method includes administering the omega conopeptide epidurally, preferably so that the compound is in prolonged or sustained contact with the epidural region.

9 Claims, 23 Drawing Sheets

|  | 1 | 5 | 10 | 15 | 20 | 25 | 30 |
|---|---|---|---|---|---|---|---|
| MVIIA/SNX-111 | C | K G K G A | K C S R L M Y | D C C T G S C | - R - S G K | - C |
| MVIIB/SNX-159 | C | K G K G A | S C H R T S Y | D C C T G S C | N R - - G K | - C |
| GVIA/SNX-124 | C | K S X G S | S C S X T S Y | N C C R - S C | N X Y T - K R C | - Y |
| GVIIB/SNX-178 | C | K S X G T | X C S R G M R | D C C T - S C | L L Y S N K - C R R | Y |
| RVIA/SNX-182 | C | K P X G S | X C R V S S Y | N C C S - S C | K S Y - N K K C G |  |

Fig. 1A

|  | 1 | 5 | 10 | 15 | 20 | 25 | 30 |
|---|---|---|---|---|---|---|---|
| SVIA/SNX-157 | C | R S S G S | X C G V T S I | - C C - | G R C - | - Y R G K - | C T |
| TVIA/SNX-185 | C | L S X G S S | C S X T S Y N | C C R - | S C N X Y S | - R K C R | |
| SVIB/SNX-183 | C | K L K G Q S | C R K T S Y D | C C S G | S C G R - | S G K - C | |
| MVIIC/SNX-230 | C | K G K G A P | C R K T M Y D | C C S G | S C G R - | R G K - C | |
| SNX-231 | C | K G K G A X | C R K T M Y D | C C S G | S C G R - | R G K - C | |

Fig. 1B

| | 1 | | | | 5 | | | | | 10 | | | | | 15 | | | | | 20 | | | | | 25 | |
|---|---|---|---|---|---|---|---|---|---|---|---|---|---|---|---|---|---|---|---|---|---|---|---|---|---|---|
| MVIIA (SNX-111) | C | K | G | K | G | A | K | C | S | R | L | M | Y | D | C | C | T | G | S | C | R | S | G | K | C | -NH₂ |
| SNX-190 | - | - | - | - | A | - | - | - | - | - | - | - | - | - | - | - | - | - | - | - | - | - | - | - | - | NH₂ |
| SNX-191 | - | - | A | - | - | - | - | - | - | - | - | - | - | - | - | - | - | - | - | - | - | - | - | - | - | NH₂ |
| SNX-193 | - | - | - | - | - | - | - | - | - | - | - | - | - | - | - | - | - | - | - | - | - | - | - | - | - | G-OH |
| SNX-194 | - | - | - | - | - | - | - | - | - | - | - | Nle | - | - | - | - | - | - | - | - | - | - | - | - | - | NH₂ |
| SNX-195 | - | - | - | - | - | - | - | - | - | - | - | - | - | - | - | - | - | - | - | - | - | - | - | A | - | NH₂ |
| SNX-196 N- | - | - | - | - | - | - | - | - | - | - | - | - | - | - | - | - | - | - | - | - | - | - | - | - | - | G-OH |
| SNX-197 NS- | - | - | - | - | - | - | - | - | - | - | - | - | - | - | - | - | - | - | - | - | - | - | - | - | - | NH₂ |
| SNX-198 | - | - | - | - | - | - | - | - | - | - | - | - | - | - | - | - | - | - | - | - | - | A | - | - | - | NH₂ |
| SNX-199 | - | - | - | - | - | - | - | - | - | - | A | - | - | - | - | - | - | - | - | - | - | - | - | - | - | NH₂ |

Fig. 2A

| | 1 | | | | 5 | | | | | 10 | | | | | 15 | | | | | 20 | | | | | 25 | |
|---|---|---|---|---|---|---|---|---|---|---|---|---|---|---|---|---|---|---|---|---|---|---|---|---|---|---|
| SNX-200 | – | – | – | – | A | – | – | – | – | – | – | – | – | – | – | – | – | – | – | – | – | – | – | – | NH$_2$ |
| SNX-201 | – | – | – | – | – | – | – | – | R | K | T | S | – | – | – | – | – | – | – | – | – | – | – | – | NH$_2$ |
| SNX-239 | – | – | – | – | – | – | – | – | – | L | – | – | – | – | – | – | – | – | – | – | – | – | – | – | NH$_2$ |
| SNX-240 Ac- | – | – | – | – | – | – | – | – | – | L | – | – | – | – | – | – | – | – | – | – | – | – | – | – | |
| SNX-273 | – | – | – | – | – | – | – | – | – | A | – | – | – | – | – | – | – | – | – | – | – | – | – | – | NH$_2$ |
| SNX-279 | – | – | – | – | – | – | – | – | – | – | M(O-) | – | – | – | – | – | – | – | – | – | – | – | – | – | NH$_2$ NH$_2$ |
| SVIB (SNX-183) | C | K | L | K | G | Q | S | C | R | K | T | S | Y | D | C | C | S | G | S | C | G | R | S | G | K C NH$_2$ |
| SNX-202 | – | – | – | – | – | – | – | – | – | S | R | L | M | – | – | – | – | – | – | – | – | – | – | – | NH$_2$ |
| TVIA (SNX-185) | C | L | S | X | G | S | S | C | S | X | T | S | Y | N | C | C | R | S | C | N | X | Y | S | R | K C R NH$_2$ |
| SNX-207 | – | – | – | – | – | – | – | – | – | – | R | L | M | – | – | – | – | – | – | – | – | – | – | – | NH$_2$ |
| SNX-236 | – | – | – | – | – | – | – | – | – | – | R | L | M | – | – | – | – | – | – | – | P | – | – | – | NH$_2$ |

Fig. 2B

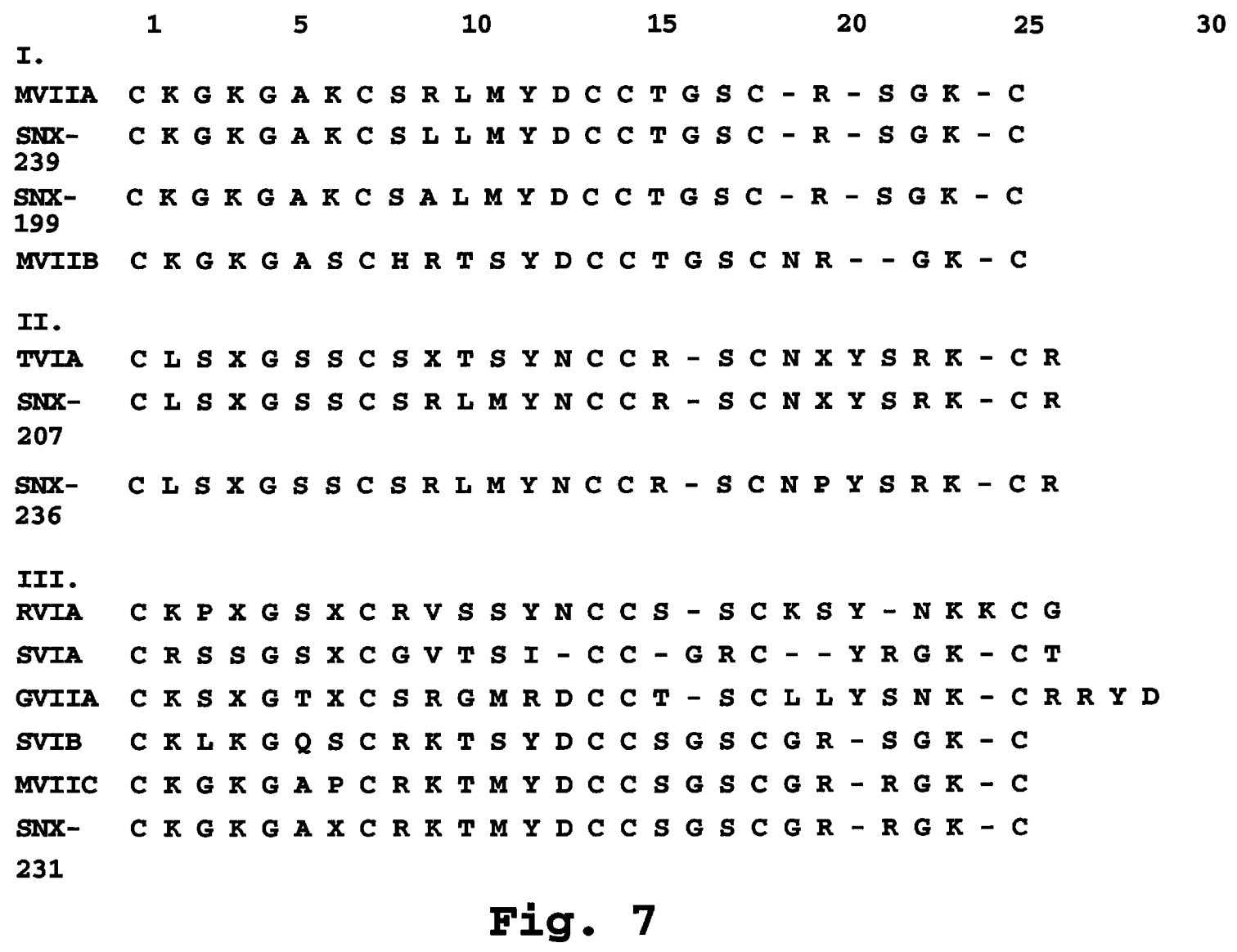

|   | 1 | | | | 5 | | | | | 10 | | | | | 15 | | | | | 20 | | | | | 25 | | | | | 30 |
|---|---|---|---|---|---|---|---|---|---|---|---|---|---|---|---|---|---|---|---|---|---|---|---|---|---|---|---|---|---|
| I. | | | | | | | | | | | | | | | | | | | | | | | | | | | | | |
| MVIIA | C | K | G | K | G | A | K | C | S | R | L | M | Y | D | C | C | T | G | S | C | - | R | - | S | G | K | - | C |
| SNX-239 | C | K | G | K | G | A | K | C | S | L | L | M | Y | D | C | C | T | G | S | C | - | R | - | S | G | K | - | C |
|

EPIDURAL METHOD OF PRODUCING ANALGESIA

FIELD OF THE INVENTION

The present invention relates to an improved method of providing analgesia for nociceptive and neuropathic pain.

REFERENCES

Ahmad, S. N. and Miljanich, G. P., *Brain Research* 453:247–256 (1988).
Bennett, G. J. and Xie, Y.-K., *Pain* 33:87–107 (1988).
Bennett, J. P. et al., in *NEUROTRANSMITTER RECEPTOR BINDING*, pp. 61–89; Raven Press, New York, N.Y. (1983).
Ben-Sreti, M. M., et al., *Eur. J. Pharmacol.* 90:385–391 (1983).
Contreras, E., et al., *Eur. J. Pharmacol.* 148:463–466 (1988).
Dixon, W. J., *Ann. Rev. Pharmacol. Toxicol.* 20:441–462 (1976).
Gohil, K., et al., *Brain Research*, 653:258–266 (1994).
Gray, W., et al., *Annual Review of Biochemistry* 57:665–700 (1988).
Jadad, A. R., et al., *Lancet* 339:1367–1371 (1992).
Kenakin, T. P., in *PHARMACOLOGIC ANALYSIS OF DRUG-RECEPTOR INTERACTION*, Raven Press, New York, N.Y. (1987).
Kim, S. H. and Chung, J. M., *Pain* 50:355–363 (1992).
McCleskey, E. W., et al., *Proc. Natl. Acad. Sci. USA* 84:4327–31 (1987).
McGeer, P. L., et al., in *MOLECULAR NEUROBIOLOGY OF THE MAMMALIAN BRAIN*, Plenum Press, New York, N.Y. (1987).
Miljanich, G. P., et al., *Annual Rev. Pharmacol. Toxicol.* 35: 707–735 (1995).
Nowycky, M. C., et al., *Nature (London)* 316:440–443 (1985).
Olivera, B., et al., *Biochemistry* 23:5087–5090 (1984).
Sher, E. et al., *FASEB J.* 5:2677–2683 (1991).
Sher, E. and Clementi, F., *Neuroscience* 42301–42307 (1991).
Yaksh, T. L., and Rudy, T. A., *Physiol. Behav.* 17:1031–1036 (1976).
Yamashiro, D., *Int. J. Peptide Protein Res.* 30:9–12 (1987).

BACKGROUND OF THE INVENTION

Chronic or intractable pain, such as may occur in conditions such as bone degenerative diseases and cancer, is a debilitating condition which is treated with a variety of analgesic agents, and often opioid compounds, such as morphine.

In general, brain pathways governing the perception of pain are still incompletely understood, sensory afferent synaptic connections to the spinal cord, termed "nociceptive pathways" have been documented in some detail. In the first leg of such pathways, C- and A-fibers which project from peripheral sites to the spinal cord carry nociceptive signals. Polysynaptic junctions in the dorsal horn of the spinal cord are involved in the relay and modulation of sensations of pain to various regions of the brain, including the periaqueductal grey region (McGeer). Analgesia, or the reduction of pain perception, can be effected directly by decreasing transmission along such nociceptive pathways. Analgesic opiates are thought to act by mimicking the effects of endorphin or enkephalin peptide-containing neurons, which synapse presynaptically at the C- or A-fiber terminal and which, when they fire, inhibit release of neurotransmitters, including substance P. Descending pathways from the brain are also inhibitory on C- and A-fiber firing.

Neuropathic pain is a particular type of chronic pain that has a complex and variable etiology. It is frequently a chronic condition attributable to complete or partial transection of a nerve, trauma or injury to a nerve, nerve plexus or soft tissue, or other conditions, including cancer, AIDS and idiopathic causes. Neuropathic pain is characterized by hyperalgesia (lowered pain threshold and enhanced pain perception) and by allodynia (pain from innocuous mechanical or thermal stimuli). The condition is progressive in nature. Because the hyperesthetic component of neuropathic pain does not respond to the same pharmaceutical interventions as does more generalized and acute forms of pain, development of effective long-term treatment modalities has been problematic.

Opioid compounds (opiates) such as morphine, while effective in producing analgesia for many types of pain, are not always effective, and may induce tolerance in patients. When a subject is tolerant to opioid narcotics, increased doses are required to achieve a satisfactory analgesic effect. At high doses, these compounds produce side effects, such as respiratory depression, which can be life threatening. In addition, opioids frequently produce physical dependence in patients. Dependence appears to be related to the dose of opioid taken and the period of time over which it is taken by the subject. For this reason, alternate therapies for the management of chronic pain are widely sought after. In addition, compounds which serve as either a replacement for or as an adjunct to opioid treatment in order to decrease the dosage of analgesic compound required, have utility in the treatment of pain, particularly pain of the chronic, intractable type.

Although various types of calcium blocking agents, including a number of L-type calcium channel antagonists and calcium chelators, have been tested as adjunct therapy to morphine analgesia, positive results are attributed to direct effects on calcium availability, since calcium itself is known to attenuate the analgesic effects of certain opioid compounds (Ben-Sreti). EGTA, a calcium chelating agent, is effective in increasing the analgesic effects of opioids. However, results from tests of calcium antagonists as adjunct therapy to opioids have been contradictory; some L-type calcium channel antagonists have been shown to increase the effects of opioids, while others of these compounds have been shown to decrease opioid effects (Contreras).

U.S. Pat. No. 5,051,403 describes the use of omega-conopeptides having defined binding/inhibitory properties in the treatment of ischemia-related neuronal damage. U.S. Pat. No. 5,364,842 demonstrates the effectiveness of omega-conopeptide compositions in certain animal models of pain. Specifically, omega-conopeptides MVIIA and TVIA and derivatives thereof having related inhibitory and binding activities were demonstrated to produce analgesia in animal models of analgesia in which morphine is the standard positive control. PCT/US92/11349 discloses that such conopeptides also produce relief from neuropathic pain, where morphine is not expected to produce positive results. Co-pending U.S. patent application No. 08/496,847 discloses that such compounds are effective in preventing progression of neuropathic pain.

In the treatment methods discussed in the foregoing disclosures, omega conopeptides were generally administered via routes that would result in direct application of the compounds into the bloodstream, cerebral spinal fluid, or active site, such as to afflicted nerve terminals such as damaged nerves. For example, U.S. application Ser. No. 08/496,847 describes a number of treatment modalities using omega conopeptides with specific reference to neuropathic pain. While disclosing epidural administration, e.g., administration of drug to a region outside the meninges of the spinal cord, the specification states that for administration of omega conopeptides, such a treatment mode should also include a membrane permeation enhancer in view of the generally hydrophilic, charged nature of omega conopeptides and the permeation properties of the spinal meninges.

It is the discovery of the present invention that omega conopeptides can provide pain relief when administered epidurally, at doses that are comparable to effective analgesic doses using intrathecal administration (e.g., direct delivery to the spinal fluid) with inclusion in the formulation of a membrane permeability enhancer. As described herein, such epidural administration is particularly effective when it is carried out in such a way that the administered compound is placed in prolonged contact with the epidural space, and more particularly, with the spinal meninges. The improved method has the advantage that epidural administration is technically less demanding than intraspinal administration of compound and poses fewer risks to the patient. Accordingly, the present invention is directed to this discovery of an improved treatment modality for pain.

SUMMARY OF THE INVENTION

The invention is concerned with an improved method for treating pain by administration of analgesic omega conopeptides. The method includes, in one aspect, administering to a subject, via an epidural route, an omega conopeptide which is effective (a) to inhibit electrically stimulated contraction of the guinea pig ileum, and (b) to bind selectively to omega conopeptide MVIIA binding sites present in neuronal tissues. Compounds that are used in the method of the invention will have activities that are within the ranges of such activities of omega-conotoxins MVIIA and TVIA. In a preferred embodiment, the compounds also have a selectivity ratio of binding at an MVIIA binding site to binding at a site 2 omega conopeptide binding site which is within the range of selectivity ratios determined for omega conopeptides MVIIA/SNX-111, SNX-199, SNX-236, SNX-239 and TVIA/SNX-185.

Generally, in accordance with the discovery of the present invention, it is appreciated that, in order to minimize the total dose of compound delivered, the epidural administration is carried out over a period of time such that the conopeptide is in prolonged contact with the epidural region. Under such circumstances, it has been found that the dosage used is in the range of an effective intrathecal analgesic dose administered over an equivalent period of time.

In a preferred embodiment, such administration can be effected by use of a continuous infusion set-up, such as a continuous infusion pump. However, the invention includes use of other sustained release paradigms as well. When continuous infusion methods are used, in another preferred embodiment, the dosage will be measured over a twenty-four hour time period. However, it is appreciated that lesser time periods may be measured.

In another preferred embodiment, the administration is carried out in the absence of means for enhancing permeation of the conopeptide through meningeal membranes.

While the treatment method can be used to treat most types of pain for which spinal administration is advantageous, it is appreciated that it is particularly effective in treatment and prevention of progression of neuropathic pain characterized by allodynia.

In yet another preferred embodiment, the conopeptide used in the improved treatment method is one of SEQ ID NO: 1 (MVIIA/SNX-111), SEQ ID NO: 7 (TVIA/SNX-185), SEQ ID NO: 30 (SNX-236), SEQ ID NO: 2 (SNX-159), SEQ ID NO: 32 (SNX-239), SEQ ID NO: 33 (SNX-199), SEQ ID NO: 35 (SNX-273), SEQ ID NO: 36 (SNX-279), and derivatives of these compounds, as defined herein. In still another a preferred embodiment, the conopeptide is SEQ ID NO: 1 (MVIIA/SNX-111).

A preferred formulation for use in the claimed treatment method is one that includes an anti-oxidant effective to prevent methionine oxidation. Examples of such an anti-oxidant include lactate buffer and methionine.

BRIEF DESCRIPTION OF THE DRAWINGS

FIGS. 1A and 1B show primary sequences of several natural omega-conopeptides, MVIIA/SNX-111 (SEQ ID NO: 01), MVIIB/SNX-159 (SEQ ID NO: 02), GVIA/SNX-124 (SEQ ID NO: 03), GVIIA/SNX-178 (SEQ ID NO: 04), RVIA/SNX-182 (SEQ ID NO: 05), SVIA/SNX-157 (SEQ ID NO: 06), TVIA/SNX-185 (SEQ ID NO: 07), SVIB/SNX-183 (SEQ ID NO: 08), and MVIIC/SNX-230 (SEQ ID NO: 29), and SNX-231 (SEQ ID NO: 21);

FIGS. 2A and 2B show primary sequences of analog omega-conopeptides SNX-190 (SEQ ID NO: 09), SNX-191 (SEQ ID NO: 10), SNX-193 (SEQ ID NO: 11), SNX-194 (SEQ ID NO: 12), SNX-195 (SEQ ID NO: 13), SNX-196 (SEQ ID NO: 14), SNX-197 (SEQ ID NO: 15), SNX-198 (SEQ ID NO: 16), SNX-199 (SEQ ID NO: 33), SNX-200 (SEQ ID NO: 17), SNX-201 (SEQ ID NO: 18), SNX-239 (SEQ ID NO: 32), SNX-240 (SEQ ID NO: 34), SNX-202 (SEQ ID NO: 19), SNX-207 (SEQ ID NO: 20), SNX-236 (SEQ ID NO: 30), SNX-273 ([ala$^{12}$-SNX-111; SEQ ID NO: 35), and SNX-279 (Met(0)$^{12}$-SNX-111; SEQ ID NO: 36) and their relationships to SNX-111 (SEQ ID NO: 01), SNX-185 (SEQ ID NO: 07) or SNX-183 (SEQ ID NO: 08), where Nle indicates norleucine, and Met(0) indicates a sulfoxy-methionine substitution;

FIG. 7 shows omega-conopeptide groupings: I, MVIIA, SNX-199 (SEQ ID NO: 33), MVIIB and SNX-239 (SEQ ID NO: 32), II, TVIA, SNX-207 and SNX-236, III, RVIA, SVIA, GVIIA, SVIB, MVIIC, SNX-231;

DETAILED DESCRIPTION OF THE INVENTION

Figure 3:
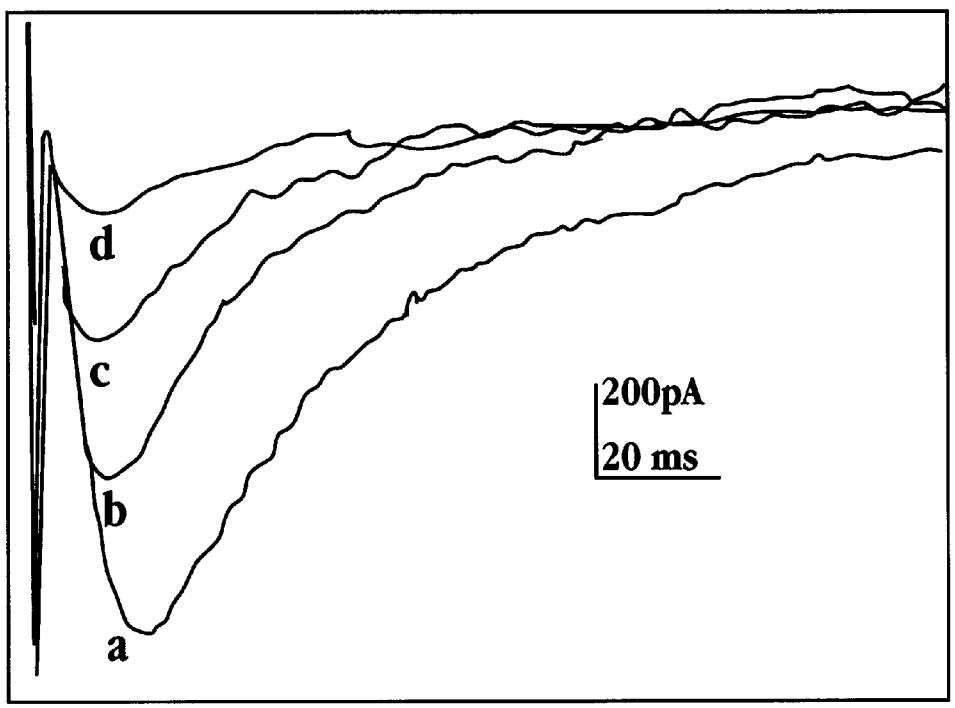
FIG. 3 shows voltage-gated calcium current traces induced by a voltage step from −100 or −80 mV to −20 mV in untreated N1E-115 neuroblastoma cells (curve a) and in neuroblastoma cells exposed to increasing concentrations of OCT MVIIA (SNX-111) (curves b–d)

I. N-type Voltage-Sensitive Calcium Channel Blocking Compounds

Voltage-gated calcium channels are present in neurons, and in cardiac, smooth, and skeletal muscle and other excitable cells. These channels are known to be involved in membrane excitability, muscle contraction, and cellular secretion, such as in exocytotic synaptic transmission (McCleskey, et al., 1987). In neuronal cells, voltage-gated calcium channels have been classified by their electrophysiological as well as by their biochemical (binding) properties.

Calcium channels are generally classified according to their electrophysiological properties as Low-voltage-activated (LVA) or High-voltage-activated (HVA) channels. HVA channels are currently known to comprise at least three groups of channels, known as L-, N- and P-type channels (Nowycky, et al., 1985; Sher, et al., 1991). These channels have been distinguished one from another structurally and electrophysiologically as well as biochemically on the basis of their pharmacology and ligand binding properties. Thus, dihydropyridines, diphenylalkylamines and piperidines bind to the $alpha_1$ subunit of the L-type calcium channel and block a proportion of HVA calcium currents in neuronal tissue, which are termed L-type calcium currents.

N- or omega-type HVA calcium channels are distinguishable from other calcium channels by their sensitivity to omega conotoxins (omega conopeptides). Such channels are insensitive to dihydropyridine compounds, such as L-type calcium channel blockers nimodipine and nifedipine (Sher, et al., 1991; Sher and Clementi, 1991).

A. Omega-Conopeptides

Omega-conopeptides are components of peptide toxins produced by marine snails of the genus Conus, and which act as calcium channel blockers (Gray, et al., 1988). About 500 species of cone snails in the Conus genus have been identified, and a variety of omega-conopeptides from several of these species have been isolated. The primary sequences of eight naturally-occurring omega-conopeptides are shown in FIG. 1, where SNX-231 is an alternative form of MVIIC/SNX-230. Conventional letter initials are used for the amino acid residues, and X represents 4-hydroxyproline, also abbreviated 4Hyp. All of the peptides shown in the figure are amidated at their C-termini.

The peptides shown in FIG. 1 are identified by names which are commonly associated with either the naturally occurring peptide (single letter followed by a Roman numeral followed by a single letter), and by a synthetic designation (SNX-plus numeral). Either or both of these designations will be used interchangeably throughout the specification. For example, the peptide whose sequence is designated MVIIA/SNX-111 will be referred to herein as OCT MVIIA, or alternatively, SNX-111, the latter to signify that the compound is synthetic in origin. Synthetic and naturally occurring peptides having the same sequence behave substantially identically in the assays and methods of treatment of the invention. The OCT MVIIA (SNX-111) and OCT GVIA (SNX-124) peptides also have the common names CmTx and CgTx, respectively. All of the omega-conopeptides have three disulfide linkages connecting cysteine residues 1 and 4, 2 and 5, and 3 and 6, as indicated for the MVIIA peptide in FIG. 2A. FIGS. 2A and 2B shows analogs or derivatives of natural OCT MVIIA, OCT TVIA, and OCT SVIB peptides which have been synthesized and tested in accordance with the invention. Standard single amino acid code letters are used in the figure; X=hydroxyproline; Nle=norleucine; Met(O)=sulfoxymethionine; $NH_2$ group at the C terminus indicates that the peptide is C-terminal amidated; G-OH indicates termination in an unmodified glycine residue.

B. Preparation of Omega Conopeptides

This section describes the synthesis, by solid phase methods, of several naturally occurring omega conotoxin (OCT) peptides and additional omega-conopeptides which are used in the present invention.

Omega-conopeptides, such as those shown in FIGS. 1 and 2, can be synthesized by conventional solid phase methods, such as have been described (Olivera, et al., 1984). Briefly, N-alpha-protected amino acid anhydrides are prepared in crystallized form or prepared freshly in solution and used for successive amino acid addition at the N-terminus. At each residue addition, the growing peptide (on a solid support) is acid treated to remove the N-alpha-protective group, washed several times to remove residual acid and to promote accessibility of the peptide terminus to the reaction medium. The peptide is then reacted with an activated N-protected amino acid symmetrical anhydride, and the solid support is washed. At each residue-addition step, the amino acid addition reaction may be repeated for a total of two or three separate addition reactions, to increase the percent of growing peptide molecules which are reacted. Typically, 1–2 reaction cycles are used for the first twelve residue additions, and 2–3 reaction cycles for the remaining residues.

After completing the growing peptide chains, the protected peptide resin is treated with liquid hydrofluoric acid to deblock and release the peptides from the support. For preparing an amidated peptide, the resin support used in the synthesis is selected to supply a C-terminal amide, after peptide cleavage from the resin. After removal of the hydrogen fluoride, the peptide is extracted into 1M acetic acid solution and lyophilized. The three disulfide linkages in the peptides may be formed by air oxidation in the presence of dithiothreitol (DTT) or optionally other thiol containing compounds (e.g., cysteine, glutathione), according to procedures detailed in Example 1.

The peptide can be isolated by an initial separation by gel filtration, to remove peptide dimers and higher molecular weight polymers, and also to remove undesired salts, such as guanidine hydrochloride, used in the oxidation reaction. The partially purified peptide is further purified by preparative HPLC chromatography, and the purity and identity of the peptide confirmed by amino acid composition analysis, mass spectrometry and by analytical HPLC in two different solvent systems.

C. Stable Omega-conopeptide Formulations

Dilute solutions of omega-conopeptides are generally unstable in solution, as evidenced by oxidation of methionine residues and reduction or loss of biological activity. In accordance with an important aspect of the present invention, it has been discovered that omega-conopeptides can be significantly stabilized in solution by preventing oxidation of methionine residues present in the peptide structure. In particular, SNX-111, which contains a methionine at position 12, is approximately 10-fold less potent in binding to omega-conopeptide MVIIA binding sites, when its methionine is present in the sulfoxy form.

Co-pending U.S. application U.S. Ser. No. 08/496,847 discloses that SNX-111 oxidation can be prevented by addition of lactate buffer to the composition. More particularly buffers containing 150 mM lactate buffer, pH 4–4.5 improve stability of the compound considerably. It is known that solutions of SNX-111 in which the peptide concentration is less than about 0.1 mg/ml oxidize rapidly when dissolved in water, saline, or any of a number of buffers used in the art of peptide chemistry. However, solutions of SNX-111 ranging from 0.01–0.1 mg/ml are stable at 45° C. for weeks, when stabilized with lactate (150 mM, pH 4–4.5). In addition, buffers containing 50 μg/ml methionine are also effective in stabilizing SNX-111. Here, either 150 mM lactate buffer or acidified saline (pH 4–4.5) can be used to buffer the solution.

This stabilization method and formulation are particularly useful in preventing oxidation of those compounds containing methionine residues. With reference to FIGS. 1 and 2, such compounds include SNX-111, SNX-178, SNX-190, SNX-191, SNX-193, SNX-194, SNX-197, SNX-198, SNX-199, SNX-200, SNX-202, SNX-207, SNX-236, SNX-237, SNX-239, SNX-240; however, it is appreciated that the formulation buffer conditions may be used with peptides that lack methionine, as well.

Formulations which incorporate the components or principles discussed above may be used in a number of pharmaceutical applications related to omega conopeptide administration. Solutions of peptides provided in vials may be stored under the acidic formulation conditions, prior to dilution into a pharmaceutical excipient suitable for parenteral administration. Solutions used for slow infusion may also be preserved in this manner. The solution may be administered directly or neutralized prior to administration, according to the particular route of administration in which the formulation is used. For example, approximately 10 μl of SNX-111 in lactate buffer (150 mM, pH 4–4.5) has been administered directly into rat spinal cords (intrathecally) without noticeable untoward effects. For administration to the bloodstream the acidified physiological saline formulation may prove preferable, or either preparation may be neutralized by dilution in a neutralizing physiological excipient, such as a phosphate buffered saline, just prior to administration.

D. In vitro Properties of N-type VSCC Blocking Compounds

This section describes some of the in vitro properties of N-type VSCC blocking compounds, as exemplified by a specific group of omega conopeptides, namely those omega conopeptides that, like omega conopeptide MVIIA, exhibit high affinity binding to the MVIIA (site 1) binding site and relatively low affinity binding to the SVIB (site 2) omega conopeptide binding site, as discussed below.

1. Calcium-Channel Antagonist Activity. Omega conotoxins bind to a specific population of binding sites, present mainly in neuronal tissue. Dihydropyridines and other L-type channel blockers do not displace omega conotoxin binding, nor do omega conotoxins displace binding of such L-channel specific ligands to L-type calcium channels. These observations indicate that L-type calcium channel blockers and N-type calcium channel blockers act at distinct channels. Unlike L-type calcium channels, N-type or "omega" HVA calcium channels are found predominantly, although not exclusively, in nervous tissue (Sher, et al., 1991).

Inhibition (blockade) of N-type HVA neuronal calcium channels can be conveniently measured in an isolated cell system, such as the mouse neuroblastoma cell line, strain N1E115 or the human neuroblastoma cell line IMR32, as described in U.S. Pat. No. 5,364,842, incorporated herein by reference. As demonstrated therein, N-type calcium currents are blocked by omega conopeptide MVIIA, but not by dihydropyridines.

Membrane currents are conveniently measured with the whole cell configuration of the patch clamp method, according to the procedure detailed in Example 2. Briefly, a voltage clamp protocol was performed in which the cell potential was stepped from the holding potential of about −100 mV to test potentials that ranged from −60 mV to +20 mV, and the cell was held at the holding potential for 5 seconds between pulses.

FIG. 3 shows a typical inward calcium current elicited by a voltage step from −80 mV to −20 mV in the absence of OCT. In this, and most of the recordings shown, barium (Ba) replaced calcium (Ca) as the charge-carrier through the calcium channels in order to increase the signal (McCleskey). According to the procedure described in Example 2, an N1E115 neuroblastoma cell was bathed in saline with sodium replaced by N-methyl-D-glucamine (NMDG), and 10 mM Ba instead of 2 mM Ca. These substitutions reduced the sodium current that would otherwise have contaminated the calcium current record, and increased the calcium current above what it would have been with only 2 mM Ca in the bath. Potassium currents were blocked by tetraethylammonium (TEA) in the bath and cesium (Cs) in the pipet solution.

As seen from FIG. 3, curve a, the calcium current activates quickly (within about 20 ms) and inactivates with a time constant of 30 to 40 ms. The calcium current is measured by the amplitude of the peak inward current elicited by the depolarization peak, and has a measured value of about −1200 pA. The cell in FIG. 3 (curve a) was also exposed to 1 μM nifedipine, a dihydropyridine, which is expected to effectively block L-type calcium channels in the neuroblastoma cells, and no effect on the measured calcium current was observed. The calcium current observed is thus not dihydropyridine-sensitive.

2. Specific, High Affinity Binding to OCT Receptors. Omega-conopeptides have been shown, in accordance with the invention, to bind with high affinity to specific binding site(s) in neuronal cells. In accordance with the selectivity of the compound, the binding affinity can be characterized either by the binding constant of the compound for the high-affinity MVIIA (SNX-111) binding site, also referred to as "site 1" herein, or the binding constant of the compound for the high-affinity SVIB (SNX-183) or the MVIIC (SNX-230) binding site, also referred to as "site 2" herein. Characteristics of these two distinct OCT binding sites are summarized below. In some cases, it is useful to characterize omega-conopeptides according to the ratio of their binding constants measured for binding to neuronal-cell MVIIA (SNX-111)-specific binding site 1 and SVIB (SNX-183)- or MVIIC (SNX-230)-specific binding site 2.

Binding to the OCT MVIIA binding site in neuronal tissue can be demonstrated in a variety of cell types and synaptosomal cell fractions. One preferred synaptosomal fraction is a mammalian brain synaptosomal membrane preparation, such as the rat brain synaptosome preparation described in U.S. Pat. No. 5,364,842 and Example 3 herein. The binding constant of a compound for the MVIIA binding site is typically determined by competitive displacement of radiolabeled OCT MVIIA (SNX-111) from the synaptosomal preparation, as follows.

The binding constant ($K_d$) of the MVIIA (SNX-111) peptide for the synaptosomal membranes is determined by a saturation binding method in which increasing quantities of radiolabeled peptide are added to the synaptosomal membranes, and the amount of labeled material bound at each concentration is determined (Example 3B). The appropriate binding equation describing the concentration of bound ligand as a function of the total ligand in equilibrium is fitted to the data to calculate the $B_{max}$ (the concentration of binding sites on the synaptosomes), and the $K_d$ (which is approximately the concentration of the ligand required for half saturation of binding sites).

Using conventional Scatchard analysis, a $K_d$ binding value of approximately 10 pM has been obtained for binding of omega conopeptide MVIIA to rat synaptosomal membranes. Similarly $K_d$'s were determined for binding of radiolabelled SVIB (SNX-183) and MVIIC (SNX-230) to binding sites in synaptosomal membranes.

Figure 4A:
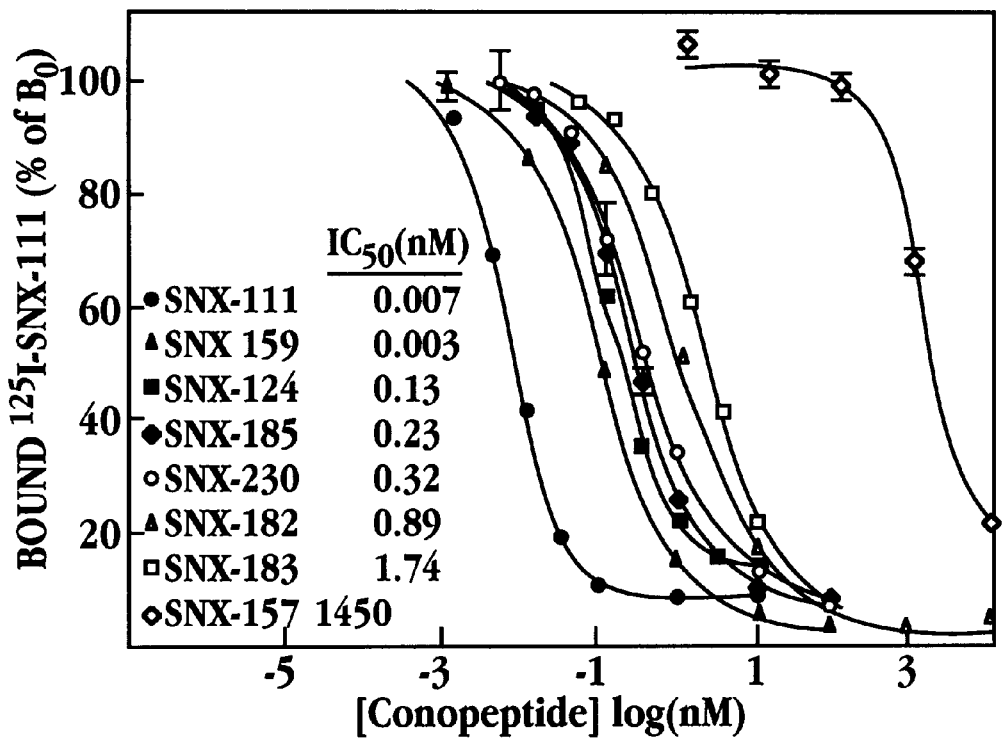
FIGS. 4A and 4B show computer-fit competitive binding curves for omega-conopeptide binding to the OCT MVIIA (SNX-111) binding site in rat brain synaptosomes.
Figure 4B:
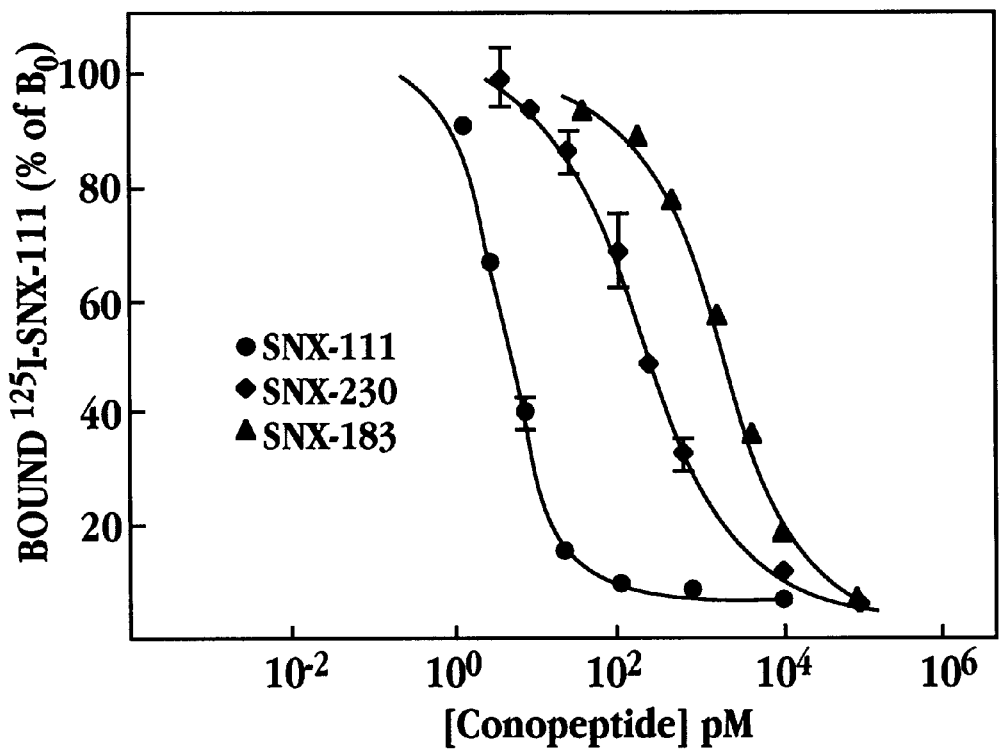

To determine the binding constant of a test N-type VSCC blocking compound for an OCT binding site, the test compound is added, at increasing concentrations, to a membrane preparation, such as a synaptosome preparation, in the presence of a standard concentration of a radiolabeled OCT which exhibits reversible binding, such as OCT MVIIA (SNX-111). The synaptosomal material is then rapidly filtered, washed and assayed for bound radiolabel. The binding constant ($K_i$) of the test compound is determined from computer-fit competitive binding curves, such as shown in FIGS. 4A and 4B for MVIIA (SNX-111) peptide, to determine first the $IC_{50}$ value of the compound, i.e., the concentration which gives 50% displacement of labeled MVIIA peptide. A $K_i$ is determined according to standard methods from the $K_d$ value of OCT MVIIA and the $IC_{50}$ value of the compound, as detailed in Example 3. A relative potency value can also be calculated from this information, as illustrated. Like the $K_i$ value, this value allows comparisons between assays performed under slightly differing conditions or at different times. While the specific value for a particular compound may vary from preparation to preparation, the rank order of binding affinities among the compounds should remain essentially unchanged. Thus the potency of a particular compound can be compared to standard compounds within a given preparation, to determine whether the test compound within a potency range considered useful in the methods of the invention, as discussed below.

Calculated $IC_{50}$ values for a number of omega-conopeptides for binding of OCT MVIIA (SNX-111) to a rat synaptosomal preparation are given in Table 1. The compounds are arranged in order of increasing $IC_{50}$ values.

TABLE 1

COMPETITION OF $^{125}$I-MVIIA (SNX-111)
BINDING BY OCT PEPTIDES

|  | $IC_{50}$ (nM) |
|---|---|
| SNX-207 | .007 |
| SNX-194 | .008 |
| SNX-195 | .009 |
| MVIIA (SNX-111) | .010 |
| SNX-190 | .021 |
| SNX-236 | .030 |
| SNX-200 | .039 |
| SNX-201 | .046 |
| SNX-202 | .046 |
| SNX-193 | .070 |
| SNX-194 | .090 |
| SNX-239 | .090 |
| MVIIC (SNX-230) | .32 |
| MVIIB (SNX-159) | .101 |
| GVIA (SNX-124) | .134 |
| SNX-198 | .160 |
| SNX-191 | .165 |
| TVIA (SNX-185) | .228 |
| SNX-196 | .426 |
| RVIA (SNX-182) | .893 |
| SVIB (SNX-183) | 1.5 |
| GVIIA (SNX-178) | 3.70 |
| SNX-197 | 11.3 |
| SVIA (SNX-157) | 1460. |

Figure 5A:
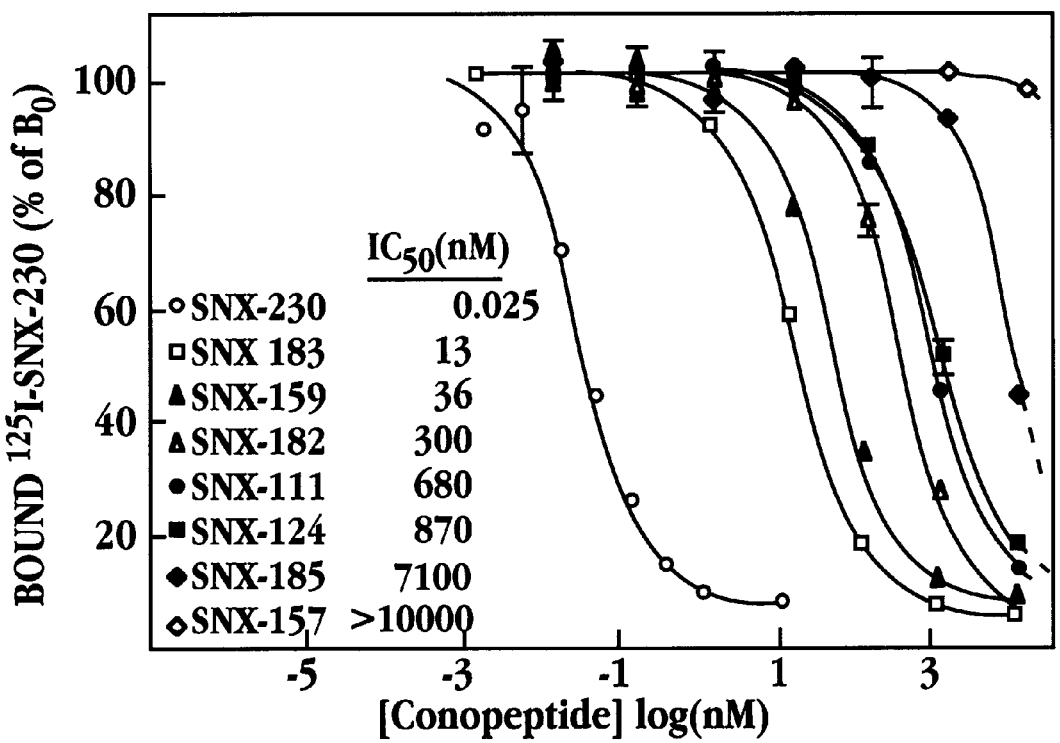
FIGS. 5A and 5B show computer-fit competitive binding curves for omega-conopeptide binding to the OCT MVIIC (SNX-230) binding site in rat brain synaptosomes.
Figure 5B:
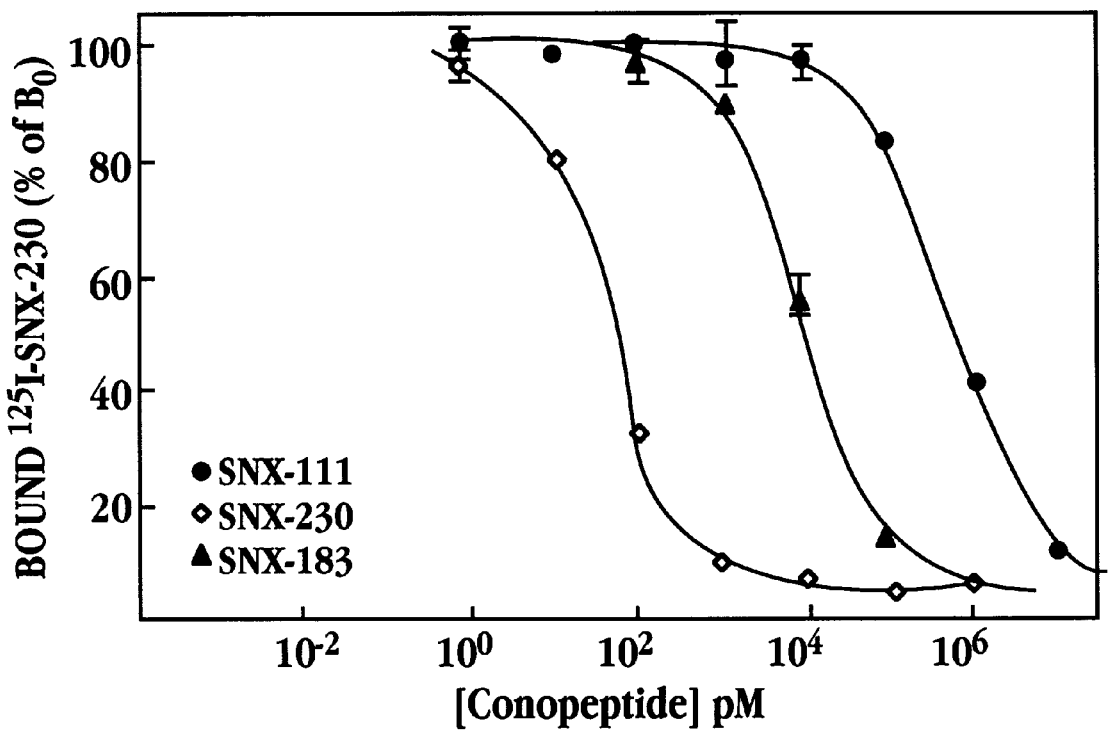

Similarly, $IC_{50}$ and $K_i$ values for compound binding to the SVIB (SNX-183) binding site can be calculated, as above, by determining the $K_d$ of labeled OCT SVIB (SNX-183) or OCT MVIIC (SNX-230) binding to a synaptosome preparation, then using competitive displacement of the labeled compound by the test compound, to determine the $IC_{50}$ and $K_i$ or relative potency values of the test compound. FIGS. 5A and 5B show computer-fit competitive binding curves for several omega-conopeptides whose binding to the SVIB (SNX-183) and/or MVIIC (SNX-230) binding sites was examined. From these curves, $IC_{50}$ values were determined as above.

Tables 2 and 3 list the relative potencies for binding of various omega-conopeptides to the site 1 and site 2 binding sites, and show the ratio of $K_i$ or $IC_{50}$ values determined for binding of each compound to the sites.

TABLE 2

SELECTIVITY OF CONOPEPTIDES FOR SITE 1 AND SITE 2

| Compound | Ki (nM) for competition[a] with: | | Selectivity[b] for: | |
|---|---|---|---|---|
| | [$^{125}$I]-SNX-111 | [$^{125}$I]-SNX-230 | site 1 | site 2 |
| SNX-111 | 0.002 | 150 | 75,000 : 1 | |
| SNX-183 | 0.43 | 6 | 14 : 1 | |
| SNX-230 | 0.20 | 0.03 | 1 : 7 | |

[a]Ki values were derived from analysis of competitive binding performed as described in Figure 1.
[b]Selectivity is expressed as the ratio of the Ki value determined for competition with high-affinity [$^{125}$I]-SNX-230 binding divided by the Ki value for competition with [$^{125}$I]-SNX-111 binding.

TABLE 3

SELECTIVITY OF CONOPEPTIDES FOR SITE 1 AND SITE 2

| Compound | IC$_{50}$ (nM) for competition with: | | Selectivity[a] for: | |
|---|---|---|---|---|
| | [$^{125}$I]-SNX-111 | [$^{125}$I]-SNX-230 | site 1 | site 2 |
| SNX-199 | 0.09 | 5,000 | 56,000 : 1 | |
| SNX-236 | 0.03 | 1,500 | 50,000 : 1 | |
| SNX-239 | 0.09 | 10,000 | 111,000 : 7 | |

[a]Selectivity is expressed as the ratio of the IC$_{50}$ value determined for competition with [$^{125}$I]-SNX-230 binding divided by the IC$_{50}$ value for competition with [$^{125}$I]-SNX-111 binding.

3. Binding of Omega conopeptides to Spinal Meningeal Membranes. Example 4 details experiments carried out in support of the present invention from which it has been determined that spinal meningeal membranes possess specific, relatively low affinity binding sites for omega conopeptides. Without ascribing to a particular theory, discovery of such binding sites is consistent with the important observation that these compounds pass across the spinal meningeal membranes at a higher rate and/or in a higher amount than would be expected if passive transport alone were responsible for the transmeningeal passage.

Figure 6:
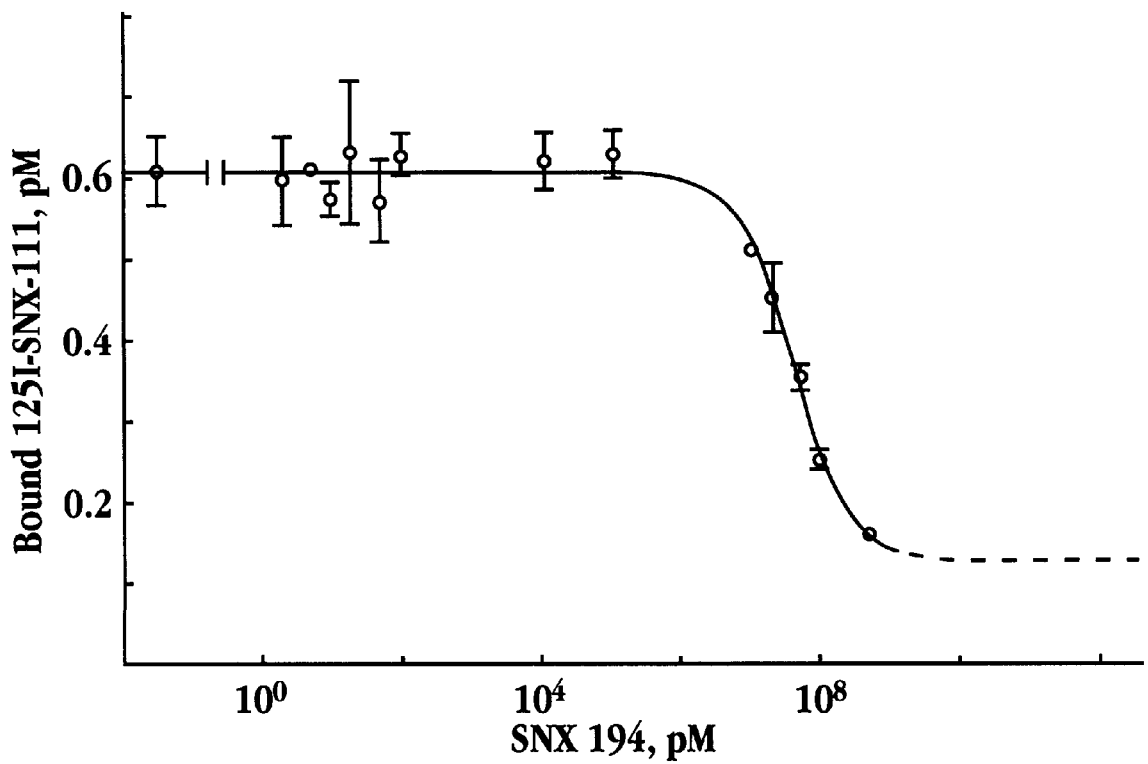
FIG. 6 shows a plot of displacement of [$^{125}$I]SNX-111 binding to monkey via arachnoid matter homogenates by [Nle$^{12}$] SNX-111.

FIG. 6 shows the results of experiments in which binding of $^{125}$I-SNX-111 to pia arachnoid membrane homogenates was competitively displaced by unlabeled [N1e$_{12}$] SNX-111. The competition binding curve shows low non-specific binding (approximately 20%), and a Hill coefficient close to one, consistent with binding to a single low-affinity site. The calculated IC$_{50}$ value is 41 μM.

4. Selective Inhibition of Neurotransmitter Release. Omega-conopeptides inhibit neurotransmitter release in various regions of the nervous system. As shown below, such inhibition varies according to the neurotransmitter, the omega-conopeptide, and the region studied. Neurotransmitters which can be measured, in accordance with various aspects of the invention, include, but are not limited to dopamine, norepinephrine, acetylcholine, GABA, glutamate, and a number of peptide neurotransmitters, such as calcitonin gene-related peptide (McGeer, et al., 1987).

Quantitation of release and inhibition thereof is determined by sensitive detection methods, also known in the art, including direct detection of release of endogenous stores by HPLC or specific radioimmunoassay (RIA), and detection of release of pre-loaded, labeled compound. Alternatively, or in addition, detection of release may be achieved using a number of indirect assays, exemplified by the electrophysiological studies described above, in which whole tissue response to electrical or chemical stimulation is measured.

Inhibition of release of the neurotransmitter norepinephrine from neuronal cells can be assayed in a number of systems known in the art, and, particularly, in mammalian brain hippocampal slices by standard methods, such as detailed in U.S. Pat. No. 5,364,842 and in Example 5A herein.

Table 4 shows IC$_{50}$ values for a variety of omega-conopeptides for inhibition of norepinephrine release. These values represent average IC$_{50}$ values calculated from thin (200μ) and thick (400μ) hippocampal slices. The three lowest IC$_{50}$ values, between 0.8 and 2.4 nM, correspond to omega-conopeptides which are most potent in this assay. It is noted that SNX-230 also inhibits release completely, but in a biphasic manner, inhibiting approximately 50% with high potency (IC$_{50}$=0.02 nM) and 50% with much lower potency (IC$_{50}$=65 nM). These results suggest that such norepinephrine release is mediated by at least two distinct subtypes of presynaptic calcium channels, one of which corresponds to the site 1 receptor identified by high affinity for SNX-111 and the other to the site 2 receptor recognized preferentially by SNX-230.

TABLE 4

INHIBITION OF NOREPINEPHRINE RELEASE BY OMEGA-CONOPEPTIDES

| Omega-Conopeptides | IC$_{50}$ (nM) |
|---|---|
| GVIA (SNX-124) | 0.8 |
| MVIIA (SNX-111) | 1.5 |
| TVIA (SNX-185) | 2.4 |
| SNX-201 | 11 |
| SNX-195 | 11 |
| SNX-202 | 29 |
| SVIB (SNX-183) | 200 |
| SNX-191 | >100 |
| SVIA (SNX-157) | >4500 |
| SNX-230 | 0.2,65 |

Effects of omega-conopeptides were also compared to those of OCT GVIA and amiodipine, an L-channel blocker, on potassium-stimulated release of dopamine and acetylcholine from slices of rat brain (striatal region) as described in Example 5. Briefly, in these experiments, striatal slices from rat brain were preloaded with radiolabelled dopamine or choline, then perfused for 45 minutes with bathing media. Slices were subjected to an S1 stimulus, consisting of addition of 15 mM potassium chloride to the bathing medium for 1 minute. Total outflow of radiolabeled neurotransmitter in response to S1 was measured. Slices were then washed, exposed to test compound for 20 minutes, then subjected to an S2 stimulus, as above. Comparison of outflow of neurotransmitter in response to S2 to outflow in response to S1 is a measure of drug effects on the system. Results are given as percent inhibition of release in Tables 5 and 6 below.

TABLE 5

EFFECT OF OMEGA-CONOPEPTIDES AND AMINODIPINE ON [$^3$] DOPAMINE RELEASE FROM STRIATAL SLICES

| Compound | Concentration | % Inhibition |
|---|---|---|
| GVIA | 1 nM | 5 |
| | 10 nM | 52 |

TABLE 5-continued

EFFECT OF OMEGA-CONOPEPTIDES AND AMINODIPINE ON
[³] DOPAMINE RELEASE FROM STRIATAL SLICES

| Compound | Concentration | % Inhibition |
|---|---|---|
| MVIIA | 1 nM | 6 |
|  | 10 nM | 49 |
| Amiodipine | 1000 nM | 0 |

TABLE 6

EFFECT OF OMEGA-CONOPEPTIDES AND AMIODIPINE ON
[³] ACETYLCHOLINE RELEASE FROM STRIATAL SLICES

| Compound | Concentration | % Inhibition |
|---|---|---|
| GVIA | 3 nM | 50 |
| MVIIA | 5.5 nM | 50 |
| Amiodipine | 1000 nM | 0 |

Further means of measuring inhibition of neuronal transmitter release are isolated tissue assays, such as atrial strip, aorta, vas deferens and guinea pig ileum assays, in which the response to a stimulus, usually an electrical stimulus, is correlated to the amount of neurotransmitter released from neurons innervating the tissue (Kenakin, 1987). In the guinea pig ileum, inhibition of electrically stimulated contractions is correlated with inhibition of acetylcholine release, as demonstrated by the ability of cholinergic agonists to overcome such inhibition. Example 6 describes the preparation and assay in detail. Table 7 shows the $IC_{50}$ values for various omega-conopeptides on contraction of guinea pig ileum in response to electrical stimulation.

TABLE 7

EFFECTS OF CONOPEPTIDES ON ELECTRICALLY
STIMULATED CONTRACTION OF GUINEA PIG ILEUM

| Compound | $IC_{50}$ (nM) |
|---|---|
| SNX-111 | 13 |
| SNX-185 | 29 |
| SNX-183 | 91 |
| SNX-157 | >100 |

II. Treatment of Pain

U.S. Pat. No. 5,364,842 describes analgesic properties of selected omega-conopeptides. This discovery was extended to include treatment of neuropathic pain as disclosed in U.S. patent application Ser. No. 08/049,794, filed Apr. 15, 1993, and incorporated herein by reference. Moreover, as disclosed in U.S. patent application Ser. No. 08/496,847, filed Jun. 27, 1995, progression of neuropathic pain can be retarded in a subject exhibiting early stage symptoms of neuropathic pain, particularly by providing localized delivery of N-type VSCC blocking compounds to the neuropathic site.

It is the discovery of the present invention that the above treatment methods can also be achieved by epidural administration of omega conopeptides, at doses not expected to produce sufficient intraspinal concentrations to effect analgesia. More specifically, according to this aspect of the invention, the analgesic conopeptide is effective when administered epidurally by a paradigm that results in prolonged contact of the compound with the epidural space, and more particularly with the spinal meninges. For example, such prolonged contact can be effected by continuous epidural infusion of the compound. Such administration is carried out at a dose that is much less than is predicted on the basis of the known physicochemical properties of the omega conopeptide compound. More specifically, the effective epidural dose is within the range of an effective intrathecal (intraspinal) dose of the same compound, given for approximately the same period of time.

Thus, according to the discovery that forms the basis for the present invention, such epidural administration of omega conopeptide produces an analgesic effect, even when no membrane permeation enhancing agents are added to the composition. This discovery was unexpected, in view of the known hydrophilic properties of omega conopeptides and the known permeability properties of the spinal meninges (dura mater, arachnoid mater, pia mater) that separate the epidural space from the spinal regions (e.g., dorsal horn synapses, cerebral spinal fluid) the compound presumably must contact to provide an analgesic effect (See, e.g., Gohil, et al., 1994; Miljanich and Ramachandran, 1995).

According to established principles, absent a specific transport mechanism, transmembrane diffusion of a compound across the spinal meningeal membranes is best correlated with its hydrophobicity. Molecular size and mass do not affect transmeningeal diffusion; however for drugs of intermediate lipid solubility (octanol:water partition coefficients <129–560), hydrophobicity is positively correlated with meningeal membrane diffusion, though in a nonlinear fashion (Bernards and Hill, 1992). Because SNX-111 is a hydrophilic peptide (octanol:water partition coefficient <0.0001; MW 2639), it would be expected to permeate meningeal membranes poorly and, therefore, have low analgesic potency when administered by the epidural route. If so, then comparatively high doses of SNX-111 would be required to achieve adequate analgesia, increasing the likelihood of sympatholysis (i.e., systemic hypotension) due to systemic uptake.

Figure 18:
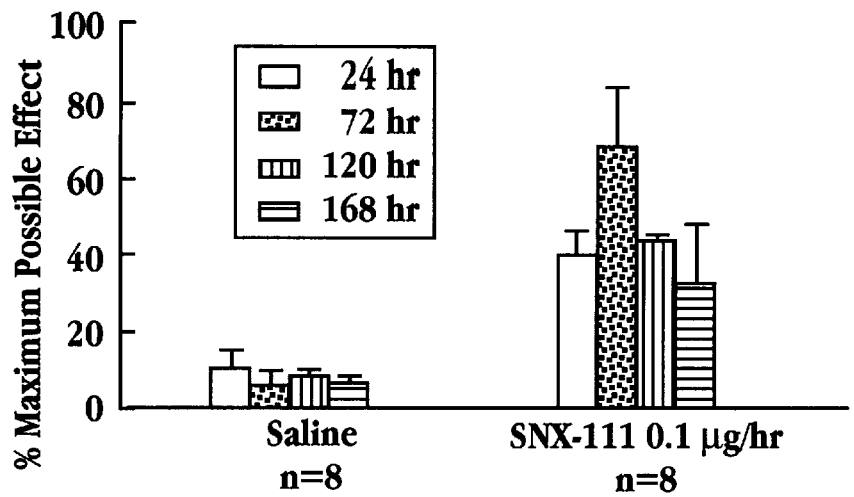
FIG. 18 shows histograms of thresholds of mechanical allodynia as % MPE after 24, 72, 120 or 168 hours of continuous intrathecal infusion of saline or 0.1 g/hour SNX-111.

In accord with the present invention, omega conopeptides having low octanol:water partition coefficients are effective analgesics when given in a dosage that is within the range of an effective intrathecal analgesic dose. In the context of the present invention, an effective analgesic dose is a dose that produces a significant analgesic response in a subject, as exemplified by a significant response in a standard experimental pain model. Thus, for rats subjected to the Chung allodynia model of neuropathic pain described herein, as discussed below, 2.4 micrograms of SNX-111 given intrathecally by continuous infusion over 24 hours produces a response of 40% MPE (FIG. 18). This represents a significant response in terms of pain relief to the subject. It is now apparent that approximately the same dose of SNX-111 given by epidural continuous infusion over 24 hours also produces significant analgesia (40% MPE; c.f., FIG. 19), in the absence of a membrane permeation enhancer and without producing significant hypotension.

Therefore, the present invention represents an improved method of delivering omega conopeptides to produce analgesia without significant side effect (hypotension).

As demonstrated above, the dose required is within the range of dose required for analgesia when the compound is given intrathecally; by "within the range" is meant that the dose should be within about ± an order of magnitude of the effective intrathecal dose, and more preferably within ±0.5 log units of the dose. Thus, in the example described above, where a total dose of 2.4 μg is effective intrathecally, the range for epidural administration will be from about 0.24–24 μg.

While it has been found that analgesia is produced by epidural administration when the drug is given by bolus injection, it is preferred that the compound be placed in prolonged contact with the epidural region, such as by continuous infusion. By prolonged contact is meant that a critical concentration of drug remain within the region for longer than occurs when a "bolus" injection is administered. Such prolonged contact can be effected by providing a depot formulation, such as a liposomal formulation, according to methods well known in the art, or by providing a continuous infusion of compound over such a prolonged period, as discussed above. In a preferred embodiment, the infusion will continue for at least 24 hours; however, this and dosage parameters will be adjustable according to the needs of the particular patient, within the framework of standard clinical protocols for regulating pain medication. With reference to the standard animal models presented herein, analogous dosages can be determined for humans or other species of interest, in accordance with standard pharmacokinetic principles.

As discussed above, in the context of the present invention, analgesic omega-conopeptides are those which are effective (a) to inhibit voltage-gated calcium channels selectively in neuronal tissue, as evidenced by the peptide's ability to inhibit electrically stimulated contraction of the guinea pig ileum, and (b) to bind to omega conopeptide MVIIA binding sites present in neuronal tissue. Such binding to omega conopeptide MVIIA binding sites (site 1, as described herein) is selective, as evidenced by relatively high binding affinity at such sites, as compared to binding at an omega conopeptide site 2 (described herein as a high affinity binding site for SNX-230 or SNX-183). Such selectivity can be measured by the selectivity ratio illustrated in Tables 2 and 3, above.

As discussed in the above-cited patents and patent applications, analgesic omega-conopeptides are effective as analgesic agents both in traditional opiate-sensitive models of nociceptive pain, such as the Rat Tail-Flick model or the rat formalin model, as well as in opiate-resistant models of pain, such as the allodynia model of neuropathic pain. These models, as well as results obtained using these models, are discussed below.

A. Analgesic Omega-Conopeptides

Omega-conopeptides useful in the present improved pain treatment method conform to certain physical and chemical constraints, as described below. Generally, omega-conopeptides useful in the treatment method are those which are 25–35 amino acids in length and which have three disulfide bonds at specified positions along their length. This section provides further guidance for selection of analgesic omega-conopeptides; however, it is appreciated that the guidelines provided below are subservient to the in vitro predictive assays described herein.

Based on a sequence homology analysis of the peptides whose full sequences are known (FIG. 7), the naturally occurring active omega-conopeptides may be grouped into distinct groups I and II, each with internal homologies distinct to that group, as can be appreciated from FIG. 7. Group I includes active omega-conopeptides MVIIA (SNX-111), MVIIB (SNX-159) and SNX-239, which possess binding constants to the MVIIA site within the range of compounds showing activity in treating pain. Group II includes TVIA (SNX-185), SNX-207 and SNX-236, which also possess binding constants in the range of compounds for analgesia. A third group includes inactive peptides SNX-231, and SVIA (SNX-157) and omega-conopeptides whose binding activities for the MVIIA site on neuronal membranes and/or activity in norepinephrine inhibition are outside the range of active compounds.

The three groups of omega-conopeptides are arranged in FIG. 7 with their six Cys residues aligned, which places these residues at positions 1, 8, 15, 16, 20, and 28. To make this alignment, gaps were introduced at the positions shown in the three groups. In the analysis below, these gaps retain the assigned number shown in FIG. 7, even though they represent amino acid deletions in the respective groups of active omega-conopeptides.

Sequence variation in the peptides, based on primary structure alone, was analyzed by adopting the following constraints:

1. The peptides in both active groups (I and II) include the Cys residues at position 1, 8, 15, 16, 20, and 28. Other Cys residues could be substituted at the positions indicated below only if they are selectively protected during oxidation of the peptide to form the three disulfide linkages.

2. The peptides in the active groups include three disulfide linkages connecting the Cys residues at positions 1 and 16, 8 and 20, and 15 and 28. As described above, the disulfide bridges are formed by air oxidation of the full sequence peptide in the presence of DTT. The ability of the peptide to form the three desired disulfide linkages would therefore require that the peptide, prior to disulfide bridging, be able to adopt a conformation which allows the three selected linkages, with or without the Cys protecting-group strategy discussed above. This constraint would thus exclude amino acid variations which prevent or otherwise hinder the formation of the three selected bridges.

Constraints 1 and 2 preserve the basic conformation of the omega-conopeptides imposed by the three disulfide bridges.

3. Within Group I, the amino acid variations which occur at the six non-conserved residues are allowed, including peptides in which the carboxy terminus is amidated or has a free acid form. That is, the first group compound derivatives include the peptide structures having the form: SEQ ID NO: 22-$X_1$-SEQ ID NO: 23-$X_2$-$X_3$-$X_4$-$X_5$-SEQ ID NO: 24-$X_6$-SEQ ID NO: 25-$X_7$-SEQ ID NO: 26-t, where $X_1$=K or S; $X_2$=S or H; $X_3$=R, L, or A; $X_4$=L or T; $X_5$=M or S; $X_6$=N or a deletion; SEQ ID NO 25 is R; $X_7$=S or deletion, and t=a carboxy or amidated carboxyterminal group, and where SEQ ID NO: 22 is CKGKGA; SEQ ID NO: 23 is C; SEQ ID NO: 24 is Y DCCTGSC; and SEQ ID NO: 26 is GKC.

4. Within Group II, the amino acid variations which occur at the eight non-conserved residues are allowed, including peptides in which the carboxy terminus is amidated or has a free acid form. Thus, the second group compound derivatives include the peptide structures having the form: SEQ ID NO: 27-$X_1X_2X_3$-SEQ ID NO: 28-$X_4$-SEQ ID NO: 31-t, where $X_1$=X or R; $X_2$=T or L; $X_3$=S or M, $X_4$=X or P; and t=a carboxy or amidated carboxyterminal group, and where SEQ ID NO: 27 is CLSXGSSCS; SEQ ID NO: 28 is YNCCRSCN; and SEQ ID NO: 31 is YSRKCR.

5. Considering both active groups together, amino acid positions which are conserved in all active species are preserved. Thus, for example, the Cys residues, the 5-position glycine, the 13-position tyrosine, the 19-position serine, and the 26-position lysine are all preserved. Preferred OCT analogs or derivatives may be selected by comparing, for purposes of inter-sequence conservation and substitution, those sequences known to be active. For example, in the case of the treatment of pain, omega-conopeptides MVIIA (SNX-111), SNX-239, SNX-199, TVIA (SNX-185) and SNX-236 are known active compounds. Active derivatives are those peptides having, in addition to the conserved cysteine residues described above, a conserved glycine residue at position 5, conserved serine residues at positions 9, 19, and 24, and a conserved lysine residue at position 26. Inter-sequence substitution of variable residues is then preferable in the formation of active analogs. For example, analog position 2 may be occupied by a lysine or a leucine residue, and position 6 may be occupied by an alanine or a serine residue.

6. Considering both active groups together, there are amino acid positions which are likely to be variable within the range of active species. For example, the position 2 amino acid may be lysine or leucine, the position-3 amino acid may be glycine or serine, and the position 4 amino acid, hydroxyproline or arginine. In addition, if the two or more amino acids at a variant position are in a common substitution class, substitution within that class may be favorable. Standard substitution classes are the six classes based on common side chain properties and highest frequency of substitution in homologous proteins in nature, as determined, for example, by a standard Dayhoff frequency exchange matrix (Dayhoff). These classes are Class I: Cys; Class II: Ser, Thr, Pro, Hyp, Ala, and Gly, representing small aliphatic side chains and OH-group side chains; Class III: Asn, Asp, Glu, and Gln, representing neutral and negatively charged side chains capable of forming hydrogen bonds; Class IV: His, Arg, and Lys, representing basic polar side chains; Class V: Ile, Val, and Leu, representing branched aliphatic side chains, and Met; and Class VI: Phe, Tyr, and Trp, representing aromatic side chains. In addition, each group may include related amino acid analogs, such as ornithine, homoarginine, N-methyl lysine, dimethyl lysine, or trimethyl-lysine in class IV, and a halogenated tyrosine in Group VI. Further, the classes may include both L and D stereoisomers, although L-amino acids are preferred for substitutions.

7. Considering the known inactive species, substitutions to amino acids which are present in inactive species, but not active ones, at any selected residue position, are not favored to preserve activity in the active compounds.

The above amino acid selection rules 6–7 are intended as a guide for allowed amino acid substitutions within active omega-conopeptides. Once an amino acid substitution or modification is made, the peptide is further screened for the requisite calcium channel antagonist activity, and the requisite activities for inhibition of neurotransmitter release and binding to the appropriate OCT binding site of neuronal membranes, as described above.

Omega-conopeptides which are selected on the basis of the foregoing criteria are tested for ability to produce analgesia in a standard test of analgesia, such as the Rat Tail-Flick test, wherein analgesia is measured by a prolongation of reaction time to a noxious radiant heat stimulus, or the Chung allodynia model of peripheral neuropathy, where analgesia is measured in terms of the level of painful stimulus that is tolerated by a sensitized animal.

B. In vitro Properties of Analgesic Omega-conopeptides

1. Calcium Channel Blocking Activity. Calcium channel blocking activity was measured electrophysiologically in neuronal (N1E-115 or IMR-32) cell lines, as described in Section I, above, and in detail in Example 2. Omega-conopeptides having calcium channel blocking activity are those which block calcium currents in such cell lines with potencies in the range observed for omega-conopeptides MVIIA and GVIA in N1E-115 cells.

2. High Affinity Binding to OCT Binding Sites. Methods for determination of binding affinity to high affinity OCT binding sites are discussed in Example 3, below.

Experiments testing reversibility of binding of SNX-111, SNX-183 and SNX-124 revealed that SNX-111 and SNX-183 exhibited dissociation half-times of two and five minutes, respectively. In contrast, SNX-124 did not dissociate appreciably from its binding site(s), even 1 hour following addition of excess unlabelled compound, indicating that SNX-124 binds irreversibly to its binding site in neuronal membranes.

Compounds were tested for their ability to displace binding of SNX-111, SNX-183, or SNX-230 from their respective binding sites (site 1 and site 2, as described above). In displacing SNX-111, it was found that compounds having analgesic activity, such as OCT MVIIA (SNX-111), SNX-239, SNX-236, SNX-199 SNX-159 and TVIA (SNX-185), have $IC_{50}$ values between about 15 and 300 pM, and $K_i$ values between about 1 and 100 pM. In contrast inactive compound SNX-183 had an $IC_{50}$ of greater than 1000 pM for binding at the MVIIA site.

From the foregoing, it is seen that active compounds in accordance with the invention are characterized by a high binding affinity for MVIIA binding site 1. The binding affinity for these sites may be characterized as follows. In the first approach, the binding affinity of the compound for binding site 1, as estimated by $IC_{50}$ in displacing MVIIA from the site, is compared directly with those of selected high affinity active compounds, such as SNX-111 and SNX-185. An active compound is one whose binding affinity is at least as high as and preferably within the range of binding affinities measured for such high affinity OCT's. Secondly, the binding affinity of the test compound can be characterized by binding to binding site 2, as estimated by $IC_{50}$ in displacing MVIIC (SNX-230) or SVIB (SNX-183) from the site. Thirdly, the binding affinity of the compound can be characterized by the ratio of binding constants or relative affinities of the compound for site 1 and site 2, as just described. Here an active compound is one whose binding ratio is within the range for the selected active peptides, such as MVIIA (SNX-111) and TVIA (SNX-185); i.e., the binding ratio is substantially within the range of the ratio observed for the omega-conopeptides MVIIA and TVIA. In this particular context the term "within the range" means that the test analgesic compound will have a binding ratio that is no higher than the highest nor lower than the lowest ratio measured for the standard reference compounds. Thus, if a test compound were measured in the same assays used to generate Table 3 above, it would be "within the range" of ratios measured for SNX-199, SNX-236 and SNX-239, if it had a site 1: site 2 selectivity ratio between 50,000:1 and 111,000:1.

A number of omega-conopeptide compounds which were tested gave $IC_{50}$ and $K_i$ values lower than or within the ranges of those of omega-conopeptides MVIIA (SNX-111) and TVIA (SNX-185) for binding at the SNX-111 site, as shown in Table 1, and these compounds should thus be considered candidates as analgesic compounds. In addition active compounds have relatively high selectivities of binding, equivalent or greater than those of MVIIA and TVIA. However, some of these compounds, may not fulfill additional criteria for analgesic compounds of the invention, as described herein.

3. Inhibition of Neurotransmitter Release. Another requisite property of analgesic omega conopeptides, in accordance with the invention, is their ability to specifically inhibit depolarization-evoked and calcium-dependent neurotransmitter release from neurons. For example, it is shown here that analgesic omega-conopeptides inhibit of electrically stimulated release of acetylcholine at the myenteric plexus of the guinea pig ileum (Example 6). This inhibition is associated anti-nociceptive activity, as seen in Table 7. Omega-conopeptides having analgesic activity have $IC_{50}$'s in the range of those values observed for active reference omega-conopeptides MVIIA (SNX-111) and TVIA (SNX-185), or less than approximately 50 nM, as observed in the assay shown.

C. In vivo Measurements of Analgesia

Analgesia is conveniently measured in one or more of a number of animal models, in which an animal's response to a given pain stimulus is measured.

1. Rat Tail-Flick Test. The rat tail-flick is a standard test in which latency of animal response to noxious stimulus (heat) is determined. This test is described in Example 7. Briefly, a rat is positioned such that its tail is exposed to a standard heat source, and the time that the animal voluntarily endures the heat, prior to moving its tail, is recorded. Analgesics, particularly opioid analgesics, prolong this time.

Figure 8:
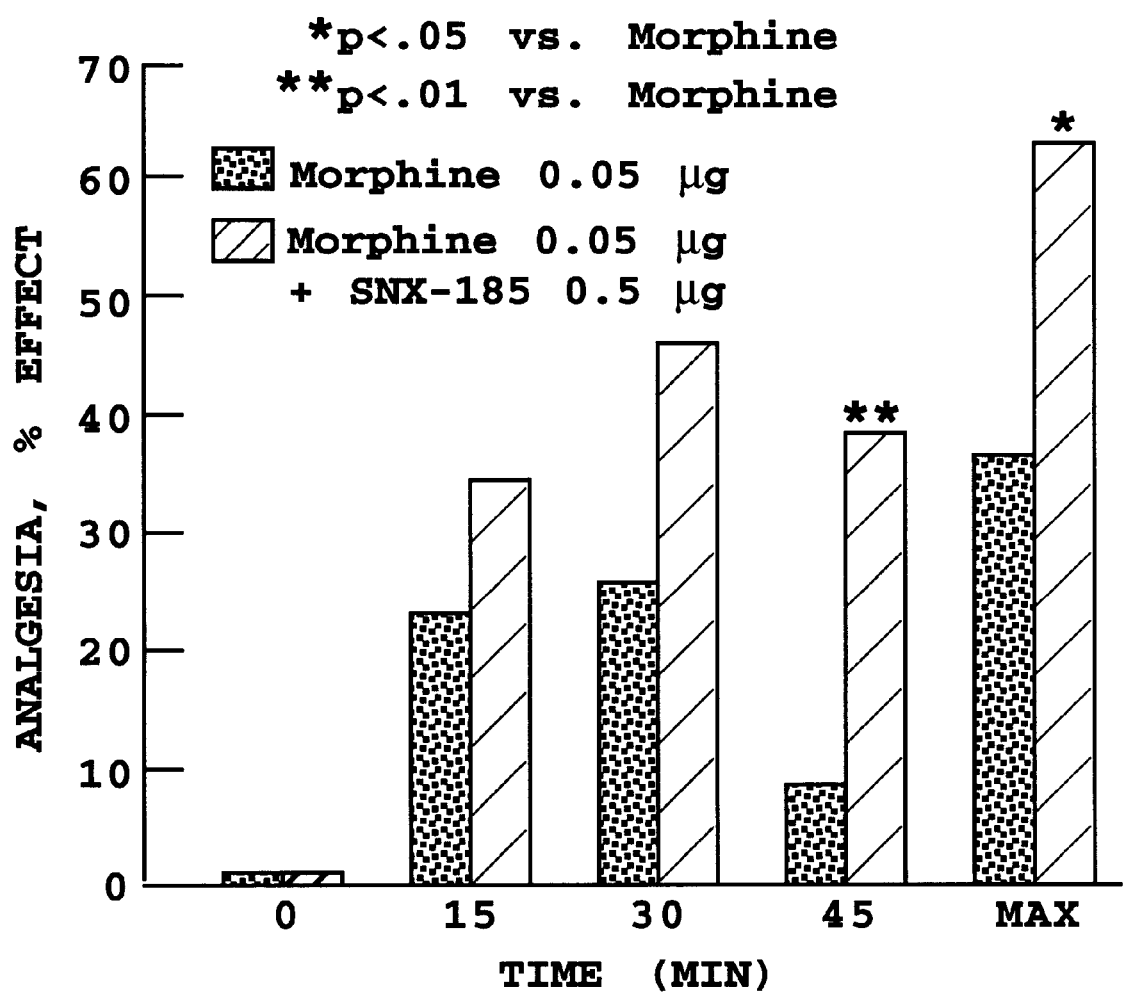
FIG. 8 shows the production of analgesia by a submaximal intrathecal dose of morphine (0.5 μg) administered alone (solid bars) and in the presence of 0.5 μg SNX-185 (hatched bars)
Figure 9A:
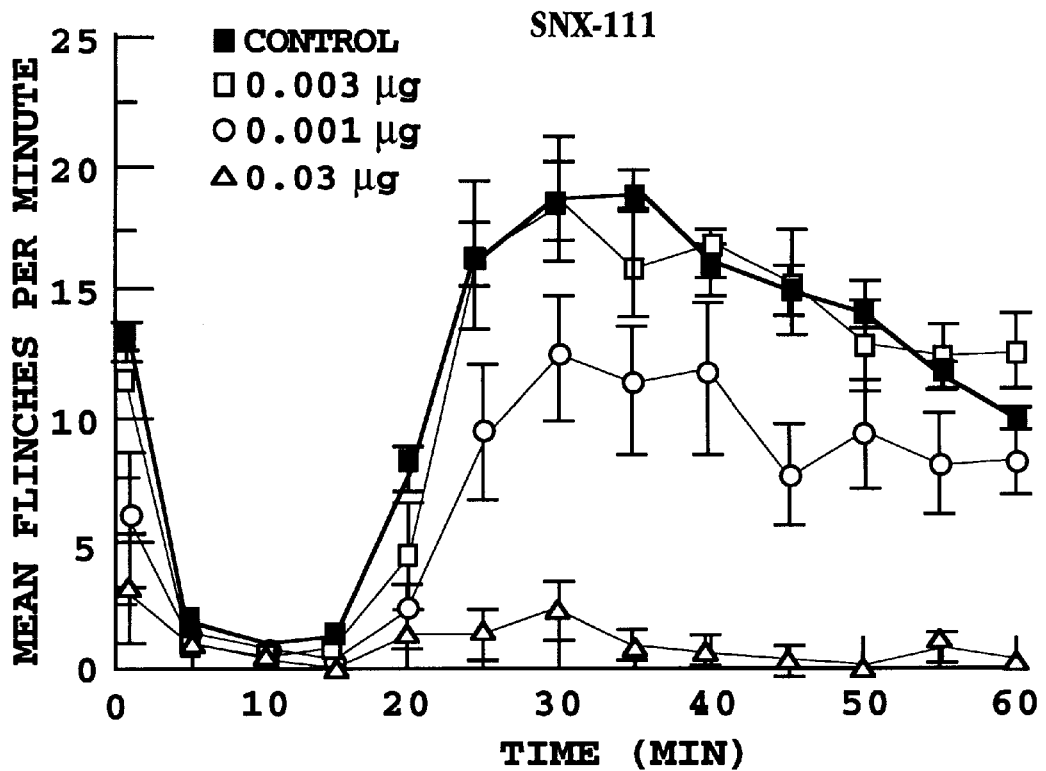
FIGS. 9A–9G show effects of varying doses of SNX-111 (A), SNX-185(B), SNX-159 (C), SNX-199 (D), SNX-239 (E), SNX-231(F), and SNX-236 (G) on flinch response in rat formalin tests.
Figure 9B:
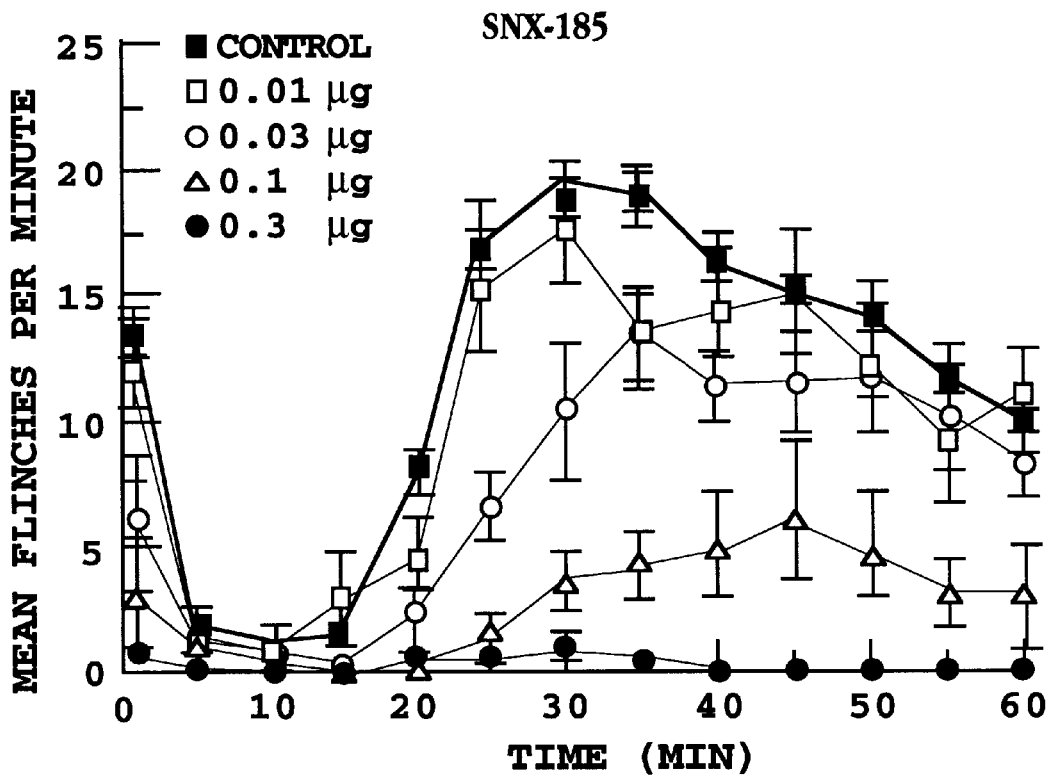
Figure 9C:
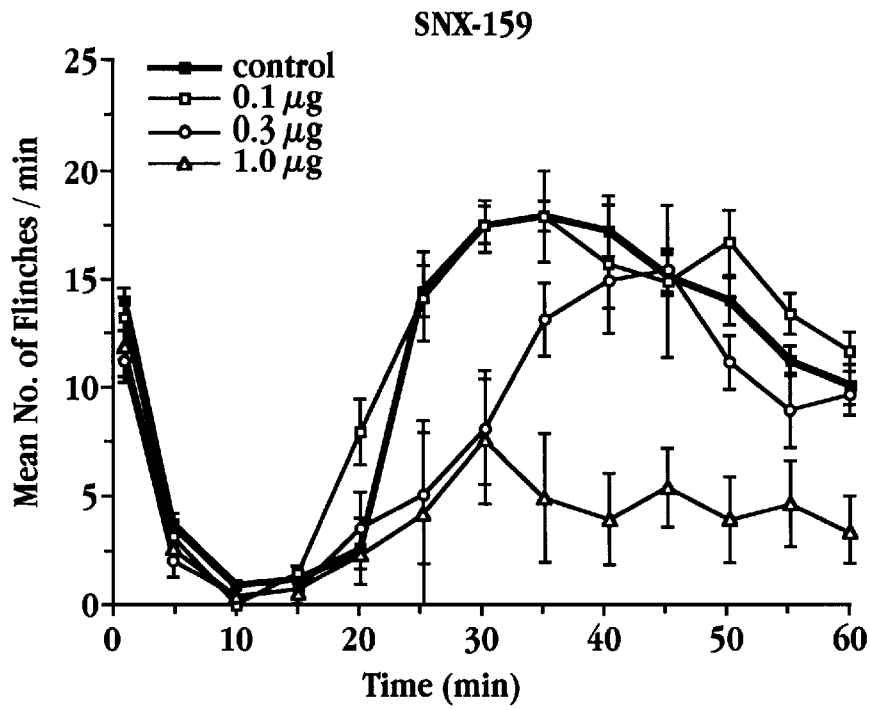
Figure 9D:
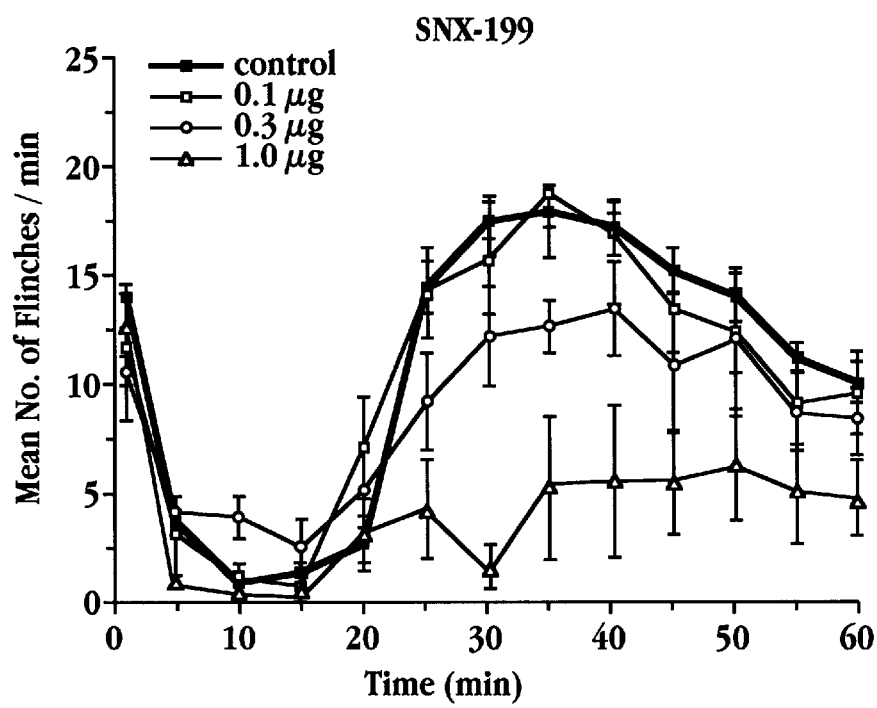
Figure 9E:
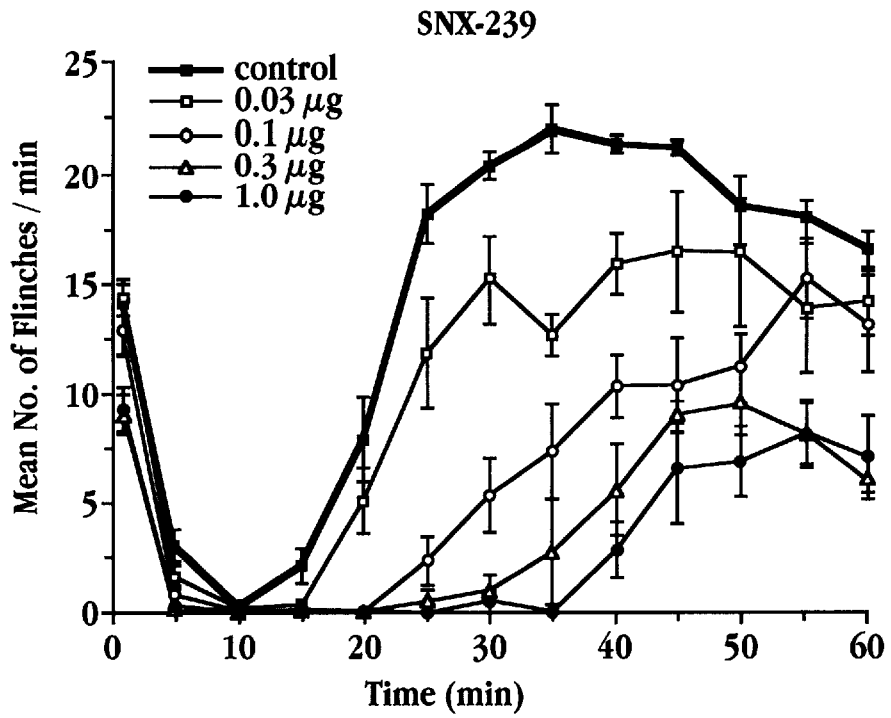
Figure 9F:
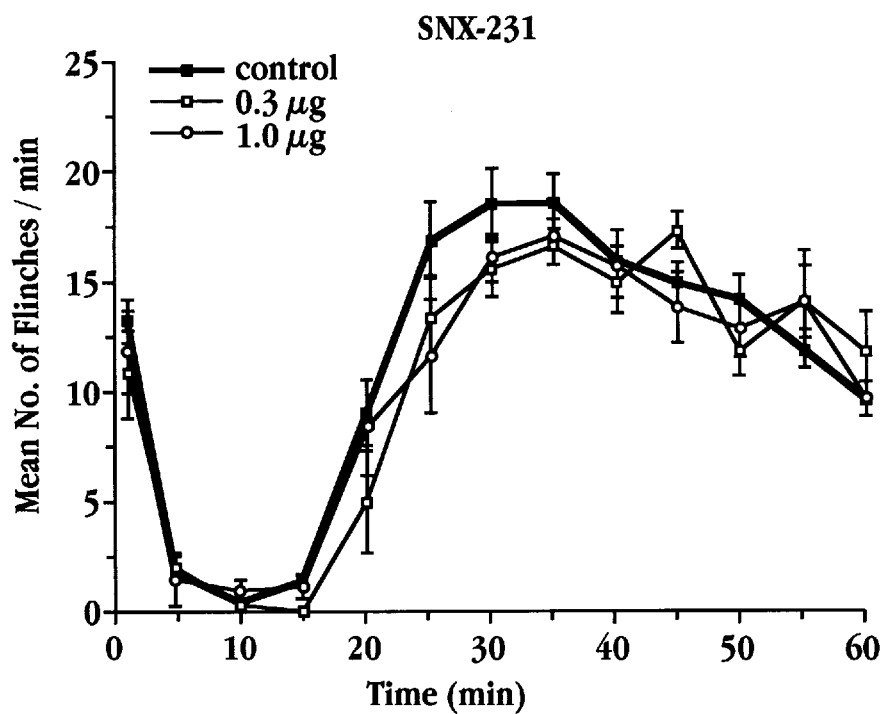
Figure 9G:
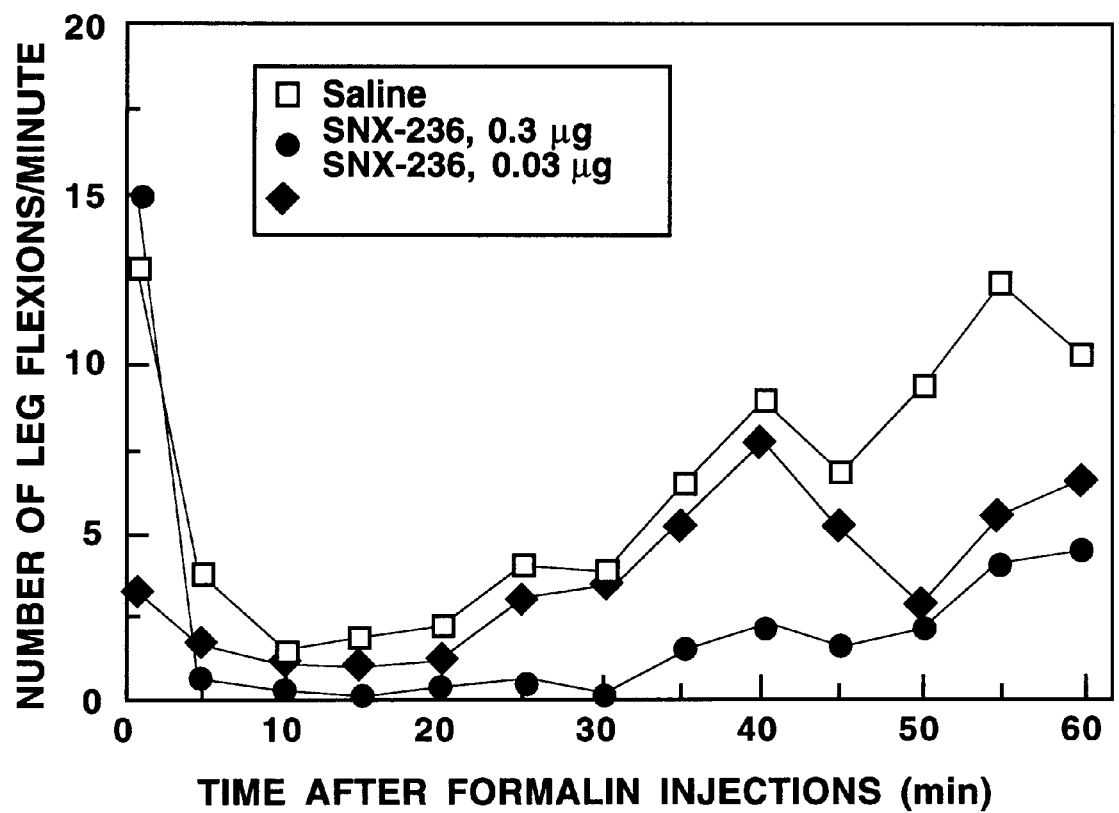

Shown in FIG. 8 are the results of experiments in which the effects of a sub-maximal dose of morphine were compared to those of the combination of a submaximal dose of morphine and a 0.5 μg (intrathecal) dose of SNX-185 in the Rat Tail-Flick Test. Intrathecal administration of SNX-185 enhanced the effects of a sub-maximal dose of morphine (FIG. 8) in this assay at all time points, and significantly at 45 min. after administration of compound.

2. Rat Formalin Test. The rat formalin test is another in vivo test of analgesic potency. This test reflects several levels of processing of nociceptive information in the spinal cord. Protracted sensory input generated by the noxious stimulus employed in this test (formalin in the paw) has been shown to induce an acute pain response phase (phase 1) followed by a second phase (phase 2). This second phase is thought to represent a state of facilitated processing evoked by the afferent input present during phase 1 and to involve release of at least two substances, glutamate and a tachykinin, based on other pharmacological evidence (Yamamoto and Yaksh, 1991, 1992).

In the rat formalin test, a standard dose of formalin is injected into the rat paw, and flexions of the paw are quantitated over the following 60 minute period (Example 8). A biphasic response pattern is typically observed, with numerous responses observed during the period 5 min. after injection (Phase 1) and a second phase (Phase 2) which occurs during the period about 10–60 minutes following injection, in which the mean number of flinches per minute is recorded as a function of time. This pattern is illustrated by the graphs shown in FIG. 9(A–G). Quantitation of responses during each phase is made by calculation of area under the curve of flinches/min. as described in Example 8.

FIG. 9(A–G) shows results of experiments in which varying doses of SNX-111, SNX-185, SNX-159, SNX-199, SNX-239, SNX-231 and SNX-236 were tested for effects on the formalin response in rats. FIG. 10 (A,B) shows dose-response curves generated from these data. SNX-111, SNX-185, SNX-236 and SNX-239 each exhibited potent and maximal inhibition of the Phase 2 response, while SNX-159 and SNX-199 were somewhat less potent in this regard. SNX-111 and SNX-185 likewise showed maximal inhibition of the phase 1 response, while SNX-239 produced less than 50% inhibition of Phase 1 response at the highest doses tested (0.3 and 1 Ag). SNX-231 was inactive in both Phase 1 and Phase 2 responses. From the dose response curves, $ED_{50}$ doses (doses which produced approximately 50% inhibition) were determined separately for Phase 1 and Phase 2 responses. These doses are summarized in Table 8.

TABLE 8

$ED_{50}$ FOR INTRATHECAL CONOPEPTIDES ON PHASE 1 AND PHASE 2 OF THE FORMALIN TEST

| | | $ED_{50}$ (μg, IT) ± 95% CI | |
|---|---|---|---|
| Drug | N† | Phase 1 | Phase 2 |
| SNX-111 | 21 | 0.011 (0.005–0.022) | 0.011 (0.007–0.015) |
| SNX-185 | 20 | 0.043 (0.030–0.061) | 0.041 (0.03–0.06) |
| SNX-239 | 12 | 0.54 (0.09–2.2)‡ | 0.052 (0.02–0.23) |
| SNX-159 | 12 | >1.0 μg | 0.47 (0.04–5.2) |
| SNX-199 | 12 | >1.0 μg | 0.76 (0.01–57) |
| SNX-231 | 12 | >1.0 μg | >1.0 |

†N = number of animals in the dose-responsive curve for calculation of $ED_{50}$.
‡$ED_{50}$ values were estimated from the 3 lower doses (0.03–0.3 μg) on the dose-responsive curve because the higher dose (1.0 μg) did not produce any additional effect (both 1.0 μg and 0.3 μg produced approximately a 50% reduction of the phase 1).

Figure 11:
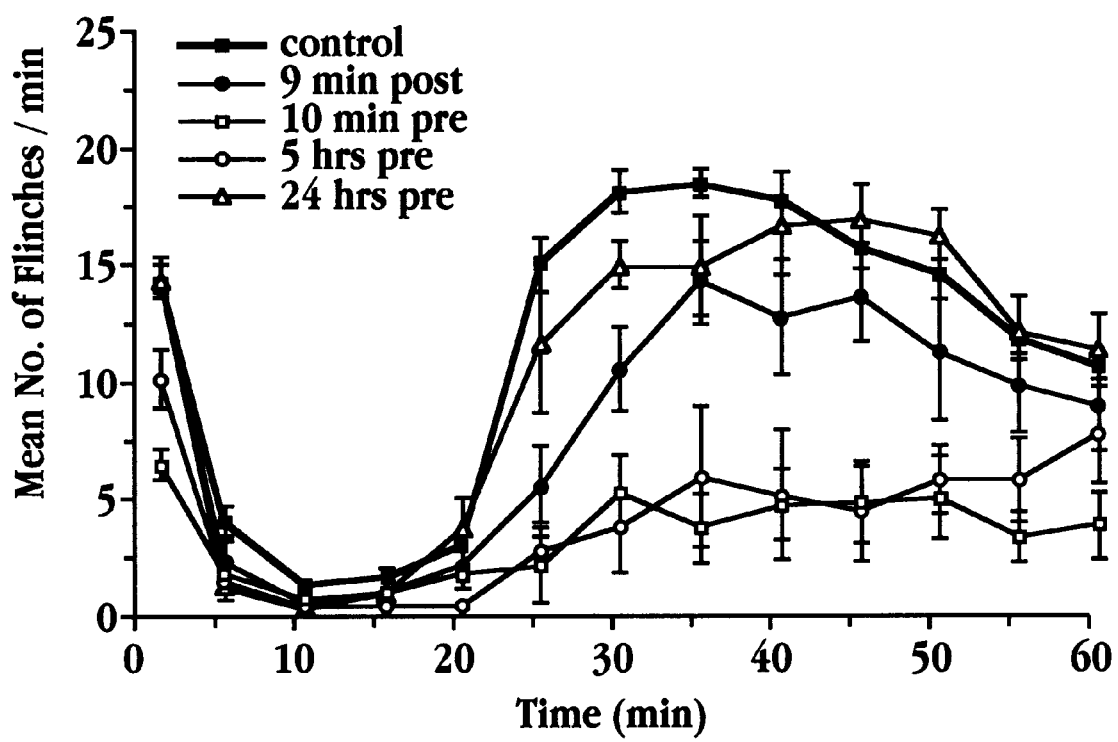
FIG. 11 shows time effect curves for effects of SNX-111 delivered 9 minutes after, or, 10 minutes, 5 hours, or 24 hours prior to injection of formalin in the formalin test.

FIG. 11 shows the results of studies in which time of administration of SNX-111 was tested. SNX-111 was administered 9 minutes after (closed squares), 10 minutes before (open squares), 5 hours before (open circles) or 24 hours before (open triangles) injection of formalin. Significant reduction in pain response was observed in all except the 24 hour pre-treatment paradigm.

Figure 12A:
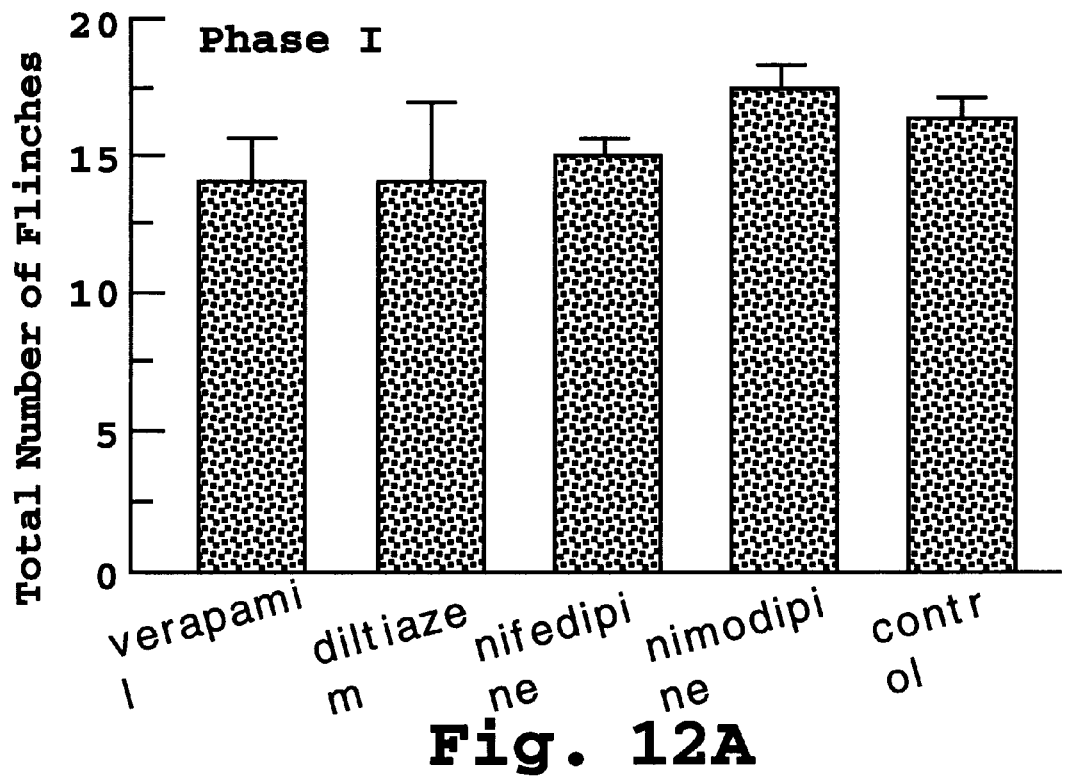
FIGS. 12A–12B shows the effects of L-type calcium channel blockers verapamil, diltiazem, nifedipine, and nimodipine on Phase 1 (FIG. 12A) and Phase 2 (FIG. 12B) in the rat formalin test.
Figure 12B:
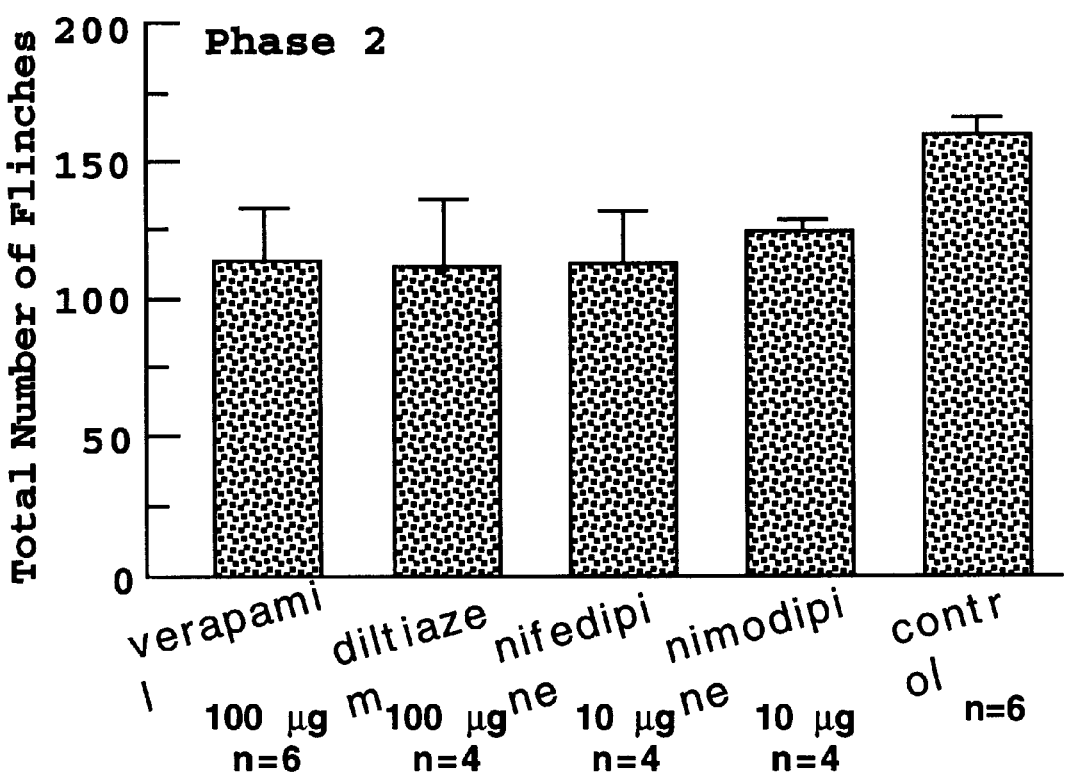

In separate studies, L-type calcium channel blocking dihydropyridine compounds nifedipine and nimodipine, as well as verapamil and diltiazem were without effect on Phase 1 and Phase 2 pain responses in the rat formalin test. The data for effects on Phase 1 and Phase 2 responses are summarized in FIGS. 12A–12B.

3. Neuropathic Pain Models. Analgesic potency of conopeptides is demonstrated in animal models of neuropathic or neurogenic pain. One such model resembles the human condition termed causalgia or reflex sympathetic dystrophy (RSD) secondary to injury of a peripheral nerve. This condition is characterized by hyperesthesia (enhanced sensitivity to a natural stimulus), hyperalgesia (abnormal sensitivity to pain), allodynia (widespread tenderness, characterized by hypersensitivity to tactile stimuli), and spontaneous burning pain. In humans, neuropathic pain tends to be chronic and may be debilitating. This type of pain is generally considered to be non-responsive or only partially responsive to conventional opioid analgesic regiments (Jadad). In accordance with the invention, analgesic omega conotoxin peptides are effective in providing relief of neuropathic pain, as described below.

Experiments carried out in support of the present invention were performed in a rat model of peripheral neuropathy detailed in Example 9. Briefly, in the model used, rats were subjected to a surgical procedure, described by Kim et al. and Bennett et al., designed to reproducibly injure peripheral nerves (spinal nerves L5 and L6). These rats developed a hyperesthetic state, which can be measured, using one or more paradigms known in the art. Here, allodynia was measured by stimulation of neuropathic rat hindlimb using wire hairs having graded degrees of stiffness. Analgesic compounds reverse the heightened sensitivity such animals exhibit to the stimulus.

FIG. 13 shows results in the allodynia model of peripheral neuropathy for animals treated with SNX-111 (13A), SNX- 239 (13B), SNX-159 (13C) and SNX-230 (13D). Data are expressed as percent maximum effect, where the maximum effect indicates a complete reversal of surgically induced allodynia, or relative insensitivity to stimulus (maximum equals 15 gram hair stimulus). A baseline of zero indicates a mean sensitivity to a wire hair graded at less than 3 grams. As shown in FIG. 13A, treatment of rats (n=6/treatment) with 1 or 3 µg SNX-111 resulted in elevation of threshold response. Peak elevation of response due to drug treatment (reversal of allodynia) was observed by 30–60 minutes, and effects lasted in excess of 60 minutes. SNX-239 showed significant analgesic effects at a dose as low as 0.33 µg, and evoked a prolonged analgesic response of at least 2 hours, as indicated. SNX-159 were also effective against neuropathic pain in this test at submicromolar doses (FIG. 13C), while SNX-230 was ineffective at such doses (FIG. 13D).

Figure 13A:
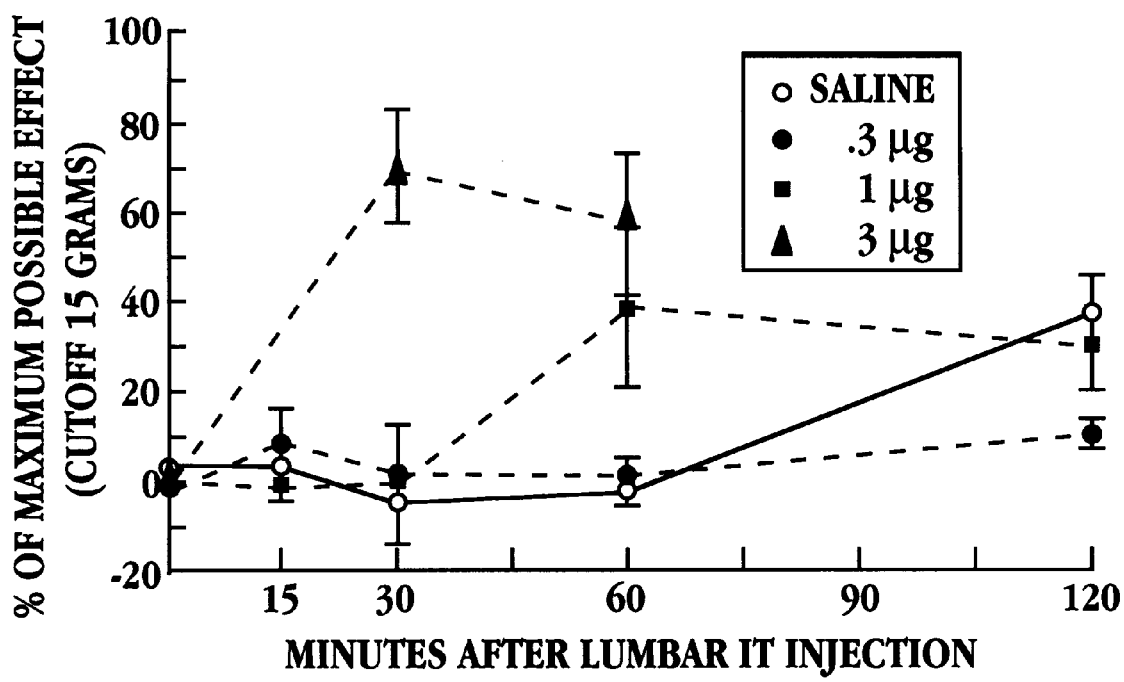
FIGS. 13A–13D show the effect of intrathecal treatment with various omega-conopeptides on mechanical allodynia thresholds in rats with a painful peripheral neuropathy, where SNX-111 (13A), SNX-239 (13B), SNX-159 (13C) and SNX-230 (13D) were tested at the doses indicated.
Figure 13B:
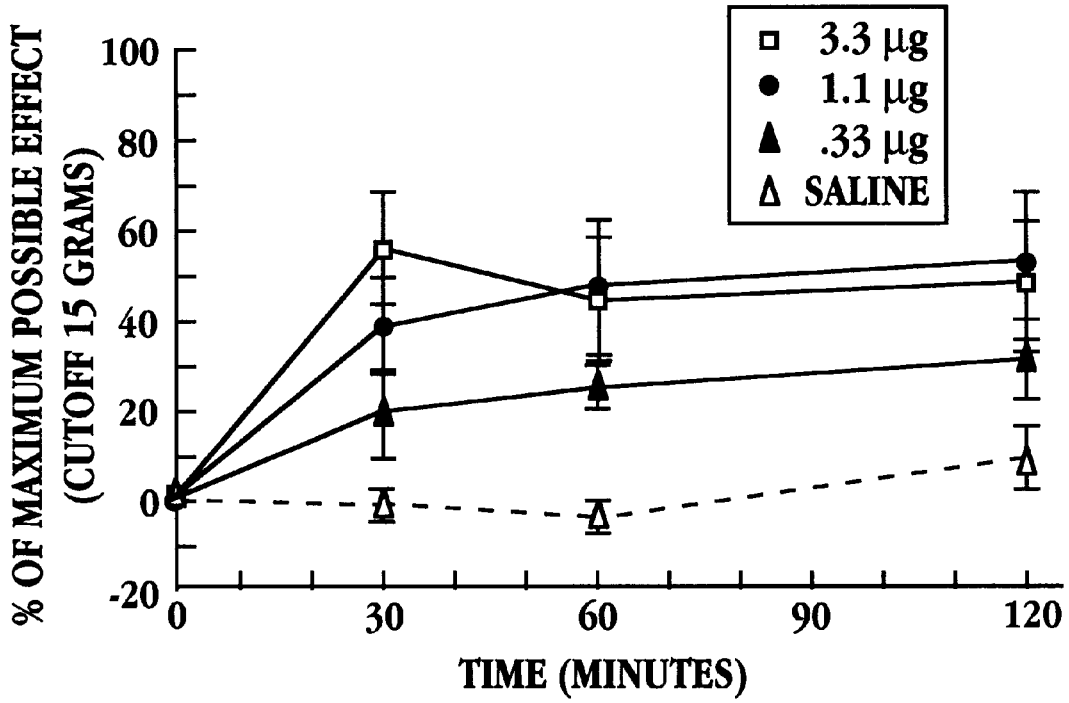
Figure 13C:
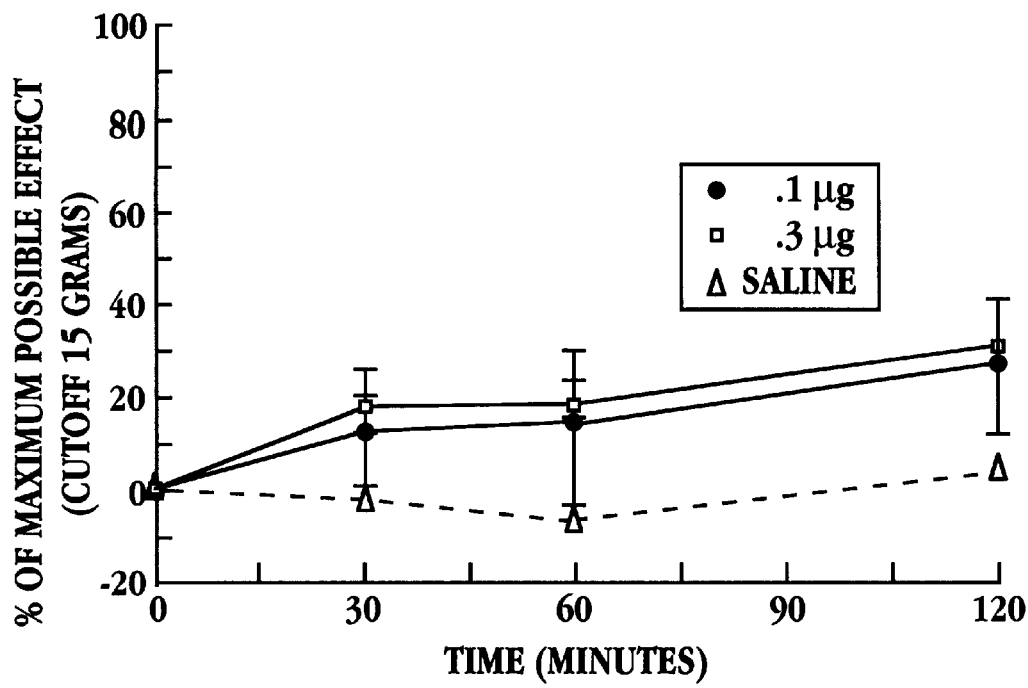
Figure 13D:
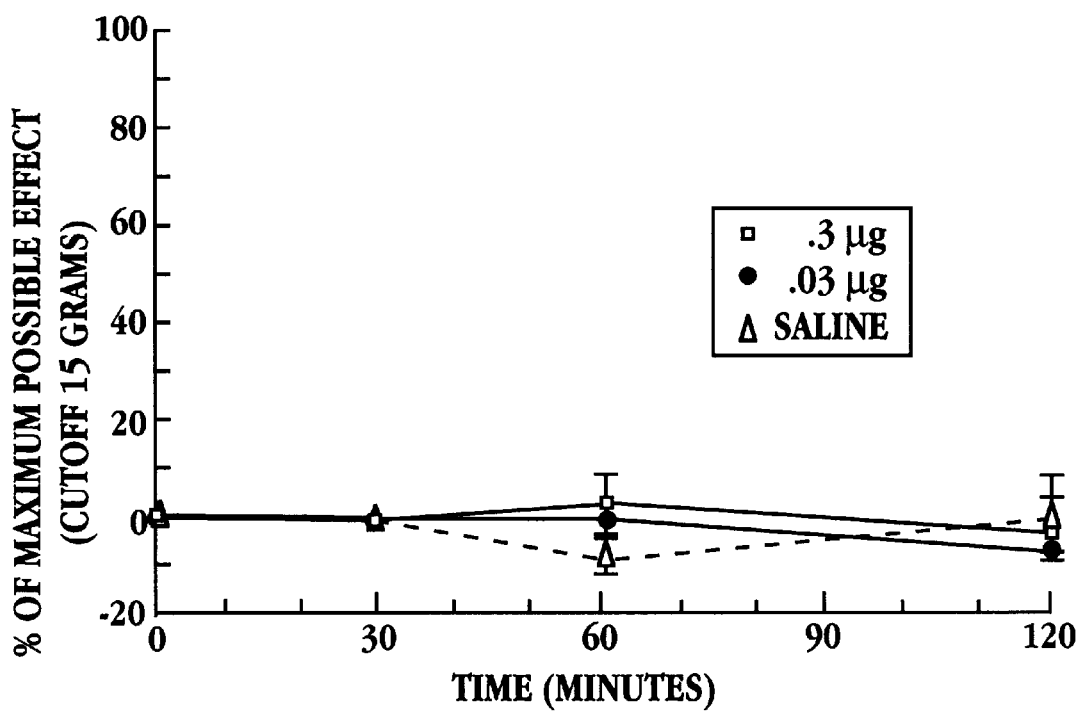
Figure 14A:
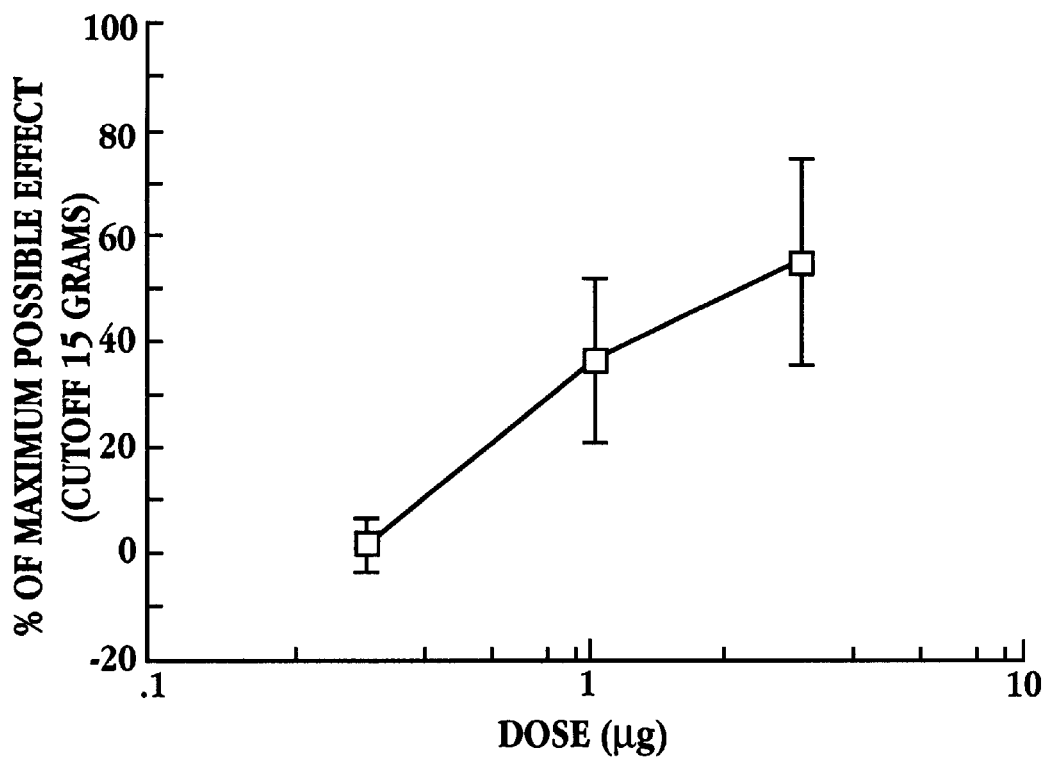
FIGS. 14A and 14B show dose response curves of effects of omega-conopeptides SNX-111 (14A) and SNX-239 (14B) derived from the data illustrated in FIGS. 13A and 13B, respectively, in a rat model of neuropathic pain.
Figure 14B:
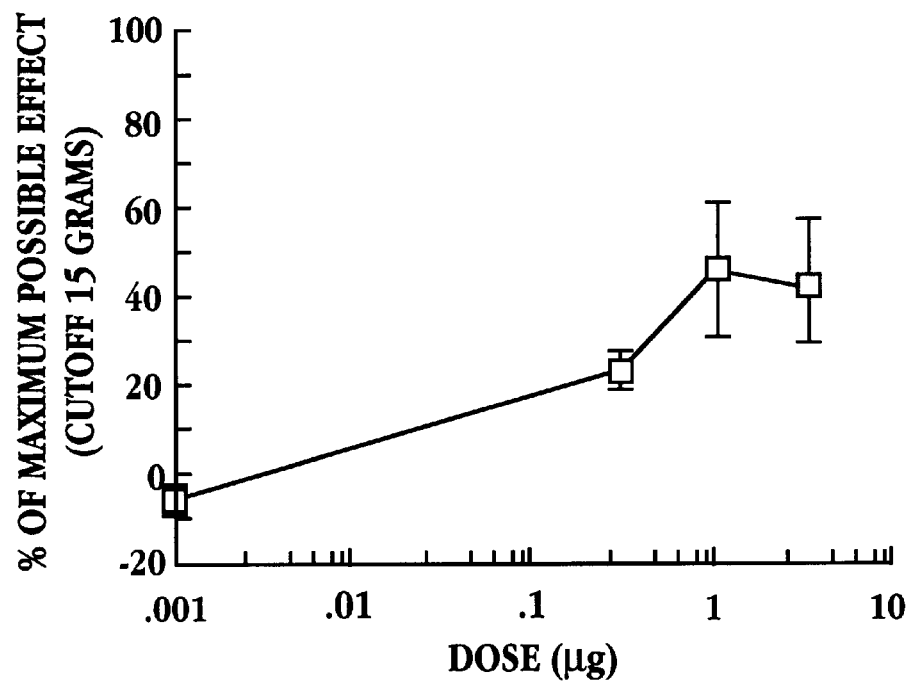

FIGS. 14A and 14B show dose response curves derived from the data shown in FIGS. 13A and 13B. These results indicate that analgesic omega conotoxin peptides, exemplified by SNX-111, are capable of reversing the hyperesthetic effects induced by nerve damage.

D. Epidural Administration of Omega Conopeptides for Treatment of Pain

Figure 17A:
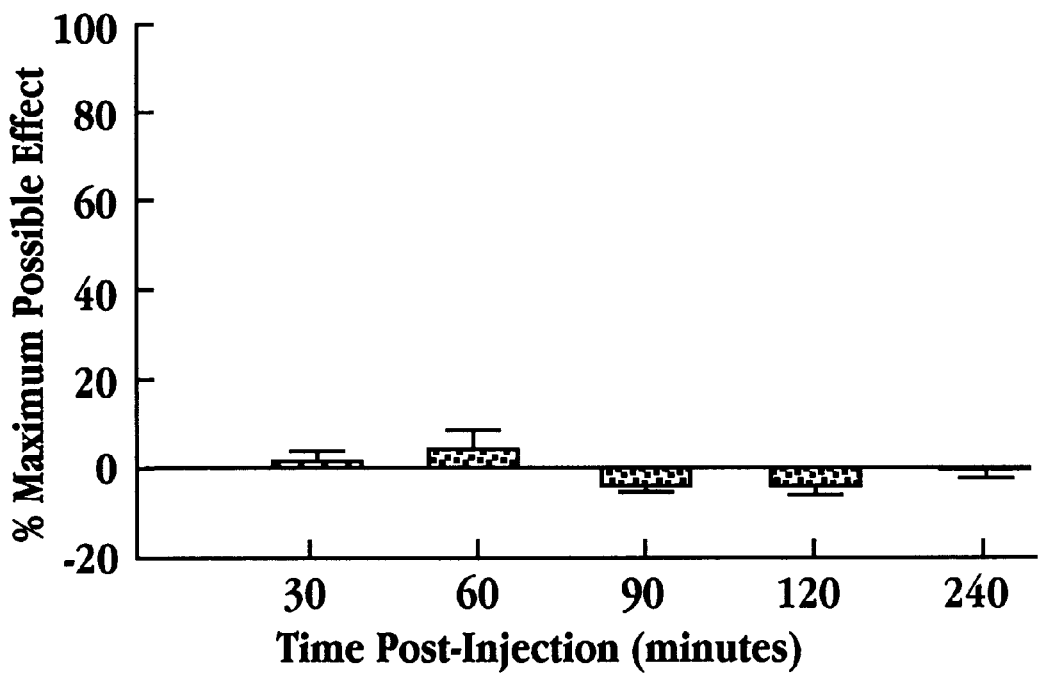
FIGS. 17A and 17B show histograms of thresholds of mechanical allodynia as % MPE at various times after epidural injection of saline (17A) or 30 µg SNX-111.
Figure 17B:
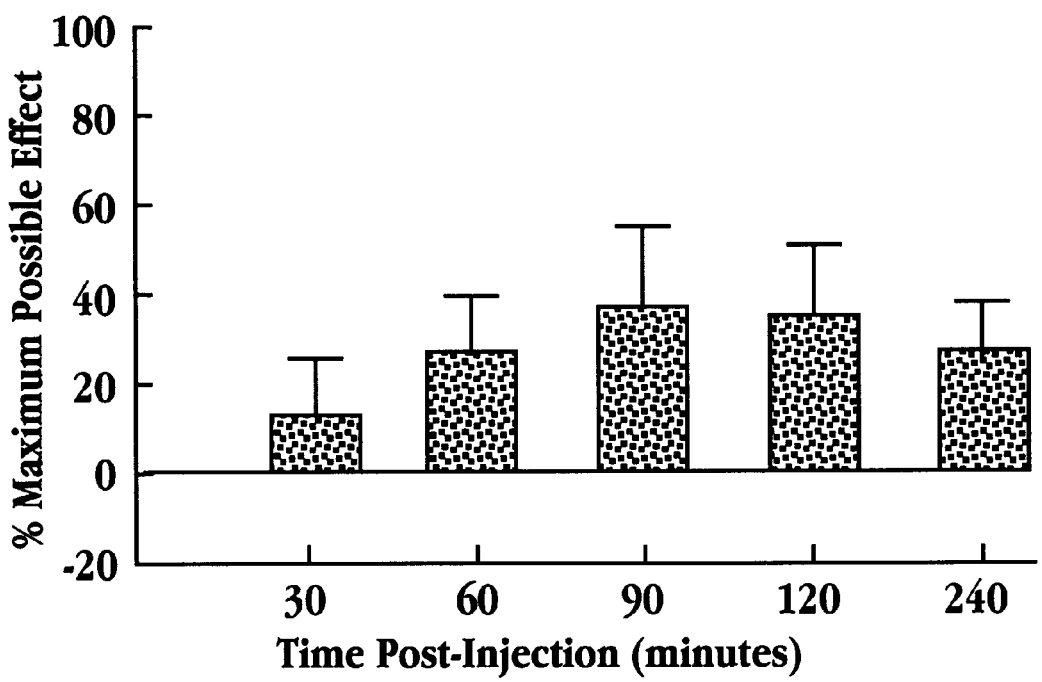

As discussed above in the preceding section, 0.1 µg SNX-111 blocks mechanical allodynia in nerve injured rats when it is administered spinally by intrathecal bolus injection. In the current study, epidural bolus injections of 30 µg SNX-111 produced modest elevations of mechanical allodynia thresholds (FIG. 17B). Maximum analgesia, as judged from the mean % MPE values, was achieved between 60 and 90 minutes after SNX-111 treatment. Animals given vehicle (saline) alone had consistently low allodynia thresholds at all measured time points. Individual threshold values were considerably more variable among animals of the SNX-111 treatment group than among those receiving vehicle only.

Figure 19:
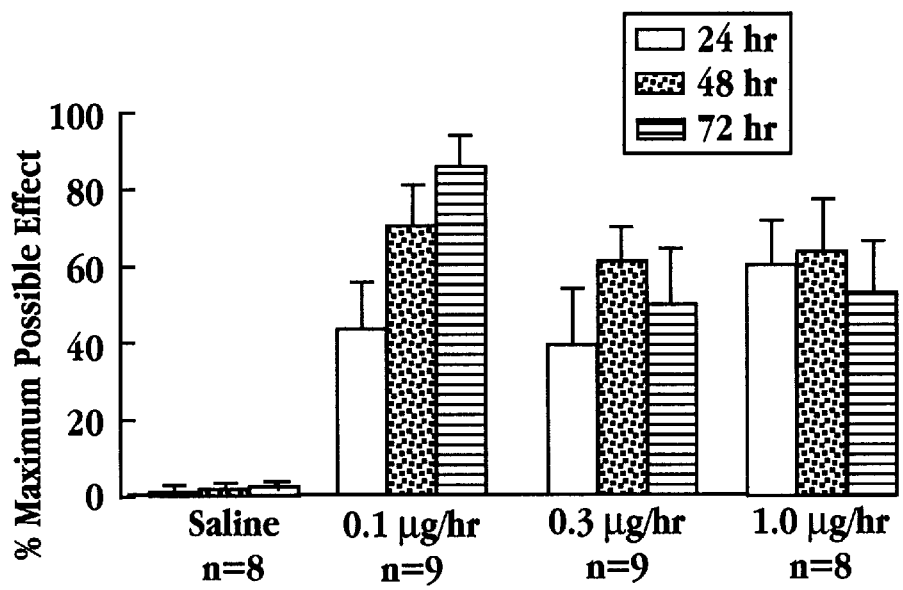
FIG. 19 shows histograms of thresholds of mechanical allodynia as % MPE after 24, 48 or 72 hours of constant infusion of saline or varying amounts of SNX-111 into the spinal lumbar epidural space of rats.
Figure 20:
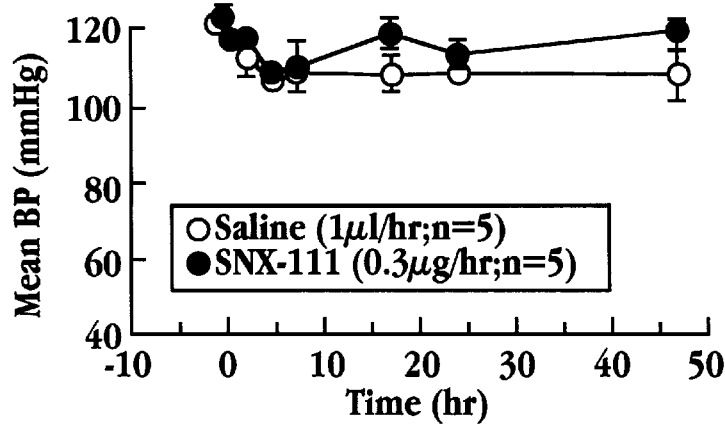
FIG. 20 shows the effects of continuous, constant rate (1 µl/hr) epidural infusion of 0.3 µg/hr SNX-111 or saline on mean systemic blood pressure in neuropathic rats.

In contrast to epidural bolus injections, continuous, constant-rate epidural infusions of 0.1 µg/hr, 0.3 µg/hr, or 1.0 µg/hr SNX-111 provided substantial elevations of mechanical allodynia thresholds 24 hr, 48 hr, and 72 hr after initiating treatment. Maximum analgesic effects were observed at a dose of 0.1 µg/hr; increasing the dose to 0.3 µg/hr or 1.0 µg/hr produced no further elevation of allodynia thresholds (FIG. 19). SNX-111 treatment (0.3 µg/hr) was not associated with changes in systemic blood pressure (FIG. 20). The analgesic effects of 0.1 µg/hr SNX-111 exceeded or were equivalent to those observed when the same dose was administered by continuous infusion intrathecally over equivalent time periods, as shown (FIG. 18).

E. Other Modes of Administration of Omega conopeptides

For treatment of pain generally, as exemplified herein, intrathecal as well as intravenous administration of the omega conopeptide is effective; in addition, other modes of administration may be appropriate, in accordance with the etiology of the particular painful stimulus. For example, as described in U.S. patent application U.S. Ser. No. 08/496,847, filed Jun. 27, 1996, perineural administration may be particularly desirable for use in treatment of neuropathic pain. Such perineural administration can be effected by topical means, either directly or with the use of a transdermal applicator. Alternatively, perineural administration may be effected by subdermal injection. The resulting blockade of calcium channels reduces the heightened sensation produced by transmission through the neurite proliferation. Perineural delivery may also be effected by forming a cuff around the damaged nerve, preferably of a biodegradable matrix which includes a therapeutic N-type calcium channel blocking compound, or by other means, known in the art for placing the therapeutic compound in close proximity to the damaged nerve, such as by transdermal delivery.

In addition, as further disclosed in U.S. patent application Ser. No. 08/496,847 progression or the underlying neuropathy may be treated by local administration of compound to those regions of the spinal cord, such as to dorsal horn regions at affected vertebral levels, where polysynaptic relay of pain sensation occurs. This type of local application can be effected by intrathecal administration, as described herein and in above-referenced co-pending application U.S. Ser. No. 08/049,794. Intrathecal administration delivers compound directly to the sub-arachnoid space containing cerebral spinal fluid (CSF). While effective, this method requires precise technical expertise to ensure delivery to the correct spot. According to the discovery of the present invention, epidural injection of omega conopeptides to a region of the spinal cord exterior to the arachnoid membrane, in the absence of a membrane permeabilizing agent may also be used to prevent progression of neuropathy.

In general, slow infusion, the prolonged administration methods described herein are particularly useful, when administration is via the intrathecal or epidural routes mentioned above; however, other areas, such are the bloodstream, may be targeted. Known in the art are a number of implantable or body-mountable pumps useful in delivering compound at a regulated rate. One such pump described in U.S. Pat. No. 4,619,652 is a body-mountable pump that can be used to deliver compound at a tonic flow rate or at periodic pulses. An injection site directly beneath the pump is provided to deliver compound to the area of need, for example, to the perineural region. Alternatively, prolonged administration may be effected by depot or sustained release formulations known in the art.

In other treatment methods, N-type calcium channel blocking compounds may be given orally or by nasal insufflation, according to methods known in the art. For administration of peptides, it may be desirable to incorporate such peptides into microcapsules suitable for oral or nasal delivery, according to methods known in the art.

Efficacy of the foregoing methods of treatment are conveniently measured in any of the standard experimental pain models described in Examples 7–9 herein. Efficacious dosages and formulations determined in the models are extrapolated to equivalent large animal and human dosages, according to methods known in the art.

F. Therapeutic Indications

Pain is a symptom of a wide variety of ailments. Chronic pain can be an unbearable consequence of injuries, trauma, certain cancers, and the like. Likewise, neuropathic pain may result from a number of separate etiologies. However, in many cases it will be preferable to treat the pain in a manner that addresses its specific source. For example, when the pain is traceable to injury of a particular nerve fiber, it may be appropriate to treat such pain either by perineural application of compound to the affected nerve or by dermal application of compound to the affected region. Neuropathic pain may occur as a consequence of ophthalmic surgery, dental repair (root canal), burn injury, reflex sympathetic dystrophy, post-herpetic neuralgia, diabetic neuropathy, arthritis and the like.

G. Dosages and Formulations

From the foregoing, it can be appreciated that treatment with N-channel blocking compounds and, more particularly, omega conopeptides having binding and inhibitory activities within the range of activities defined by omega conopeptides MVIIA (SNX-111) and TVIA (SNX-185) and more generally, SNX-199, SNX-236, and SNX-239, are useful in treating pain. Generally, dosages and routes of administration of the compounds will be determined according to the site of the pain and the size of the subject, according to standard pharmaceutical practices. Intrathecal administration, either as a bolus dosage and as a constant infusion, can be used for treatment and prevention of progression of neuropathic pain. In preferred embodiments, epidural dosages equivalent to at least 0.1–3 µg intrathecal (or about 2.4 µg continuous infusion over 24 hours) SNX-111 in rats are effective against peripheral neuropathy of the hindlimb. In accordance with the improved method described herein, dosages equivalent to 0.1 g/hr infused intrathecally over 24 hours are also effective epidurally, particularly when such doses are placed in sustained contact with the spinal meninges. Such sustained contact can be effected by continuous infusion, deposition of a sustained release formulation (such as a liposomal or depot formulation) or the like, according to methods well known in the art, as described in Section E, above.

It is also appreciated that compound can be administered perineurally, for example by topical or subdermal application to cutaneous regions having affected nerve endings, according to methods known in the art. In addition, administration may by epidural means, as discussed below.

Figure 16:
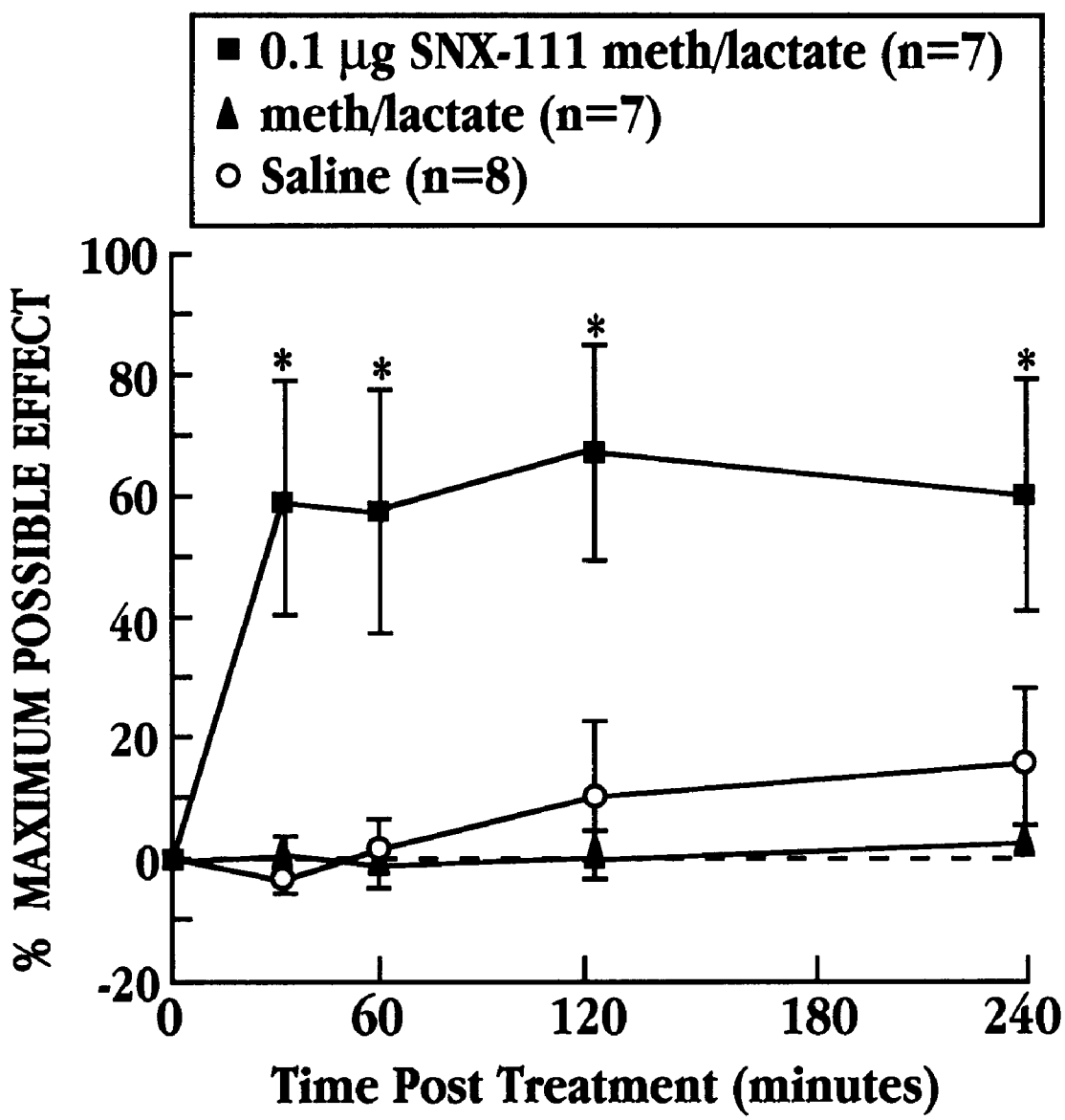
FIG. 16 shows analgesic efficacy of an SNX-111 formulation combining methionine in lactate buffer.

Stabilized formulations, as described in Section I.C above, are useful in storing and administering therapeutic omega conopeptides according to the methods described herein. While it may be desirable to neutralize the solutions prior to administration, formulations utilizing lactate or acidified saline as excipient may also be administered directly via acute epidural or intrathecal bolus injection or by other routes for which acidified excipients are appropriately used. Neutralization, if required, can be accomplished by dilution into a pharmaceutically acceptable neutralizing excipient buffer, just prior to injection into the subject. FIG. 16 shows the results of experiments demonstrating that SNX-111 administered as a methionine-lactate formulation was as effective as SNX-111 alone in reducing neuropathic pain.

For some applications, it may be desirable to include in the omega conopeptide composition or treatment regimen means for enhancing permeation of the conopeptide through meningeal tissues which may surround the damaged or target nerve. Means for enhancing transport of compound are known in the art and may include encapsulating the conopeptide in liposomal membranes, addition of a surfactant to the composition, addition of an ion-pairing agent, and the like. Alternatively, or in addition, transmeningeal transport may be facilitated by administering to the subject a hypertonic dosing solution effective to disrupt meningeal barriers, according to methods well known in the art. Alternatively, trans meningeal or transcutaneous transport may be further facilitated by modifying the primary sequence of omega-conopeptide, for example by substituting neutral amino acid sidechains or hydrophobic moieties for cationic residues.

The following examples are intended to illustrate various characteristics of the method of the invention, but are in no way intended to limit the scope of the invention.

EXAMPLE 1

Preparation of OCT Peptides

Abbreviations used in this example are BOC, tertiary butoxycarbonyl; DCM, dichloromethane; TFA, trifluoroacetic acid; IPM, N-isopropylmorpholine; BOC-AA-OH, BOC amino acid; DIEA, diisopropylethylamine; 2-ClZ, chlorobenzyloxycarbonyl; tosyl, p-toluene-sulfonyl; DMF, N,N-dimethylformamide; TFE, trifluoro-ethanol; SA, symmetrical anhydride of BOC-AA-OH; DCCI, N,N-dicyclohexylcarbodiimide; E, ethyl ether; P, petroleum ether.

Commercially available benzhydrylamine-resin hydrochloride, Lot No. B30101, was obtained from commercial sources (Beckman Instruments Inc., Palo Alto, Calif.; Advanced ChemTech). With this resin, cleavage of a peptide formed on the resin, under the conditions described below, produces a peptide which is amidated at its carboxy end.

A. Preparing Protected Amino Acid Anhydrides

Each BOC-AA-OH (2.4 mmol) was dissolved in 5 ml $CH_2Cl_2$ and cooled to 0° C. The volume of DCM used for BOC-Leu-OH (dried in vacuo) was 12 ml, and the BOC-Leu-OH solution was not cooled. 2 ml 0.6 M DCCI in DCM was added and the mixture stirred at 0° C. for 15 min. For BOC-Leu-OH, the mixture was also cooled after this addition. Precipitation of N,N-dicyclohexylurea was completed by storage at −20° C. for 1.5 hour, after which the precipitate was filtered and washed with ethyl ether (5 ml). The filtrate was evaporated to remove solvents and the product was crystallized in the solvent system given in the Table below. Residual amounts of DCM can affect the exact conditions for crystallization. Recrystallization was performed by dissolving in DCM, evaporating most of the solvent, and recrystallizing from the appropriate solvent.

| TABLE OF AMINO ACID SOLVENTS | |
|---|---|
| Amino Acid | Solvent |
| Ala | DCM:E:P |
| Asp (Benzyl) | E:P |
| Gly | E:P |
| Leu | P |
| Lys (2-ClZ) | E:P |
| Met | E:P |
| Ser (Benzyl) | E:P |
| Thr (Benzyl) | E:P |
| Tyr (2-BrZ) | DCM:P |

B. Preparation of MVIIA

Synthesis of MVIIA peptide was performed on 0.58 g benzhydrilamine resin (0.40 mmol) in a Beckman Model 990 Peptide Synthesizer by a solid-phase method based on the primary structure shown in FIG. 1A.

A double coupling protocol was used for the incorporation of residues Cys-25 through Tyr-13, and a triple coupling protocol, for amino acids Met-12 through Cys-1. Symmetrical anhydrides were used in crystalline form as described in Yamashiro (1987). Crystalline symmetrical anhydrides (1.0 mmole) were each dissolved in 6 ml DCM and stored in the amino acid reservoirs at 4° C. Sidechain protecting groups used were: Cys, 4-MeBenzyl; Lys, 2-ClZ; Ser, Benzyl; Arg, Tosyl; Thr, Benzyl; Asp, Benzyl; Tyr, 2-Br-Benzyl.

Unless specified, volumes were 8 ml, except for step 2 below, which was 10 ml, and all reactions were carried out at room temperature. After incorporation of the Asp-14 residue, the volume of step 2 was increased to 15 ml while all other volumes were raised to 10 ml after incorporation of the Arg-10 residue. The double coupling protocol consisted of steps 1–16 listed in the Table below.

Amino acids Met-12 through Cys-1 were added by a triple coupling protocol which included, in addition to steps 1–16, steps 17–20 in the MVIIA protocol Table.

MVIIA PROTOCOL TABLE

| Step | Reagent |
| --- | --- |
| 1 | DCM wash (3 times) |
| 2 | 67% TFA/M (20 min.) |
| 3 | DCM wash (2 times) |
| 4 | 25% dioxane/DCM wash (2 times) |
| 5 | 5% DIEA/DCM wash |
| 6 | DCM wash |
| 7 | 5% DIEA/DCM wash |
| 8 | DCM wash (5 times) |
| 9 | 1.0 mmol SA in DCM (5 min) |
| 10 | 0.5 mmol IPM in 3 ml TFE plus 1 ml DCM |
| 11 | (5 min) |
| 12 | 0.5 mmol IPM in 5 ml DCM (5 min) |
| 13 | DMF wash (3 times) |
| 14 | 1.0 mmol SA in DMF (5 min) |
| 15 | 0.5 mmol IPM in 5 ml DCM (5 min) |
| 16 | 0.5 mmol IPM in 4 ml DMF (5 min) |
| 17 | DCM wash |
| 18 | DCM wash (2 times) |
| 19 | 1.0 mmol SA in DCM (5 min) |
|  | 0.5 mmol IPM in 4 ml DMF (5 min) |
| 20 | DCM Wash |

Crystalline symmetrical anhydrides (1 mmole) were each dissolved in 6 ml DCM or DMF and stored in the amino acid reservoirs at 4° C. Side-chain protecting groups used were: Cys, 4-MeBzl; Lys; ClZ; Ser, Bzl; Arg, tosyl; Thr, Bzl; Asp, Bzl; Tyr, BrZ.

For BOC-Arg(tosyl)-OH, the following mixture was prepared: 1.87 BOC-Arg(tosyl)-OH, 0.57 g 1-hydroxybenzotriazole, 15 ml DMF, stirred to dissolve, cooled to 4° C., added 0.52 ml diisopropylcarbodiimide, and split in half for steps 9 and 13. For this coupling, the protocol was modified as follows: step 8 was 3 times DCM wash and 2 times DMF wash; step 9 was for 10 min; step 11 was for 10 min; step 13 was for 10 min; step 14 was 0.4 mmol IPM in 4 ml DMF for 10 min; step 15 was for 10 min; step 16 was 1 times DMF wash and 1 time DCM wash. Reaction mixtures in steps 9, 10, 13, 14 and 18 were not drained.

The mixture for a third coupling for incorporating the Arg-10 residue consisted of 1.00 g BOC-Arg(tosyl)-OH, 1 ml DMF, 5 ml DCM, stirred to dissolve, and cooled to 4° C. to which is then added 1.67 ml 0.6 M DCCI in DCM.

After the last amino acid had been incorporated, the protected peptide resin was subjected to steps 1–4 to remove the N-terminal BOC group, collected on a filter with use of ethanol, and dried in vacuum to yield 2.61 g.

MVIIA has also been successfully synthesized on an ABI 430A synthesizer using slight modifications of the above protocol.

C. Deblocking and Cleavage in Liquid HF

A mixture of protected peptide resin (1.32 g), 2-mercaptopyridine (0.50 g), p-cresol (2.6 g), and liquid hydrogen fluoride (HF) (25 ml) was stirred at 0° C. for 80 min. The liquid HF was evaporated with a rapid stream of nitrogen gas, first below 0° C., then at 24° C. The mixture was stirred in ethyl acetate (25 ml) until a finely divided solid was obtained. The solid was filtered, washed with ethyl acetate, and air dried to yield 1.09 g. This solid was stirred in 50% aqueous acetic acid (10 ml) to dissolve the peptide material, filtered, and washed with 20 ml water. The filtrate was freeze-dried to yield 450 mg of fluffy powder.

D. Formation of Disulfide Bridges

A sample (300 mg) of the fluffy powder was dissolved in 30 ml of 0.05 M ammonium bicarbonate, 10 mM dithiothreitol (DTT), and 2 M guanidine hydrochloride. The solution, which had a pH of 6.7, was allowed to stand at 24° C. for 2 hr, then diluted with 120 ml of water and stirred for 20 hr at 24° C. DTT (25 mg) was added and the solution allowed to stand at 24° C. for 80 min. The mixture was then stirred at 4° C. for 3 days.

E. Isolation of MVIIA OCT

The solution from Part D was acidified with glacial acetic acid (2 ml), evaporated in vacuo to a low volume, and fractionated by gel filtration on Sephadex G-25 in a 2.5×48 cm column, using 1 N acetic acid, to remove peptide polymeric species (exclusion volume), and salts (slowest moving peak). Fractions (5 ml) were collected, with peptide absorbance monitored at 280 nm. Fractions corresponding to the monomer peptide were pooled and freeze-dried to give 127 mg of fluffy powder. A sample of the monomeric material (34 mg) was purified by preparative HPLC on a Vydac 218TP1022 column with a gradient of 10–20% acetonitrile in 0.1% trifluoroacetic acid over 50 min at 8 ml/min, with detection at 226 nm and collection of 4 ml fractions. Fractions corresponding to the major peak were pooled, evaporated in vacuo to remove acetonitrile, and freeze-dried to yield 7.7 mg. Analytical HPLC on a Vydac 218TP104 column with the same solvent and gradient over 10 min followed by 10 min of isocratic elution at the 20% composition (1.5 ml/min) gave a single peak identical in behavior to an authentic sample of OCT MVIIA. Amino acid analysis of a 24-hr HCl-hydrolysate gave: Asp, 0.93; Thr, 1.05; Ser, 2.85; half-cystine, 5.2; Gly, 4.08; Ala, 1.07; Met 0.94; Leu, 1.02; Tyr,0.85; Lys, 3.98; Arg, 2.09.

F. Radio-Iodination of MVIIA

MVIIA peptide was iodinated by reaction with Iodogen™ in the presence of NaI according to Cruz et al., with minor modification. 2 m Ci of carrier-free $Na^{125}I$, 75 ul 0.5M phosphate buffer pH 7.4 and 20 ul of 1 ug/ul peptide were added to a polypropylene test tube coated with 10 ug Iodogen™. The tube was agitated for 8 minutes, and the solution was chromatographed by HPLC through a 10×0.46 cm C-8 reverse phase column with a pore size of 300 Å (Brownlee Labs, Santa Clara, Calif.). The sample material was eluted with a gradient from 0.1% trifluoroacetic acid to 60% acetonitrile in 0.1% trifluoroacetic acid. The major peak of active radio-iodinated peptide was resolved at about 2 minutes greater retention time than the underivatized peptide.

The fractions containing this peak were collected and later diluted for use in binding experiments. MVIIA, iodinated under the conditions as above except with non-radioactive NaI, was tested for the ability to inhibit depolarization-dependent ATP release from synaptosomes as described in Ahmad and Miljanich (1988) and found to be as potent in this regard as the underivatized peptide.

G. Synthesis of Other OCT Peptides

Synthesis of other OCT peptides was according to the solid-phase method described above, except that a single coupling protocol involving steps 1–12 in Part C was used for coupling the first 10 C-terminal amino acids residues, and a double coupling method involving steps 1–16, Part C was used for coupling the final n⁻10 N-terminal residues, where n is 24–29. Releasing the peptide from the solid support, removing the blocking groups, and joining the disulfide bridges were carried out substantially as above, or as described in Part H, below. The peptide was separated from salts and polymeric peptide species by gel filtration on Sephadex G-25, and purified on preparative HPLC. For binding studies, each peptide can be radioiodinated essentially as above.

H. Alternate Oxidation Methods

Two alternative oxidation methods were used in the preparation of MVIIA/SNX-111.

1. The lyophilized crude linear peptide was dissolved in 3 M guanidine hydrochloride and 1.2M ammonium acetate solution to yield a concentration of approximately 12 mg peptide/ml. DTT was added to a ratio of 15 mg DTT per 100 mg peptide, and the mixture was stirred at room temperature for 1 hour. The solution was diluted 6-fold with distilled water, and stirred at 4° C. for 3-5 days. The progress of peptide oxidation was monitored by HPLC. The endpoint of the oxidation process was the complete disappearance of free thiols, determined by Ellman reaction.

2. The lyophilized crude linear peptide was dissolved in 3 M guanidine hydrochloride and 0.3 M potassium phosphate solution to yield a concentration of approximately 12 mg peptide/ml. After addition of 40 mg cysteine and 15 mg DTT per 100 mg peptide, the pH of the solution was adjusted to 8.0–8.1 with potassium hydroxide solution. The mixture was stirred at room temperature for 1 hour. The peptide solution was diluted 6-fold with water, and stirred at 4° C. for 3–5 days. The progress of peptide oxidation was monitored by HPLC. The endpoint of the oxidation process was the complete disappearance of free thiols, determined by Ellman reaction. (Method 2 was used in the preparation of SNX-236 and SNX-239).

Following oxidation by either of the above methods, the solution was acidified with acetic acid to pH 3, and lyophilized.

EXAMPLE 2

Calcium-Channel Antagonist Activity: Inhibition of Ionic Currents

Ionic currents through calcium channels were examined in cells that were voltage-clamped by a single patch-clamp electrode. These whole-cell patch-clamp studies were performed mainly on N1E115 mouse neuroblastoma cells, although a variety of cell types, including human neuroblastoma cell line IMR-32, have been examined.

A. Current Measurement Methods

Most measurements were obtained using a bath saline that allowed examination of the calcium currents in the absence of other ionic currents. These solutions contained 80 mM NMDG (as a sodium replacement), 30 mM TEACl (to block potassium currents), 10 mM $BaCl_2$ (as a charge-carrier through the calcium channels), and 10 mM HEPES at pH 7.3. Some solutions also contained 2 mM quinidine (to block potassium currents) and 3 $\mu$M tetrodotoxin (to block sodium currents). Normal bath saline was (mM): 140 NaCl, 10 glucose, 3 KCl, 2 $CaCl_2$, 1 $MgCl_2$, 10 mM HEPES pH 7.3. Intracellular solutions contained 150 mM CsCl, 0.5 mM $CaCl_2$, 5 mM EGTA, 5 mM $MgCl_2$, 2 mM $K_2ATP$ at pH 7.3–7.4. Bath saline and all internal solutions were filtered before use.

Pipets were made from Corning 7052 glass (Garner Glass Company, Claremont, Calif. 91711), coated with Sylgard (Dow Corning, Midland, Mich. 48640) and fire-polished before use. Bubble numbers were typically 5 to 6, with pipet resistances typically 2–5 MOhms. Corning 8161, Kimble, and other glasses were also used without noticeable effect on the calcium currents observed.

Recordings were carried out at room temperature with an Axopatch 1-C amplifier (Axon Instruments, Foster City, Calif. 94404) and analyzed with pCLAMP software (Axon Instruments). Data were filtered at 1000 Hz for a typical sampling rate of 0.1 kHz; in all cases data were filtered at a frequency at most ⅕ of the sampling rate to avoid biasing. Data were collected on-line by the software. Analysis was performed on-screen with print-out via a Hewlett-Packard LaserJet Printer (Hewlett-Packard, Palo Alto, Calif. 94306).

The typical experiment was conducted as follows: after seal formation followed by series resistance compensation and capacitative transient cancellation, a voltage clamp protocol was performed wherein the cell potential was stepped from the holding potential (typically –100 mV) to test potentials that ranged from –60 mV to +20 mV in 10 mV increments. The cell was held at the holding potential for 5 seconds between pulses. Protocols starting from other holding potentials usually covered the same range of test potentials.

B. Current Inhibition Measurement

FIG. 3 shows calcium current traces from an N1E115 mouse neuroblastoma cell. The figure is read from left to right in time, with downward deflections of the trace indicating positive current flowing into the cell. Currents were elicited by a voltage step from 100 mv to –10 mV. The cell was bathed in saline with sodium replaced by NMDG and 10 mM $Ba^{++}$ instead of 2 mM $Ca^{++}$. Potassium currents were blocked by TEA in the bath and $Cs^+$ in the pipet solution.

The three traces in FIG. 3, labeled B–D, show decreasing calcium currents, with increasing MVIIA omega-conopeptide concentrations of 10 nM (3B), 50 nM (3C), and 200 nM (3D).

The response of voltage-gated calcium current to increasing dosages of OCTs MVIIA and GVIA are shown in FIG. 4. The calculated $IC_{50}$ is approximately 10 nM for GVIA and 100 nM for MVIIA. These values indicate extremely high specificity of the peptides for their site of action.

$IC_{50}$ values for GVIA, MVIIA, SVIB and SVIA OCTs were determined from these measurement. Whereas OCT GVIA and OCT MVIIA showed 50% inhibition of the measured calcium current at nanomolar concentration range, $IC_{50}$ values for OCT SVIB and OCT SVIA were not measurable within the range of concentrations tested, and are therefore listed as having $IC_{50}$ values above the micromolar concentrations indicated.

EXAMPLE 3

Omega-conopeptide Binding to Omega-conopeptide Binding Sites in Synaptosomal Membranes A. Preparation of Mammalian-Brain Synaptosomes and Synaptosomal Membranes Synaptosomes were prepared from rat whole brain or hippocampal region of brain. Rats were sacrificed, and forebrains were removed and transferred to 10 ml ice-cold 0.32 M sucrose containing the following protease inhibitors (PI): 1 mM EGTA; 1 mM EDTA; 1 uM pepstatin; 2 uM leupeptin. Brains were homogenized using a motor-driven Teflon-glass homogenizer (approx. 8 passes at 400 rpm). Homogenates from 4 brains were pooled and centrifuged at 900×g for 10 minutes at 4° C. Supernatants were then centrifuged at 8,500×g for 15 minutes. Resulting pellets were resuspended in 10 ml each ice-cold 0.32 M sucrose plus PI with vortex mixing. The suspension was then centrifuged at 8,500×g for 15 minutes. Pellets were resuspended in 20 ml ice-cold 0.32 M sucrose plus PI. The suspension (5 ml/tube) was layered over a 4-step sucrose density gradient (7ml each: 1.2 M sucrose, 1.0 M sucrose, 0.8 M sucrose, 0.6 M sucrose; all sucrose solutions containing PI). Gradient tubes were centrifuged in a swinging bucket rotor at 160,000×g for 60 minutes at 4° C. The 1.0 M sucrose layer plus the interface between the 1.0 and 1.2 M sucrose layers were collected and diluted with ice cold deionized water plus PI to yield a final sucrose concentration of 0.32 M. The resulting suspension was centrifuged at 20,000×g for 15 minutes. Pellets were then resuspended in 5 ml ice-cold phosphate buffered saline plus PI. The resulting rat brain synaptosomes were then aliquoted and stored in a liquid nitrogen containment system.

Prior to use in binding assays, synaptosomes were thawed and diluted with 3 volumes of ice cold deionized water plus PI. This suspension was homogenized using a PT 10–35 Polytron (setting 6) for two 10-second bursts. The homogenate was centrifuged at 40,000×g for 20 minutes at 4° C. The resulting pellets were resuspended in about 5 ml of ice cold phosphate buffered saline plus PI. The resulting brain synaptosomal membrane preparation was aliquoted and stored at −80° C. until use. Protein concentration of the membrane preparation was determined using Bradford reagent (BioRad), with bovine serum albumin as standard.

B. Saturation Binding Assay

MVIIA OCT was radiolabeled with $^{125}$I-iodine by reaction with Iodogen™, essentially according to the method of Ahmad and Miljanich (1988). Following the Iodogen reaction, the peptide solution was chromatographed by HPLC through a C-8 reversed phase column and eluted with a gradient from 0.1% trifluoroacetic acid in water to 0.1% trifluoroacetic acid in water/acetonitrile (40:60 vol/vol). The major peak of radioactivity following the underivatized MVIIA OCT was collected.

The binding constant ($K_d$) for [$^{125}$I]-MVIIA OCT to rat brain synaptosomal membranes was determined by a saturation binding method in which increasing quantities of [$^{125}$I] MVIIA OCT were added to aliquots of a synaptosomal membrane preparation (10 ug membrane protein, suspended in binding buffer consisting of 20 mM HEPES, pH 7.0, 75 mM NaCl, 0.1 mM EGTA, 0.1 mM EDTA, 2 $\mu$M leupeptin, 0.035 $\mu$g/ml aprotinin, and 0.1% bovine serum albumin (BSA), in a total volume of 0.5 ml). Binding at each concentration of labeled compound was determined in the absence and presence of 1 nM unlabeled MVIIA OCT to determine specific binding (as described in part B, below). The amount of labeled peptide specifically bound at each concentration was used to determine $B_{max}$, the concentration of specific binding sites on the synaptosomes, and $K_d$, following standard binding analysis methods (Bennett, et al., 1983). Scatchard analysis of saturation binding curve of [$^{125}$I]MVIIA revealed a $K_d$ of about 10 pM for the compound.

B. Competitive Displacement Binding Assay

1. Competitive Displacement of OCT MVIIA. Rat brain synaptosomal membranes prepared as described in Part A were suspended in a binding buffer consisting of 20 mM HEPES, pH 7.0, 75 mM NaCl, 0.1 mM EGTA, 0.1 mM EDTA, 2 $\mu$M leupeptin, 0.035 $\mu$g/ml aprotinin, and 0.1% bovine serum albumin (BSA). [$^{125}$I]-MVIIA (SNX-111) OCT (25–30,000 cpm, approximately 1500–2000 Ci/mmol) and test compound were aliquoted into polypropylene tubes, in the absence or presence of 1 nM MVIIA (SNX-111) OCT to determine non-specific binding. The membrane suspension was diluted and aliquoted last into the test tubes, such that each assay tube contained 10 $\mu$g membrane protein and the total volume was 0.5 ml. After incubation for 1 hour at room temperature, tubes were placed in an ice bath, then filtered through GF/C filters (Whatman), which were presoaked in 0.6% polyethyleneimine and prewashed with wash buffer (20 mM HEPES, pH 7.0, 125 mM NaCl, 0.1% BSA) using a Millipore filtration system. Just prior to filtration, each assay tube received 3 ml ice-cold wash buffer. The filtered membranes were washed with two 3 ml volumes of ice-cold wash buffer, dried, and filter-bound radioactivity was measured in a Beckman gamma counter (75% counting efficiency).

Representative displacement binding curves for rat brain synaptosomal membranes are illustrated in FIG. 3. IC$_{50}$ values were computed from line fit curves generated by a 4-parameter logistic function. These values represent the concentration of test compound required to inhibit by 50% the total specific binding of [$^{125}$I]-MVIIA (SNX-111) OCT to rat brain synaptosomal membranes, where specific binding is defined as the difference between binding of [$^{125}$I]-MVIIA (SNX-111) OCT in the absence and presence of excess (1 nM) unlabelled MVIIA OCT. Non-specific binding is that binding of radiolabeled compound which is measured in the presence of excess unlabeled MVIIA OCT. Such values serve as approximations of the relative affinities of a series of compounds for a specific binding site.

2. Competitive Displacement of OCT SVIB. Rat brain synaptosomal membranes were prepared as described above. OCT SVIB was radiolabeled by iodination with $^{125}$I-iodine by the Iodogen reaction. Displacement binding of radiolabeled SVIB on rat brain synaptosomal membranes was carried out as in Example 4B. SVIB displacement curves for several of the omega-conopeptides assayed is shown in FIG. 4. IC$_{50}$ values and relative potency values were calculated as described below. Tables 2 and 3 show the relative potency values for omega-conopeptides examined, and the ratio of relative potencies of the compounds for the OCT MVIIA site and to the SVIB binding site.

The binding constant ($K_i$) for each test substance was calculated using non-linear, least-squares regression analysis (Bennett and Xie, 1988) of competitive binding data from 2 assays performed in duplicate on separate occasions. The relationship between $K_i$ and IC$_{50}$ (concentration at which 50% of labeled compound is displaced by test compound is expressed by the Cheng-Prusoff equation:

$$K_i = IC_{50}/(1+[L]/K_d)$$

where IC$_{50}$ is the concentration of test substance required to reduce specific binding of labeled ligand by 50%; [L] is the concentration of [$^{125}$I]-MVIIA (SNX-111) OCT used in the experiment; and $K_d$ is the binding constant determined for binding of [$^{125}$I]-MVIIA (SNX-111) OCT to rat brain synaptosomal membranes in saturation binding experiments. Table 3 summarizes computed IC$_{50}$ for various omega-conopeptides for the MVIIA binding site of rat brain synaptosomal membranes.

Relative potency for displacement of binding is calculated as a ratio of the IC$_{50}$ of the test compound and the IC$_{50}$ of the reference compound. The reference compound is generally the unlabeled equivalent of the labeled ligand. Calculation of relative potency is as follows:

[log (relative potency)]=log ($IC_{50(ref)}$)−log($IC_{50}$(test))

EXAMPLE 4

Binding to Meningeal Membranes

Meningeal membranes were obtained from the spinal cords (T3 to L5) of *Macaque nemestrina* monkeys. The spinal cords were removed and incisions were made simultaneously through all three meningeal layers along the ventral surfaces. Together, the dura, arachnoid, and pia mater were carefully collected from each spinal cord, preserving their normal anatomic relationships.

Frozen spinal pia-arachnoid membranes were minced, suspended in 5 ml of deionized water containing protease inhibitors (1 mM EDTA, 1 EGTA, 1 $\mu$M pepstatin, 2 $\mu$M leupeptin), homogenized with a Polytron (PT-10–35, speed 6) for 10 seconds, and centrifuged at 40,000 g for 20 min. The membrane pellet was resuspended in 5 ml of 0.05 M phosphate buffer, pH 7.4, containing protease inhibitors and stored in liquid nitrogen until used. The protein concentration in the membrane preparation was determined using the Bradford Reagent (Bio-Rad) with bovine serum albumin (BSA) as a standard. Binding assays were carried out at room temperature in 12×75-mm polypropylene tubes. The binding buffer contained 20 mM Hepes, pH 7.2, 75 mM NaCl, 0.1 mM EDTA, 0.1 mM EGTA, 2.0 $\mu$M leupeptin, 0.5 U aprotonin, and 0.1% BSA. The binding mixture contained 5 $\mu$g of meningeal membranes in 0.2 ml, $^{125}$I-SNX-111 in 0.1 ml, and 0.2 ml binding buffer to give a final volume of 0.5 ml per tube. $^{125}$I-SNX-111 competition binding curves were generated by adding various concentrations of SNX-194 ([N1e$^{12}$] SNX-111) to the assay tubes. Non-specific binding was determined in the presence of 500 $\mu$M of SNX-194. The reaction was terminated by transferring the assay tubes to an ice-cold water bath and diluting each sample with 3 ml of chilled washing buffer (20 mM Hepes, pH 7.2, 125 mM NaCl, 0.1% BSA). Membrane-bound radioactivity was separated on a Millipore manifold filtration system using glass fiber filters which were presoaked in 0.6% polyethyleneimine. Filters were washed twice (3 ml) with ice-cold washing buffer and counted in a Beckman gamma counter (Model G-500) at 75% counting efficiency. Data were fitted to a four-parameter logistic function:

$$\text{Effect} = E_o + (E_i - E_o) * 1/1 + (K/L)^h$$

where $E_o$=effect at 0 dose, $E_i$=effect at infinite dose, $K=IC_{50}$, L=concentration of competing ligand, and h=slope. Parameter values were calculated by computer (Hewlett-Packard 9000) using a nonlinear, least-squares curve-fitting algorithm.

EXAMPLE 5

Inhibition of Neurotransmitter Release

A. Inhibition of Norepinephrine Release

Inhibitory constants (IC50's) reflecting the potency of SNX-111 and SNX-183, for blocking the K$^+$-evoked release of exogenous, loaded [$^3$H]-norepinephrine from rat hippocampal slices were determined. Freshly dissected hippocampal slices in oxygenated buffered saline were loaded with [3H]-norepinephrine and washed three times. Slices were then exposed to buffered saline (containing 3.3 mM K$^+$) for 1.5 minutes and the supernatants containing released basal norepinephrine were collected for scintillation counting. The slices were then depolarized by exposure to buffered saline containing 30 mM K$^+$ for 1.5 minutes and the supernatants, containing evoked norepinephrine, were also collected for scintillation counting. Slices were exposed to the desired concentration of peptide in all solutions from the time of loading with norepinephrine to the end of the experiment (about 2 hours). The data points are the differences of the means of 7 basal determinations and 7 evoked determinations at each drug concentration. Release in the absence of drug is taken as 100 per cent and the remaining points are scaled accordingly. The error bars are the standard errors of the means of the differences. Curves of best fit and the corresponding IC50's were derived. The single IC$_{50}$ for SNX-111 is correlated with binding to site 1 calcium channels; the two IC$_{50}$s for SNX-230 are for inhibition associated with binding to site 1 calcium channels (65nM) and to site 2 calcium channels (0.02 nM); the apparent single IC50 for SNX-183 is presumed to reflect binding to both site 1 and site 2 calcium channels with about equal affinity (see text). Evoked release in the absence of Ca$^{++}$ in the buffer was equal to basal release (data not shown); thus all release shown is calcium-dependent release.

B. Inhibition of Dopamine Release from Rat Striatal Slices

Slices (0.3×0.3×1.5 mm) were prepared from rat striatum, and were pre-loaded with radiolabeled (tritiated) dopamine. Slices were perfused for 45 minutes in Krebs Ringer Bicarbonate buffer (oxygenated) as bathing medium. Release of neurotransmitter was stimulated by adding to the perfusion medium KCl at a concentration ranging between 4.8 and 15 mM, for a period of one minute. The first such exposure was termed S1. Perfusion with bathing medium was continued. Test compound(s) were introduced into the perfusion medium 20 minutes before the second stimulation (S2), which was done identically to S1. The ratio of S2/S1 was calculated to determine drug effects. A drug was considered to block release if S2/S1 was significantly less than unity.

C. Inhibition of Acetylcholine Release from Striatal Slices

Release of acetylcholine was measured as described above in part B for dopamine release, except that slices were pre-loaded with radiolabelled choline instead of dopamine.

EXAMPLE 6

Inhibition of Electrically Stimulated Contractions of Guinea Pig Ileum

Guinea pigs (300–400 gms) were decapitated and the ileum removed. A section of ileum about 6 cm from the caecum was placed immediately into Krebb's modified buffer maintained at 37° C. in a water bath, and aerated with a mixture of 95% $O_2$ and 5% $CO_2$. The buffer contains: KCl, 4.6 mM; $KH_2PO_4$, 1.2 mM; $MgSO_4$, 1.2 mM; Glucose, 10.0 mM; NaCl 118.2 mM; $NaHCO_3$, 24.8 mM; $CaCl_2$, 2.5 mM.

Small pieces of ileum were cut and pulled over a glass pipette, scored and the longitudinal muscle removed. Each piece was attached to an electrode at one end and to a force transducer at the other end. The preparation was lowered into an organ bath maintained at 37° C. and aerated with $O_2$:$CO_2$. The resting tension was set at 1 gm, and the tissue was stimulated at 30–50V with a duration of 4.5 msec per stimulation.

Baseline responses (contractions) were recorded for 10–15 min. and aliquots (100 ml) of drug were added to the bath until inhibition occurred. Following testing, tissues were washed until original response magnitude was achieved.

EXAMPLE 7

Rat Tail-Flick Assay for Analgesia

Male Sprague-Dawley rats (250–300g; Simonsen) were implanted with intrathecal (i.t.) catheters, which were inserted through the atlanto-occipital membrane and threaded subdurally about 8 cm therefrom. Animals were not used in experiments until at least 2 days following implantation.

To perform the Tail-Flick test, a rat was restrained in a plastic cone having openings at each end, and was placed on a platform, positioned such that its tail hung down from the platform in close proximity to a heating bulb. Latency to flick the tail away from the bulb was recorded. A trial consisted of four such flicks at 1–2 min. intervals, where the first latency time was generally not used, and the three subsequent tests were averaged. Latencies measured in the absence of analgesic agent(s) were recorded for each rat as "Baseline latency."

Rats were then removed from the restraining cones, and injected (i.t.) with test compound in a volume of 5 $\mu$l, followed by 10 $\mu$l saline. Animals were subjected to post-drug trials at one or more time intervals thereafter (usually 25 min and 45 min.), as described above. In the cases where drug enhancement was tested, test compound was first injected, followed by tail-flick trials, to assess the potency of the drug alone. Approximately 1 hour later, a known analgesic, such as morphine, was injected, and trials repeated.

Drug effects were calculated as follows:

$$\% \text{ Effect} = 100 \times \frac{\text{(post-drug latency)} - \text{(baseline latency)}}{\text{(maximum latency)} - \text{(baseline latency)}}$$

where maximum latency was measured as experimental cut-off time, the time beyond which the tail was not allowed by the experimenter to be exposed to heat, due to risk of burn to the animal.

EXAMPLE 8

Rat Formalin Test for Analgesia

Rats (male Sprague-Dawley, 275–300 g, Harlan Industries, Indianapolis, Ind.) were implanted with lumbar intrathecal catheters under halothane anesthesia (Yaksch and Rudy). Catheters (Polyethylene PE-10) extended from the cisterna to the rostral edge of the lumbar enlargement. 3–5 days after implant, animals without motor dysfunction were tested. Drugs tested in this assay were dissolved in sterile saline (0.9% NaCl) and injected in a volume of 10 ul followed by 10 ul sterile saline to clear the catheter. To test the epidural administration in this assay, modifications are made to the above procedure that are analogous to those made to the allodynia model set forth in Example 9, below.

Animals were examined for the effects of drugs given in the formalin test, in which 50 ul of 5% formalin was injected on the plantar surface of the paw of a lightly anesthetized (halothane, 3%) animal. The number of spontaneous flinching/shaking of the injected paw were counted at intervals after the injection of the formalin. Counts were made for one minute periods, the first time points beginning 2–3 minutes and 5–6 minutes post-injection. Counts were then taken at 5 minute intervals from 10–60 minutes post injection.

Injection of formalin alone or with vehicle (saline) resulted in a biphasic response pattern of hind paw withdrawals (see, for example, FIG. 16). The area under the curve of the flinches/min was calculated for phase 1 (time= 0–10 min) and phase 2 (10–60 min). These values were plotted versus the intrathecal log dose (ug) and the results are shown in FIGS. 17A and 17B.

Dose-response curves were generated using values calculated as percent of the maximum possible inhibition (maximal suppression of the formalin response=100%). The sum of flinches for the observation periods, i.e., the mean total number of flinches for phase 1 (0–9 minutes) and phase 2 (10–60 minutes), respectively, are determined for each control group (i.e., animals receiving intrathecal saline). This is defined as the effect$_{group}$ in that control group. The % of the maximum possible inhibition (% MPI) for each drug treated rat is then calculated by the formula:

$$\% \text{ MPI} = \frac{[\text{Maximum effect}_{group}] - [\text{Maximum effect drug treated rat}]}{\text{Maximum effect in effect}_{group}} \times 100$$

Figure 10A:
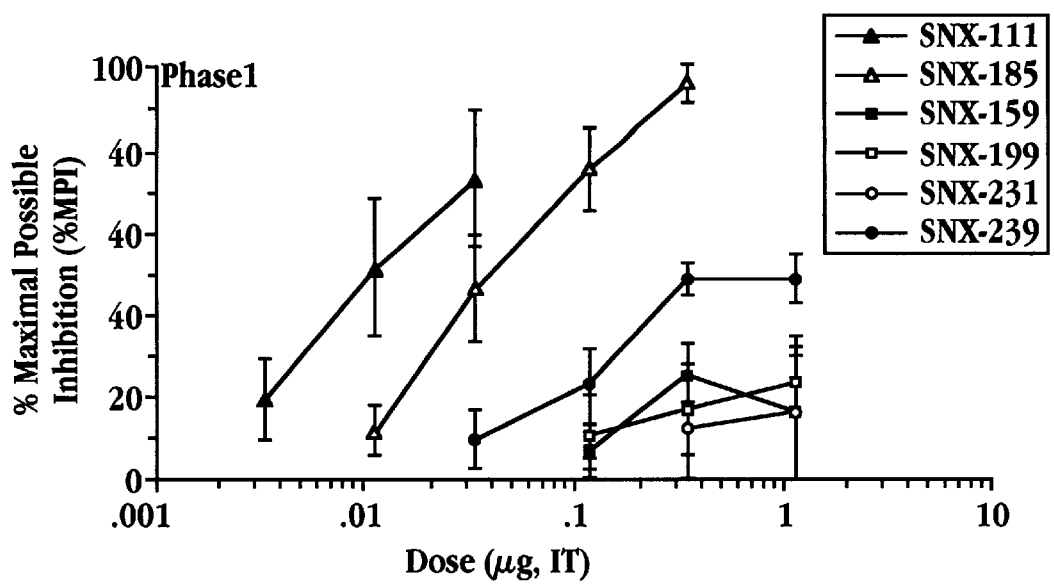
FIGS. 10A and 10B show log dose response curves for effects of SNX-111, SNX-185, SNX-159, SNX-199, SNX-231 and SNX-239 on phase 1(A) and phase 2(B) of the formalin test.
Figure 10B:
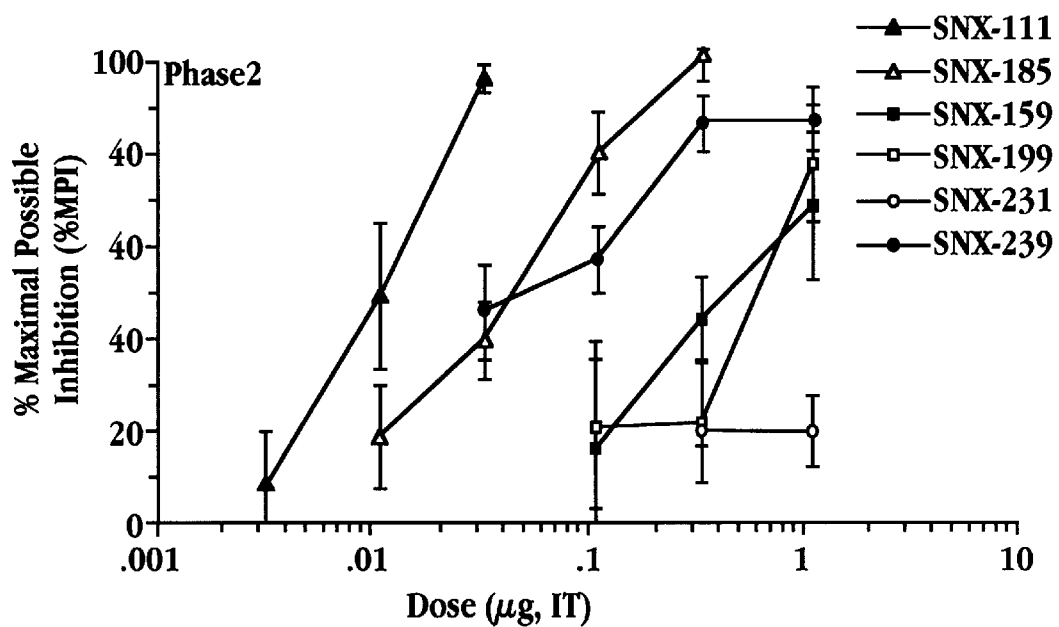

This value calculated for each rat was then used to construct drug group dose-response curves, shown in FIG. 10A for Phase 1 responses and FIG. 10 B for Phase 2 responses. The dose-response lines were fitted using a least square linear regression. ED50 (effective dose resulting in a 50% reduction of the control formalin response) and 95% confidence intervals were calculated according to formulae given by Tallarida and Murray (1987).

Motor function was examined by the placing/stepping reflex, where a normal behavior is a stepping reflex when the hindpaws are drawn across the edge of a table. Righting and ambulation were assessed by placing the rat horizontally with its back on the table with normally gives rise to an immediate coordinated twisting of the body to an upright position. Catalepsy (spontaneous mobility) was tested by placing the forepaws on a horizontal bar kept at 4 cm from a table surface. Failure to move from the bar within 30 seconds was defined as a positive cataleptic response.

EXAMPLE 9

Rat Allodynia Model of Peripheral Neuropathy

For intrathecal administration of compounds, male Sprague-Dawley rats (250–350 gm) were prepared with chronic lumbar intrathecal catheters inserted under halothane anesthesia (Yaksh and Rudy, 1976).

Neuropathogenic surgery: Animals were anesthetized with pentobarbital sodium, placed in a prone position and the left paraspinal muscles were separated from the spinous processes at the $L_4$-$S_2$ levels, as described by Kim and Chung (1992). The left L5 and L6 nerve roots were exposed and tightly ligated with 6–0 surgical silk suture.

Animals were allowed to recover from the neuropathogenic surgery and nociceptive responses were measured daily until the animals exhibited consistent signs of mechanical allodynia (approximately 7–10 days). For epidural administration of drugs, the animals were then implanted with indwelling spinal (lumbar) epidural catheters according to the procedure of Durant and Yaksh (1986), incorporated herein by reference, with minor modifications. SNX-111 or vehicle (saline) was administered either by bolus injection one-day after catheter placement or by continuous, constant-rate infusion initiated at the time of catheter implantation. For bolus injection, SNX-111 was administered in a volume of 30 $\mu$l followed by 10 $\mu$l saline to flush the line. For continuous epidural infusion, catheters were connected to indwelling mini-osmotic pumps and test solutions were delivered at a rate of 1.0 μl/hr. Mechanical allodynia thresholds were measured immediately before and at fixed intervals during or after SNX-111 administration.

For intrathecal administration of drugs, the lumbar subarachnoid space was catheterized with saline-filled polyethylene (PE-10) tubing as described by Yaksh and Rudy (1976). The catheter was anchored with stay sutures to the adjacent muscle tissue where it emerged from the cisterna magna. For bolus injection, test compound was administered in a volume of 10 μl through the intrathecal catheter, followed by 10 μl saline to flush the catheter line. Continuous infusion was carried out as described above.

Animals were given at least 3 days to recover from catheterization before assessing mechanical allodynia thresholds. Allodynia was typically observed to occur beginning 1–2 days post-surgery and continued for as long as 45 days. Animals showing motor deficits were excluded from further study.

For testing, animals were placed in plastic cubicles with open wire mesh bottoms. Compound dissolved in preservative-free saline solution. Animals were tested for allodynia at various time points after drug treatment, as described below.

To assess the threshold of a non-noxious stimulus required to produce a left hind paw withdrawal (allodynia), Von Frey hairs of graded stiffness (ranging from 0.4–15 grams), were systematically applied to the surgically treated plantar of the hind paw. The hair was held against the surface with sufficient force to cause slight bending and held for 6–8 seconds. Failure to evoke a response was cause to test the next stiffer hair. Evocation of a brisk withdrawal response was cause to test the next lower stimulus intensity. This paradigm was repeated according to a statistical method (Dixon, 1976) to define the 50% response threshold. Allodynia was evidenced by a threshold less than 3 grams (referring to the hair stimulus intensity) exhibited by all surgically treated animals.

The mechanical stimulus upper limit for threshold testing was set at 15 grams, as von Frey hairs rated above this bending force tend to raise the limb rather than flex against it. % MPE values near 100 indicate normal mechanical thresholds (i.e. at or near 15 gms); values near 0 indicate allodynia. After completion of testing, animals were killed and the vertebral columns were dissected to confirm the position of the catheters and to examine the condition of the catheter tips. Catheters were then removed and flushed with saline to detect leaks and confirm patency. Animals were excluded from the study if the catheters were obstructed or not appropriately positioned in the epidural space.

Results of animals treated with saline, or various doses of omega-conopeptides are described in conjunction with FIGS. 13–15, above. Data in FIG. 13 are expressed as percent maximum effect, where the maximum effect indicates a complete reversal of allodynia, or insensitivity to stimulus (maximum equals 15 gram hair cutoff). A baseline of zero indicates a mean sensitivity less than 3 grams. As shown in FIG. 13, treatment of rats (n=6/treatment) with 1 or 3 μg SNX-111 resulted in elevation of threshold response. Peak effects were observed by 30–60 minutes, and effects lasted in excess of 60 minutes. Other data were similarly interpreted.

Figure 15A:
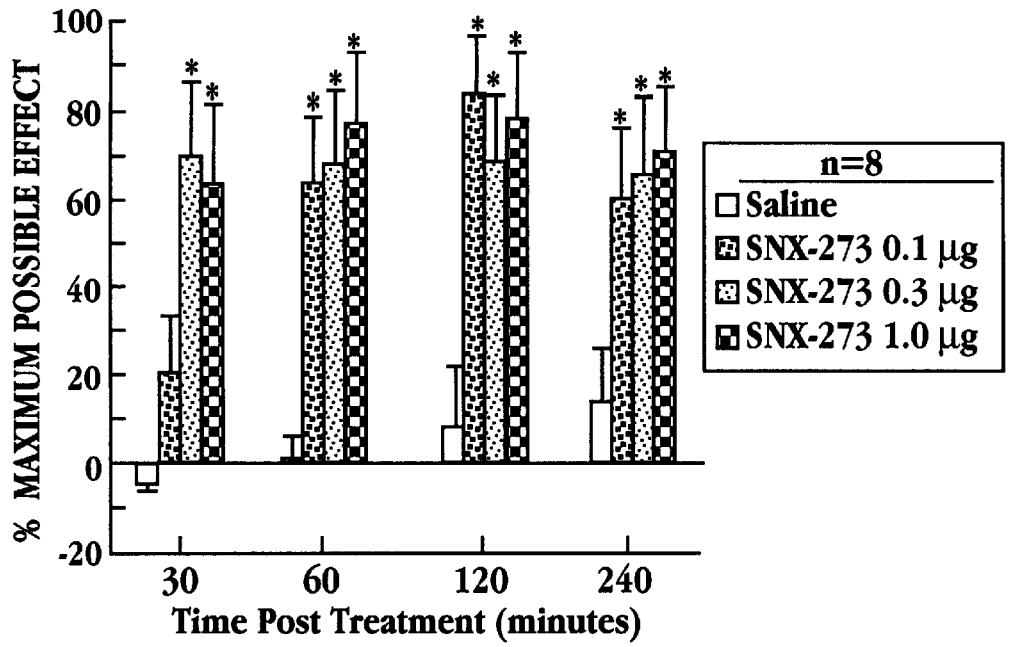
FIGS. 15A and 15B show dose-dependent blockade of mechanical allodynia by SNX-273 (15A) and SNX-279 (15B) in comparison to saline, where asterisks indicate statistically significant differences between treatment and saline ($p<0.05$, Student's t test)
Figure 15B:
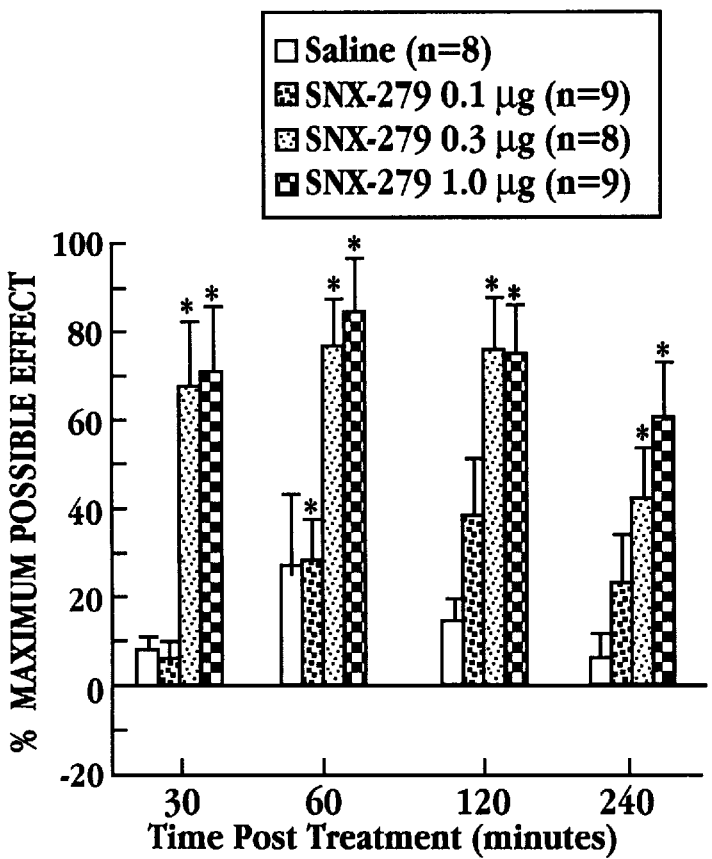

FIGS. 15A and 15B show results of tests in which animals were given a single intrathecal bolus injection of SNX-273 (0.1 μg, 0.3 μg, or 1 μg), SNX-279 (0.1 μg, 0.3 μg, or 1 μg), or vehicle (0.9% Sodium Chloride injection, USP, Sanofi Animal Health, Inc., Overland Park, Kans.). Test control compounds were delivered in a volume of 10 μl followed by 10 μl of saline to flush the catheter. Results of allodynia tests, performed as described above, are shown as percentage of maximum possible effect (MPE):

$$\% \ MPE = \frac{\text{New Threshold (g)} - \text{Baseline Threshold (g)} \times 100}{15 \ \text{grams} - \text{Baseline Threshold}}$$

According to this analysis, the higher the % MPE, the better the antinociceptive effect. As shown in FIG. 15A and 15B, SNX-273 and SNX-279 each blocked mechanical allodynia significantly in comparison to saline control (asterisks in the figures indicate statistically significant differences between treatment and saline, p<0.05, Student's t test). The apparent order of potency for suppression of allodynia is SNX-111= SNX-273>SNX-279. This is consistent with the compounds' relative affinities at the SNX-111 binding site ($IC_{50}$'s: SNX-111, 8 pM; SNX-273, 8 pM; SNX-279, 40 pM).

Animals were also observed for the appearance of general motor dysfunction, as evidenced by inability to ambulate symmetrically and for any other overt signs of unusual activity. No effects on motor activity were observed in saline-treated animals; a dose-dependent tremor characteristic of SNX-111 administration was observed in animals given SNX-111.

EXAMPLE 10

Methionine-Lactate Buffer Formulations

Analgesic efficacy of spinally-administered SNX-111 was tested using a methionine-lactate buffer formulation in the paradigm detailed in Example 4. SNX-111 (10 μg/ml) and L-methionine (50 μg/ml) were dissolved in a vehicle comprised of sodium lactate (150 mM) adjusted to pH 4–4.5 with 250 mM lactic acid. This formulation was used to deliver 0.1 μg SNX-111 intrathecally, as described in Example 5 at 30, 60, 120 and 240 minutes after treatment with test or control compound. FIG. 9 shows effects on mechanical allodynia of a single intrathecal bolus injection of 10 μl saline (open circles) or lactate buffer (150 mM) containing 50 μg/ml methionine with (closed squares) or without (closed triangles) 10 μg/ml SNX-111. Neither saline alone or methionine lactate control buffer alone was effective to suppress allodynia, whereas the SNX-111 formulation was effective in this regard (FIG. 16). Moreover, it was observed that % MPE values for saline-treated controls were not significantly different from those of animals given methionine-lactate buffer alone.

Although the invention has been described with respect to particular embodiments, it will be apparent to those skilled that various changes and modifications can be made without departing from the invention.

It is claimed:

1. In a method of producing analgesia in a mammalian subject by administering to the subject, an omega conopeptide composition which is effective (a) to inhibit electrically stimulated contraction of the guinea pig ileum, and (b) to bind selectively to omega conopeptide MVIIA binding sites present in neuronal tissue, wherein the activities of the omega conopeptide in inhibition of guinea pig ileum and in binding to the MVIIA binding site are within the ranges of such activities of omega-conotoxins MVIIA and TVIA, the improvement comprising administering said omega conopeptide composition via a spinal epidural route over a period of time such that said conopeptide is in prolonged contact with the epidural region, at a dosage that is in the range of an effective intrathecal analgesic dose administered over an equivalent period of time.

2. The method of claim 1, wherein said epidural administering is via continuous infusion.

3. The method of claim 2, wherein said dosage is measured over a twenty-four hour time period.

4. The method of claim 1, wherein said prolonged contact is effected by administering said conopeptide in a sustained release formulation.

5. The method of claim 1, wherein said administering is carried out in the absence in said composition of an agent for enhancing permeation of the conopeptide through meningeal membranes.

6. The method of claim 5, wherein said analgesia is produced in a patient experiencing neuropathic pain, and said administering is effective to prevent further progression of a neuropathic condition underlying said pain.

7. The method of claim 1, wherein said conopeptide is selected from the group consisting of conopeptides identified by SEQ ID NO: 1 (MVIIA/SNX-111), SEQ ID NO: 7 (TVIA/SNX-185), SEQ ID NO: 30 (SNX-236), SEQ ID NO: 2 (SNX-159), SEQ ID NO: 32 (SNX-239), SEQ ID NO: 33 (SNX-199), SEQ ID NO: 35 (SNX-273), SEQ ID NO: 36 (SNX-279), and derivatives thereof.

8. The method of claim 7, wherein said conopeptide is identified by SEQ ID NO: 1 (MVIIA/SNX-111).

9. The method of claim 1, wherein said activity to bind selectively to omega conopeptide MVIIA binding sites is further evidenced by a selectivity ratio of binding at said MVIIA binding site to binding at a site 2 omega conopeptide binding site which is within the range of selectivity ratios determined for omega conopeptides MVIIA/SNX-111, SNX-199, SNX-236, SNX-239 and TVIA/SNX-185.

* * * * *

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
      (A) LENGTH: 25 amino acids
      (B) TYPE: amino acid
      (D) TOPOLOGY: linear (ii) MOLECULE TYPE: protein (iii) HYPOTHETICAL: NO (vi) ORIGINAL SOURCE:
      (C) INDIVIDUAL ISOLATE: MVIIA/SNX-111, FIGURE 1

(xi) SEQUENCE DESCRIPTION: SEQ ID NO:1:

```
Cys Lys Gly Lys Gly Ala Lys Cys Ser Arg Leu Met Tyr Asp Cys Cy
1               5                  10                  15

Thr Gly Ser Cys Arg Ser Gly Lys Cys
            20                  25
```

(2) INFORMATION FOR SEQ ID NO:2:

(i) SEQUENCE CHARACTERISTICS:
      (A) LENGTH: 25 amino acids
      (B) TYPE: amino acid
      (D) TOPOLOGY: linear (ii) MOLECULE TYPE: protein (iii) HYPOTHETICAL: NO (vi) ORIGINAL SOURCE:
      (C) INDIVIDUAL ISOLATE: MVIIB/SNX-159, FIGURE 1

(xi) SEQUENCE DESCRIPTION: SEQ ID NO:2:

```
Cys Lys Gly Lys Gly Ala Ser Cys His Arg Thr Ser Tyr Asp Cys Cy
1               5                  10                  15

Thr Gly Ser Cys Asn Arg Gly Lys Cys
            20                  25
```

(2) INFORMATION FOR SEQ ID NO:3:

(i) SEQUENCE CHARACTERISTICS:
      (A) LENGTH: 27 amino acids
      (B) TYPE: amino acid
      (D) TOPOLOGY: linear (ii) MOLECULE TYPE: protein (iii) HYPOTHETICAL: NO (vi) ORIGINAL SOURCE:
      (C) INDIVIDUAL ISOLATE: GVIA/SNX-124, FIGURE 1

(ix) FEATURE:
      (A) NAME/KEY: Modified-site
      (B) LOCATION: 4
      (D) OTHER INFORMATION: /note= "where X is hydroxyproline"

(ix) FEATURE:
      (A) NAME/KEY: Modified-site
      (B) LOCATION: 10
      (D) OTHER INFORMATION: /note= "where X is hydroxyproline"

(ix) FEATURE:

(A) NAME/KEY: Modified-site
        (B) LOCATION: 21
        (D) OTHER INFORMATION: / note: "where X is hydroxyproline"

(xi) SEQUENCE DESCRIPTION: SEQ ID NO:3:

Cys Lys Ser Xaa Gly Ser Ser Cys Ser Xaa Thr Ser Tyr Asn Cys Cy
1               5                  10                  15

Arg Ser Cys Asn Xaa Tyr Thr Lys Arg Cys Tyr
            20                  25

(2) INFORMATION FOR SEQ ID NO:4:

(i) SEQUENCE CHARACTERISTICS:
        (A) LENGTH: 29 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: GVIIA/SNX-178, FIGURE 1

(ix) FEATURE:
        (A) NAME/KEY: Modified-site
        (B) LOCATION: 4
        (D) OTHER INFORMATION: /note= "where X is hydroxyproline"

(ix) FEATURE:
        (A) NAME/KEY: Modified-site
        (B) LOCATION: 7
        (D) OTHER INFORMATION: /note= "where X is hydroxyproline"

(xi) SEQUENCE DESCRIPTION: SEQ ID NO:4:

Cys Lys Ser Xaa Gly Thr Xaa Cys Ser Arg Gly Met Arg Asp Cys Cy
1               5                  10                  15

Thr Ser Cys Leu Leu Tyr Ser Asn Lys Cys Arg Arg Tyr
            20                  25

(2) INFORMATION FOR SEQ ID NO:5:

(i) SEQUENCE CHARACTERISTICS:
        (A) LENGTH: 27 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: RVIA/SNX-182, FIGURE 1

(ix) FEATURE:
        (A) NAME/KEY: Modified-site
        (B) LOCATION: 4
        (D) OTHER INFORMATION: /note= "where X is hydroxyproline"

(ix) FEATURE:
        (A) NAME/KEY: Modified-site
        (B) LOCATION: 7
        (D) OTHER INFORMATION: /note= "where X is hydroxyproline"

(xi) SEQUENCE DESCRIPTION: SEQ ID NO:5:

Cys Lys Pro Xaa Gly Ser Xaa Cys Arg Val Ser Ser Tyr Asn Cys Cy
1               5                  10                  15

Ser Ser Cys Lys Ser Tyr Asn Lys Lys Cys Gly
            20                  25

```
(2) INFORMATION FOR SEQ ID NO:6:

(i) SEQUENCE CHARACTERISTICS:
        (A) LENGTH: 24 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: SVIA/SNX-157, FIGURE 1

(ix) FEATURE:
        (A) NAME/KEY: Modified-site
        (B) LOCATION: 7
        (D) OTHER INFORMATION: /note= "where X is hydroxyproline"

(xi) SEQUENCE DESCRIPTION: SEQ ID NO:6:

Cys Arg Ser Ser Gly Ser Xaa Cys Gly Val Thr Ser Ile Cys Cys Gl
1               5                   10                  15

Arg Cys Tyr Arg Gly Lys Cys Thr
            20

(2) INFORMATION FOR SEQ ID NO:7:

(i) SEQUENCE CHARACTERISTICS:
        (A) LENGTH: 27 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: TVIA/SNX-185, FIGURE 1

(ix) FEATURE:
        (A) NAME/KEY: Modified-site
        (B) LOCATION: 4
        (D) OTHER INFORMATION: /note= "where X is hydroxyproline"

(ix) FEATURE:
        (A) NAME/KEY: Modified-site
        (B) LOCATION: 10
        (D) OTHER INFORMATION: /note= "where X is hydroxyproline"

(ix) FEATURE:
        (A) NAME/KEY: Modified-site
        (B) LOCATION: 21
        (D) OTHER INFORMATION: /note= "where X is hydroxyproline"

(xi) SEQUENCE DESCRIPTION: SEQ ID NO:7:

Cys Leu Ser Xaa Gly Ser Ser Cys Ser Xaa Thr Ser Tyr Asn Cys Cy
1               5                   10                  15

Arg Ser Cys Asn Xaa Tyr Ser Arg Lys Cys Arg
            20                  25

(2) INFORMATION FOR SEQ ID NO:8:

(i) SEQUENCE CHARACTERISTICS:
        (A) LENGTH: 26 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: SVIB/SNX-183, FIGURE 1
```

(xi) SEQUENCE DESCRIPTION: SEQ ID NO:8:

Cys Lys Leu Lys Gly Gln Ser Cys Arg Lys Thr Ser Tyr Asp Cys Cy
1               5                   10                  15

Ser Gly Ser Cys Gly Arg Ser Gly Lys Cys
            20                  25

(2) INFORMATION FOR SEQ ID NO:9:

(i) SEQUENCE CHARACTERISTICS:
        (A) LENGTH: 25 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: SNX-190, FIGURE 2

(xi) SEQUENCE DESCRIPTION: SEQ ID NO:9:

Cys Lys Gly Ala Gly Ala Lys Cys Ser Arg Leu Met Tyr Asp Cys Cy
1               5                   10                  15

Thr Gly Ser Cys Arg Ser Gly Lys Cys
            20                  25

(2) INFORMATION FOR SEQ ID NO:10:

(i) SEQUENCE CHARACTERISTICS:
        (A) LENGTH: 25 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: SNX-191, FIGURE 2

(xi) SEQUENCE DESCRIPTION: SEQ ID NO:10:

Cys Ala Gly Ala Gly Ala Lys Cys Ser Arg Leu Met Tyr Asp Cys Cy
1               5                   10                  15

Thr Gly Ser Cys Arg Ser Gly Lys Cys
            20                  25

(2) INFORMATION FOR SEQ ID NO:11:

(i) SEQUENCE CHARACTERISTICS:
        (A) LENGTH: 26 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: SNX-193, FIGURE 2

(xi) SEQUENCE DESCRIPTION: SEQ ID NO:11:

Cys Lys Gly Ala Gly Ala Lys Cys Ser Arg Leu Met Tyr Asp Cys Cy
1               5                   10                  15

Thr Gly Ser Cys Arg Ser Gly Lys Cys Gly
            20                  25

(2) INFORMATION FOR SEQ ID NO:12:

(i) SEQUENCE CHARACTERISTICS:
        (A) LENGTH: 25 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: SNX-194, FIGURE 2

(ix) FEATURE:
        (A) NAME/KEY: Modified-site
        (B) LOCATION: 12
        (D) OTHER INFORMATION: /note= "where X is Nle"

(xi) SEQUENCE DESCRIPTION: SEQ ID NO:12:

Cys Lys Gly Ala Gly Ala Lys Cys Ser Arg Leu Xaa Tyr Asp Cys Cy
1               5                   10                  15

Thr Gly Ser Cys Arg Ser Gly Lys Cys
            20                  25

(2) INFORMATION FOR SEQ ID NO:13:

(i) SEQUENCE CHARACTERISTICS:
        (A) LENGTH: 25 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: SNX-195, FIGURE 2

(xi) SEQUENCE DESCRIPTION: SEQ ID NO:13:

Cys Lys Gly Ala Gly Ala Lys Cys Ser Arg Leu Xaa Tyr Asp Cys Cy
1               5                   10                  15

Thr Gly Ser Cys Arg Ser Gly Ala Cys
            20                  25

(2) INFORMATION FOR SEQ ID NO:14:

(i) SEQUENCE CHARACTERISTICS:
        (A) LENGTH: 27 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: SNX-196, FIGURE 2

(xi) SEQUENCE DESCRIPTION: SEQ ID NO:14:

Asn Cys Lys Gly Ala Gly Ala Lys Cys Ser Arg Leu Xaa Tyr Asp Cy
1               5                   10                  15

Cys Thr Gly Ser Cys Arg Ser Gly Ala Cys Gly
            20                  25

(2) INFORMATION FOR SEQ ID NO:15:

(i) SEQUENCE CHARACTERISTICS:
        (A) LENGTH: 27 amino acids
        (B) TYPE: amino acid (D) TOPOLOGY: linear (ii) MOLECULE TYPE: protein (iii) HYPOTHETICAL: NO (vi) ORIGINAL SOURCE:
            (C) INDIVIDUAL ISOLATE: SNX-197, FIGURE 2

(xi) SEQUENCE DESCRIPTION: SEQ ID NO:15:

Asn Ser Cys Lys Gly Ala Gly Ala Lys Cys Ser Arg Leu Xaa Tyr As
1               5                   10                  15

Cys Cys Thr Gly Ser Cys Arg Ser Gly Ala Cys
            20                  25

(2) INFORMATION FOR SEQ ID NO:16:

(i) SEQUENCE CHARACTERISTICS:
            (A) LENGTH: 25 amino acids
            (B) TYPE: amino acid
            (D) TOPOLOGY: linear (ii) MOLECULE TYPE: protein (iii) HYPOTHETICAL: NO (vi) ORIGINAL SOURCE:
            (C) INDIVIDUAL ISOLATE: SNX-198, FIGURE 2

(xi) SEQUENCE DESCRIPTION: SEQ ID NO:16:

Cys Lys Gly Lys Gly Ala Lys Cys Ser Arg Leu Met Tyr Asp Cys Cy
1               5                   10                  15

Thr Gly Ser Cys Ala Ser Gly Lys Cys
            20                  25

(2) INFORMATION FOR SEQ ID NO:17:

(i) SEQUENCE CHARACTERISTICS:
            (A) LENGTH: 25 amino acids
            (B) TYPE: amino acid
            (D) TOPOLOGY: linear (ii) MOLECULE TYPE: protein (iii) HYPOTHETICAL: NO (vi) ORIGINAL SOURCE:
            (C) INDIVIDUAL ISOLATE: SNX-200, FIGURE 2

(xi) SEQUENCE DESCRIPTION: SEQ ID NO:17:

Cys Lys Gly Ala Gly Ala Ala Cys Ser Arg Leu Met Tyr Asp Cys Cy
1               5                   10                  15

Thr Gly Ser Cys Arg Ser Gly Lys Cys
            20                  25

(2) INFORMATION FOR SEQ ID NO:18:

(i) SEQUENCE CHARACTERISTICS:
            (A) LENGTH: 25 amino acids
            (B) TYPE: amino acid
            (D) TOPOLOGY: linear (ii) MOLECULE TYPE: protein (iii) HYPOTHETICAL: NO (vi) ORIGINAL SOURCE:
            (C) INDIVIDUAL ISOLATE: SNX-201, FIGURE 2

(xi) SEQUENCE DESCRIPTION: SEQ ID NO:18:

```
Cys Lys Gly Lys Gly Ala Lys Cys Arg Lys Thr Ser Tyr Asp Cys Cy
1               5                   10                  15

Thr Gly Ser Cys Arg Ser Gly Lys Cys
            20                  25
```

(2) INFORMATION FOR SEQ ID NO:19:

(i) SEQUENCE CHARACTERISTICS:
        (A) LENGTH: 26 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: SNX-202, FIGURE 2

(xi) SEQUENCE DESCRIPTION: SEQ ID NO:19:

```
Cys Lys Leu Lys Gly Gln Ser Cys Ser Arg Leu Met Tyr Asp Cys Cy
1               5                   10                  15

Ser Gly Ser Cys Gly Arg Ser Gly Lys Cys
            20                  25
```

(2) INFORMATION FOR SEQ ID NO:20:

(i) SEQUENCE CHARACTERISTICS:
        (A) LENGTH: 27 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: SNX-207, FIGURE 2

(ix) FEATURE:
        (A) NAME/KEY: Modified-site
        (B) LOCATION: 4
        (D) OTHER INFORMATION: /note= "where X is hydroxyproline"

(ix) FEATURE:
        (A) NAME/KEY: Modified-site
        (B) LOCATION: 21
        (D) OTHER INFORMATION: /note= "where X is hydroxyproline"

(xi) SEQUENCE DESCRIPTION: SEQ ID NO:20:

```
Cys Leu Ser Xaa Gly Ser Ser Cys Ser Arg Leu Met Tyr Asn Cys Cy
1               5                   10                  15

Arg Ser Cys Asn Xaa Tyr Ser Arg Lys Cys Arg
            20                  25
```

(2) INFORMATION FOR SEQ ID NO:21:

(i) SEQUENCE CHARACTERISTICS:
        (A) LENGTH: 26 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: SNX-231, FIGURE 1

(ix) FEATURE:

(A) NAME/KEY: Modified-site
          (B) LOCATION: 7
          (D) OTHER INFORMATION: /note= "where X is hydroxyproline"

(xi) SEQUENCE DESCRIPTION: SEQ ID NO:21:

Cys Lys Gly Lys Gly Ala Xaa Cys Arg Lys Thr Met Tyr Asp Cys Cy
1               5                  10                  15

Ser Gly Ser Cys Gly Arg Arg Gly Lys Cys
            20                  25

(2) INFORMATION FOR SEQ ID NO:22:

(i) SEQUENCE CHARACTERISTICS:
         (A) LENGTH: 6 amino acids
         (B) TYPE: amino acid
         (D) TOPOLOGY: linear (ii) MOLECULE TYPE: protein (iii) HYPOTHETICAL: NO (vi) ORIGINAL SOURCE:
         (C) INDIVIDUAL ISOLATE: CONOPEPTIDE GROUP 1 FRAGMENT,
             PAGE 33, LINES 16-28

(xi) SEQUENCE DESCRIPTION: SEQ ID NO:22:

Cys Lys Gly Lys Gly Ala
1               5

(2) INFORMATION FOR SEQ ID NO:23:

(i) SEQUENCE CHARACTERISTICS:
         (A) LENGTH: 1 amino acids
         (B) TYPE: amino acid
         (D) TOPOLOGY: linear (ii) MOLECULE TYPE: protein (iii) HYPOTHETICAL: NO (vi) ORIGINAL SOURCE:
         (C) INDIVIDUAL ISOLATE: CONOPEPTIDE GROUP 1 FRAGMENT,
             PAGE 33, LINES 16-28

(xi) SEQUENCE DESCRIPTION: SEQ ID NO:23:

Cys
1

(2) INFORMATION FOR SEQ ID NO:24:

(i) SEQUENCE CHARACTERISTICS:
         (A) LENGTH: 8 amino acids
         (B) TYPE: amino acid
         (D) TOPOLOGY: linear (ii) MOLECULE TYPE: protein (iii) HYPOTHETICAL: NO (vi) ORIGINAL SOURCE:
         (C) INDIVIDUAL ISOLATE: CONOPEPTIDE GROUP 1 FRAGMENT,
             PAGE 33, LINES 16-28

(xi) SEQUENCE DESCRIPTION: SEQ ID NO:24:

Tyr Asp Cys Cys Thr Gly Ser Cys
1               5

(2) INFORMATION FOR SEQ ID NO:25:

(i) SEQUENCE CHARACTERISTICS:

(A) LENGTH: 1 amino acids
            (B) TYPE: amino acid
            (D) TOPOLOGY: linear (ii) MOLECULE TYPE: protein (iii) HYPOTHETICAL: NO (vi) ORIGINAL SOURCE:
            (C) INDIVIDUAL ISOLATE: CONOPEPTIDE GROUP 1 FRAGMENT,
                PAGE 33, LINES 16-28

(xi) SEQUENCE DESCRIPTION: SEQ ID NO:25:

Arg
 1

(2) INFORMATION FOR SEQ ID NO:26:

(i) SEQUENCE CHARACTERISTICS:
            (A) LENGTH: 3 amino acids
            (B) TYPE: amino acid
            (D) TOPOLOGY: linear (ii) MOLECULE TYPE: protein (iii) HYPOTHETICAL: NO (vi) ORIGINAL SOURCE:
            (C) INDIVIDUAL ISOLATE: CONOPEPTIDE GROUP 1 FRAGMENT,
                PAGE 33, LINES 16-28

(xi) SEQUENCE DESCRIPTION: SEQ ID NO:26:

Gly Lys Cys
 1

(2) INFORMATION FOR SEQ ID NO:27:

(i) SEQUENCE CHARACTERISTICS:
            (A) LENGTH: 9 amino acids
            (B) TYPE: amino acid
            (D) TOPOLOGY: linear (ii) MOLECULE TYPE: protein (iii) HYPOTHETICAL: NO (vi) ORIGINAL SOURCE:
            (C) INDIVIDUAL ISOLATE: CONOPEPTIDE GROUP 2 FRAGMENT,
                page 33, line29 to page 34, line4

(ix) FEATURE:
            (A) NAME/KEY: Modified-site
            (B) LOCATION: 4
            (D) OTHER INFORMATION: /note= "where X is hydroxyproline"

(xi) SEQUENCE DESCRIPTION: SEQ ID NO:27:

Cys Leu Ser Xaa Gly Ser Ser Cys Ser
 1               5

(2) INFORMATION FOR SEQ ID NO:28:

(i) SEQUENCE CHARACTERISTICS:
            (A) LENGTH: 8 amino acids
            (B) TYPE: amino acid
            (D) TOPOLOGY: linear (ii) MOLECULE TYPE: protein (iii) HYPOTHETICAL: NO (vi) ORIGINAL SOURCE:
            (C) INDIVIDUAL ISOLATE: CONOPEPTIDE GROUP 2 FRAGMENT,
                PAGE 33, line29 to page 34, line4

(xi) SEQUENCE DESCRIPTION: SEQ ID NO:28:

Tyr Asn Cys Cys Arg Ser Cys Asn
1               5

(2) INFORMATION FOR SEQ ID NO:29:

(i) SEQUENCE CHARACTERISTICS:
        (A) LENGTH: 26 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: SNX-230, FIGURE 1

(xi) SEQUENCE DESCRIPTION: SEQ ID NO:29:

Cys Lys Gly Lys Gly Ala Pro Cys Arg Lys Thr Met Tyr Asp Cys Cy
1               5                   10                  15
Ser Gly Ser Cys Gly Arg Arg Gly Lys Cys
            20                  25

(2) INFORMATION FOR SEQ ID NO:30:

(i) SEQUENCE CHARACTERISTICS:
        (A) LENGTH: 27 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: SNX-236, FIGURE 2

(xi) SEQUENCE DESCRIPTION: SEQ ID NO:30:

Cys Leu Ser Xaa Gly Ser Ser Cys Ser Arg Leu Met Tyr Asn Cys Cy
1               5                   10                  15
Arg Ser Cys Asn Pro Tyr Ser Arg Lys Cys Arg
            20                  25

(2) INFORMATION FOR SEQ ID NO:31:

(i) SEQUENCE CHARACTERISTICS:
        (A) LENGTH: 6 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: CONOPEPTIDE GROUP 2 FRAGMENT,
            PAGE 33 line29 to page 34, line4

(xi) SEQUENCE DESCRIPTION: SEQ ID NO:31:

Tyr Ser Arg Lys Cys Arg
1               5

(2) INFORMATION FOR SEQ ID NO:32:

(i) SEQUENCE CHARACTERISTICS:
        (A) LENGTH: 25 amino acids
        (B) TYPE: amino acid (D) TOPOLOGY: linear (ii) MOLECULE TYPE: protein (iii) HYPOTHETICAL: NO (vi) ORIGINAL SOURCE:
        (C) INDIVIDUAL ISOLATE: SNX-239, FIGURE 2

(xi) SEQUENCE DESCRIPTION: SEQ ID NO:32:

Cys Lys Gly Lys Gly Ala Lys Cys Ser Leu Leu Met Tyr Asp Cys Cy
1               5                   10                  15

Thr Gly Ser Cys Arg Ser Gly Lys Cys
            20                  25

(2) INFORMATION FOR SEQ ID NO:33:

(i) SEQUENCE CHARACTERISTICS:
        (A) LENGTH: 25 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: SNX-199, FIGURE 2

(xi) SEQUENCE DESCRIPTION: SEQ ID NO:33:

Cys Lys Gly Lys Gly Ala Lys Cys Ser Ala Leu Met Tyr Asp Cys Cy
1               5                   10                  15

Thr Gly Ser Cys Arg Ser Gly Lys Cys
            20                  25

(2) INFORMATION FOR SEQ ID NO:34:

(i) SEQUENCE CHARACTERISTICS:
        (A) LENGTH: 25 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: SNX 240, FIGURE 2

(ix) FEATURE:
        (A) NAME/KEY: Modified-site
        (B) LOCATION: 1
        (D) OTHER INFORMATION: /note= "The cysteine residue
            carries an acetyl group"

(xi) SEQUENCE DESCRIPTION: SEQ ID NO:34:

Cys Lys Gly Lys Gly Ala Lys Cys Ser Leu Leu Met Tyr Asp Cys Cy
1               5                   10                  15

Thr Gly Ser Cys Arg Ser Gly Lys Cys
            20                  25

(2) INFORMATION FOR SEQ ID NO:35:

(i) SEQUENCE CHARACTERISTICS:
        (A) LENGTH: 25 amino acids
        (B) TYPE: amino acid
        (D) TOPOLOGY: linear (ii) MOLECULE TYPE: protein

```
            -continued (iii) HYPOTHETICAL: NO (vi) ORIGINAL SOURCE:
          (C) INDIVIDUAL ISOLATE: MVIIA/SNX-111, FIGURE 2

(xi) SEQUENCE DESCRIPTION: SEQ ID NO:35:

Cys Lys Gly Lys Gly Ala Lys Cys Ser Arg Leu Ala Tyr Asp Cys Cy
1               5                   10                  15

Thr Gly Ser Cys Arg Ser Gly Lys Cys
            20              25

(2) INFORMATION FOR SEQ ID NO:36:

(i) SEQUENCE CHARACTERISTICS:
          (A) LENGTH: 25 amino acids
          (B) TYPE: amino acid
          (D) TOPOLOGY: linear (ii) MOLECULE TYPE: protein (iii) HYPOTHETICAL: NO (vi) ORIGINAL SOURCE:
          (C) INDIVIDUAL ISOLATE: MVIIA/SNX-111, FIGURE 2

(ix) FEATURE:
          (A) NAME/KEY: Modified-site
          (B) LOCATION: 12
          (D) OTHER INFORMATION: /note: "where X is
              sulfoxy-methionine"

(xi) SEQUENCE DESCRIPTION: SEQ ID NO:36:

Cys Lys Gly Lys Gly Ala Lys Cys Ser Arg Leu Xaa Tyr Asp Cys Cy
1               5                   10                  15

Thr Gly Ser Cys Arg Ser Gly Lys Cys
            20              25
```